(12) United States Patent
Felgner et al.

(10) Patent No.: US 10,197,577 B2
(45) Date of Patent: Feb. 5, 2019

(54) SERUM ANTIBODY ASSAY FOR DETERMINING PROTECTION FROM MALARIA, AND PRE-ERYTHROCYTIC SUBUNIT VACCINES

(71) Applicants: Sanaria Inc., Rockville, MD (US); Antigen Discovery, Inc., Irvine, CA (US); The United States of America, as represented by the Secretary, Department of Health and Human Services, Washington, DC (US)

(72) Inventors: Philip Felgner, Irvine, CA (US); Stephen L. Hoffman, Rockville, MD (US); Robert Seder, Bethesda, MD (US); Joseph J. Campo, Jr., Irvine, CA (US)

(73) Assignees: Sanaria Inc., Rockville, MD (US); Antigen Discovery, Inc., Irvine, CA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/858,560

(22) Filed: Dec. 29, 2017

(65) Prior Publication Data
US 2018/0231566 A1  Aug. 16, 2018

Related U.S. Application Data

(62) Division of application No. 15/060,959, filed on Mar. 4, 2016.

(60) Provisional application No. 62/128,400, filed on Mar. 4, 2015.

(51) Int. Cl.
| | | |
|---|---|---|
| A61K 39/00 | (2006.01) | |
| G01N 33/68 | (2006.01) | |
| A61K 39/015 | (2006.01) | |
| G01N 33/569 | (2006.01) | |

(52) U.S. Cl.
CPC ....... *G01N 33/6854* (2013.01); *A61K 39/015* (2013.01); *G01N 33/56905* (2013.01); *A61K 2039/521* (2013.01); *A61K 2039/522* (2013.01); *A61K 2039/54* (2013.01); *G01N 2333/445* (2013.01); *G01N 2469/20* (2013.01); *Y02A 50/58* (2018.01)

(58) Field of Classification Search
CPC .................................................. G01N 33/6854
See application file for complete search history.

(56) References Cited

U.S. PATENT DOCUMENTS

| | | | |
|---|---|---|---|
| 4,244,940 A | 1/1981 | Jeong et al. | |
| 8,043,625 B2 | 10/2011 | Sim et al. | |
| 8,367,810 B2 | 2/2013 | Sim et al. | |
| 8,802,919 B2 | 8/2014 | Hoffman et al. | |
| 8,821,896 B2 | 9/2014 | Sim et al. | |
| 8,992,944 B2 | 3/2015 | Sim et al. | |
| 9,241,982 B2 | 1/2016 | Sim et al. | |
| 9,278,125 B2 | 3/2016 | Chakravarty et al. | |
| 9,878,026 B2 | 1/2018 | Eappen et al. | |
| 2005/0208078 A1 | 9/2005 | Hoffman et al. | |
| 2005/0266017 A1 | 12/2005 | Druilhe et al. | |
| 2008/0260763 A1 | 10/2008 | Felgner et al. | |
| 2012/0128725 A1 | 5/2012 | Akira et al. | |
| 2012/0156245 A1 | 6/2012 | Hoffman et al. | |
| 2012/0288525 A1 | 11/2012 | Chakravarty et al. | |
| 2014/0348870 A1 | 11/2014 | Felgner et al. | |
| 2015/0313980 A1 | 11/2015 | Janse et al. | |
| 2016/0158351 A1 | 6/2016 | Chakravarty et al. | |
| 2016/0175417 A1 | 6/2016 | Sim et al. | |
| 2016/0216276 A1 | 7/2016 | Felgner et al. | |
| 2016/0320404 A1 | 11/2016 | Felgner et al. | |

FOREIGN PATENT DOCUMENTS

| | | |
|---|---|---|
| WO | WO 2006/061965 A1 | 6/2006 |
| WO | WO 2015/031904 A2 | 3/2015 |

OTHER PUBLICATIONS

Alonso, P.L., et al., "A Research Agenda for Malaria Eradication: Vaccines," *PLoS Medicine* 8(1): e1000398:1-10, Public Library of Science, United States (2011).

Chulay, J.D., et al., "Malaria Transmitted to Humans by Mosquitoes Infected from Cultured *Plasmodium falciparum,*" *The American Journal of Tropical Medicine and Hygiene* 35(1):66-68, The American Society of Tropical Medicine and Hygiene, United States (1986).

Clyde, D.F., et al., "Immunization of man against sporozite-induced falciparum malaria," *The American Journal of the Medical Sciences* 266(3):169-177, Charles B. Slack Inc., United States (1973).

Droucheau, E., et al., "*Plasmodium falciparum* glycogen synthase kinase-3: molecular model, expression, intracellular localisation and selective inhibitors," *Biochimica et Biophysica Acta* 1697(1-2):181-196, Elsevier B.V., Netherlands (2004).

Epstein, J.E., et al., "Live Attenuated Malaria Vaccine Designed to Protect Through Hepatic CD8+ T Cell Immunity," *Science* 334(6055):475-480, American Association for the Advancement of Science, United States (2011).

Farrell, A., et al., "A DOC2 Protein Identified by Mutational Profiling is Essential for Apicomplexan Parasite Exocytosis," *Science* 335(6065):218-221, American Association for the Advancement of Science, United States (2012).

(Continued)

*Primary Examiner* — Albert M Navarro
(74) *Attorney, Agent, or Firm* — Sterne, Kessler, Goldstein & Fox P.L.L.C.

(57) ABSTRACT

Disclosed herein are diagnostic methods and compositions for identifying individuals that are protected against *Plasmodium falciparum* caused malaria. Such methods are particularly useful for determining not only the protective efficacy of Pf whole parasite vaccines for individual subjects, but also within populations of vaccinated subjects. Also disclosed herein are subunit vaccines comprising at least one Pf immunologic determinant for protection against *Plasmodium*-caused malaria.

20 Claims, 12 Drawing Sheets

Specification includes a Sequence Listing.

(56) References Cited

OTHER PUBLICATIONS

Gamo, F.-J., et al., "Thousands of chemical starting points for antimalarial lead identification," *Nature* 465(7296):305-310, Macmillan Publishers Limited, England, including 2 pages of Methods (2010).
Hoffman, S.L. and Doolan, D.L., "Malaria vaccines-targeting infected hepatocytes," *Nature Medicine* 6(11):1218-1219, Nature America Inc., United States (2000).
Hoffman, S.L., et al., "Development of a metabolically active, non-replicating sporozoite vaccine to prevent *Plasmodium falciparum* malaria," *Human Vaccines* 6(1):97-106, Landes Bioscience, United States (2010).
Hoffman, S.L., et al., "Protection of Humans against Malaria by Immunization with Radiation-Attenuated *Plasmodium falciparum* Sporozoites," *J Infect Dis* 185:1155-1164, Infectious Diseases Society of America, United States (2002).
Jean, S., et al., "*Plasmodium falciparum* double C2 domain protein, PfDOC2, binds to calcium when associated with membranes," *Experimental Parasitology* 144:91-95, Elsevier Inc., United States (2014).
Kester, K.E., et al., "Randomized, Double-Blind, Phase 2a Trial of Falciparum Malaria Vaccines RTS,S/AS01B and RTS,S/AS02A in Malaria-Naive Adults: Safety, Efficacy, and Immunologic Associates of Protection," *The Journal of Infectious Diseases* 200(3):337-346, Infectious Diseases Society of America, United States (2009).
Lanzer, M., et al., "Maurer's clefts: A novel multi-functional organelle in the cytoplasm of *Plasmodium falciparum*-infected erythrocytes," *International Journal for Parasitology* 36(1):23-36, Elsevier Ltd., England (2006).
Lasonder, E., et al., "The *Plasmodium falciparum* Schizont Phosphoproteome Reveals Extensive Phosphatidylinositol and cAMP-Protein Kinase A Signaling," *Journal of Proteome Research* 11(11):5323-5337, American Chemical Society, United States (2012).
Lindner, S.E., et al., "Total and Putative Surface Proteomics of Malaria Parasite Salivary Gland Sporozoites," *Molecular & Cellular Proteomics* 12(5):1127-1143, The American Society for Biochemistry and Molecular Biology Inc., United States (2013).
Luke, T.C. and Hoffman, S.L., "Rationale and plans for developing a non-replicating, metabolically active, radiation-attenuated *Plasmodium falciparum* sporozoite vaccine," *The Journal of Experimental Biology* 206(Pt 21):3803-3808, The Company of Biologists Ltd, England (2003).
Lyke, K.E., et al., "*Plasmodium falciparum* Malaria Challenge by the Bite of Aseptic *Anopheles stephensi* Mosquitoes: Results of a Randomized Infectivity Trial," *PLoS One* 5(10):e13490:1-10, Public Library of Science, United States (2010).
Murray, C.J., et al., "Global malaria mortality between 1980 and 2010: a systematic analysis," *Lancet* 379(9814):413-431, Elsevier, England (2012).
Nussenzweig, R.S., et al., "Protective Immunity Produced by the Injection of X-irradiated Sporozoites of *Plasmodium berghei*," *Nature* 216(5111):160-162, Macmillan (Journals), Ltd., England (1967).
Osolodkin, D.I., et al., "Bioinformatic analysis of glycogen synthase kinase 3. human versus parasite kinases," *Parasitology* 138(6):725-735, Cambridge University Press, England (2011).

Plowe, C.V., et al., "The Potential Role of Vaccines in the Elimination of Falciparum Malaria and the Eventual Eradication of Malaria," *J Infect Dis* 200:1646-1649, Infectious Disease Society of America, United States (2009).
Ponnudurai, T., et al., "The production of mature gametocytes of *Plasmodium falciparum* in continuous cultures of different isolates infective to mosquitoes," *Transactions of the Royal Society of Tropical Medicine and Hygiene* 76(2):242-250, Oxford University Press, England (1982).
Rickman, L.S., et al., "*Plasmodium falciparum*-Infected *Anopheles stephensi* Inconsistently Transmit Malaria to Humans," *The American Journal of Tropical Medicine and Hygiene* 43(5):441-445, The American Society of Tropical Medicine and Hygiene, United States (1990).
Rieckmann, K.H., et al., "Letter: Sporozoite Induced Immunity in Man Against an Ethiopian Strain of *Plasmodium falciparum*," *Transactions of the Royal Society of Tropical Medicine and Hygiene* 68(3):258-259, Oxford University Press, England (1974).
Seder, R.A., et al., "Protection Against Malaria by Intravenous Immunization with a Nonreplicating Sporozoite Vaccine," *Sciencexpress* 1-12, American Association for the Advancement of Science, United States (Aug. 8, 2013); later published as Science 341(6152):1359-1365 (Sep. 20, 2013).
Smith, B.D., et al., "Evaluation of Three Rapid Screening Assays for Detection of Antibodies to Hepatitis C Virus," *The Journal of Infectious Diseases* 204(6):825-831, Oxford University Press on behalf of the Infectious Diseases Society of America, United States (2011).
Treeck, M., et al., "The Phosphoproteomes of *Plasmodium falciparum* and *Toxoplasma gondii* Reveal Unusual Adaptations within and Beyond the Parasites' Boundaries," *Cell Host & Microbe* 10(4):410-419, Elsevier Inc., United States (2011).
National Institutes of Health Clinical Center, Clinical Trial Identifier NCT02015091 entitled "Study of Controlled Human Malaria Infections to Evaluate Protection After Intravenous or Intramuscular Administration of PfSPZ Vaccine in Malaria-Naive Adults," ClinicalTrials.gov, available at https://clinicaltrials.gov/ct2/show/NCT02015091, last accessed on Jul. 12, 2016, 5 pages.
World Health Organization, Malaria Vaccine Technology Roadmap Aug. 2006, available at http://www.who.int/immunization/sage/meetings/2013/april/7_Malaria_Vaccine_TRM_Final.pdf, last accessed on Jul. 13, 2016, 24 pages.
World Health Organization, World Malaria Report 2013, available at http://www.who.int/malaria/publications/world_malaria_report_2012/report/en/, last accessed on Jul. 12, 2016, 288 pages.
World Health Organization, World Malaria Report 2013, available at http://www.who.int/malaria/publications/world_malaria_report_2013/en/, accessed on Mar. 24, 2016, 284 pages.
Office Action dated Jul. 6, 2017, in U.S. Appl.No. 15/060,959, Felgner., et al., filed Mar. 4, 2016, 14 pages.
Written Opinion for International Application No. PCT/US2016/020830, United States Patent and Trademark Office, United States, dated Aug. 26, 2016, 10 pages.
Gardner, M.J., et al., "Genome sequence of the human malaria parasite *Plasmodium falciparum*," *Nature* 419:34 pages, Nature Publishing Group, England (2002).
Lambert, P.H., et al., "Can successful vaccines teach us how to induce efficient protective immune responses?" *Nature Medicine Supplement* 11(4):554-562, Nature Publishing Group, England (2005).
International Search Report for International Application No. PCT/US16/20830, United States Patent and Trademark Office, United States, dated Aug. 26, 2016, 6 pages.

```
                     SEQUENCE LISTING

<160> NUMBER OF SEQ ID NOS: 20

<210> SEQ ID NO 1
<211> LENGTH: 1350
<212> TYPE: DNA
<213> ORGANISM: Plasmodium falciparum

<400> SEQUENCE: 1
atggcgagag tgcggaaggg gaaagccatg cccgtaatgt ctaaaaactc aatattcgtt      60
ttaaatataa ttatgactat aggttttata agtgctatac ctcagatttt cacaaacttta    120 atgacatcat ggagagaagc tgaacctata gaatataaat acatgtttag aggaagtgaa    180
cattccttat atgttgatta tacatattac ggtttatata aagtagtata tgataataaa    240
catgtagaga cttggacaca acgagtacag aatatgaaaa ggaaaggtat agaaggtata    300
caacaaggta aaaatagtga atcagctggt agcttatcat tatggacatc tgtatgtcct    360
gaagcttgta gagatgctat tgttagacgt atagaagcat atgaaagagt ttctttttata    420 tctttagtac ttttatgtgg tattgtcata tcatgtacta ttgttatctt gtcagttggt    480
tggaatttat tattttcaaa aagcatattt atattaatgg gatgttttat tttttcattt    540
gttataaatg ctggtatcgg tacctattgg tattatgaaa cagatatgtc gtggaactct    600
ataactaaag cacaacaata tcctttcccc cggtgctcac attgttttta cgtttttatg    660
attactacag gaatatatgc actctgtttt cttagcttat tattattaga cttatttaat    720
aaaggcaaac aaaaatcatc acaccgagat caacttaatg cacataatag aaaccctatg    780
aataataaag ctatgtacca acctatgttc gataatcaac cgggtatgat gatgcagaga    840
agtgctagtt actctaatat tatgccatttt gttaaaggaa tgaataataa tgattattct    900
aattatatgc aatataataa aatgggaatg aatatgaaca tgaatatgaa ccaaatgcca    960
```

```
caacaaggat tcccaaattt tagaaatatg ggatccaatg tgggcccaaa tatgggatca      1020
cctatgggat cacctatggg accatctatg ggatcaccta tgggtccatc tatgggatca      1080
cccatgggac caaatatggg gtcccctatg agttctccaa tgggttcaca tatgggtccc      1140
aatttgaatc ccaattttt ccctcaacaa tcaaggcaat attcttattc agtttcccca      1200
acgtatcaac aaaacatgcc taatttaat aacttttcaa atagacatat gccatctatg      1260
tctgatttat attttgcaag acaatattca gggatgaaat tggggacat gaataacagt      1320 ccatttgatt cacagaaacc atataaattt                                      1350
```

<210> SEQ ID NO 2
<211> LENGTH: 747
<212> TYPE: DNA
<213> ORGANISM: Plasmodium falciparum

<400> SEQUENCE: 2

```
gaggatataa atatttatga agaaaagaat catacgaata acaaaaatta tgttaataat        60
tttgagatga gtgatcagaa ggacgaagag gagtatagcc atagtagtaa tagaagtgag       120
gatgaagatg aggaaagaac tatagataat gagattaata ggtctcctaa taaatcttat       180
aaattaggaa atattatagg gaatggtagt tttggtgttg tatatgaggc tatatgtata       240
gatacgtcag aacaagttgc gataaaaaag gttttacaag atccacaata taaaaataga       300
gaattaatga ttatgaaaaa tttaaatcat ataaatataa tatatttaaa agattattat       360
tatactgaat cttttaaaaa aaatgagaaa aatatatttc taaatgtagt tatggaatat       420 atacccaga ctgtacataa atatatgaaa tattattcta gaataatca agccttgcca         480 atgtttctag tgaaattata ttcatatcaa ctatgcaggg ctctatcata tattcattca       540
aaatttattt gtcatagaga tcttaaacct caaaacttat aatagatcc tagaacacat        600 acacttaaat tatgtgattt tggtagtgcc aaaaatctat tagctgggca agaagtgtc        660 tcatatattt gttcaaggtt ttatcgagca cctgaactta tgttgggctc aacaaattac       720
acaacacata tagatttatg gtccta                                            747
```

<210> SEQ ID NO 3
<211> LENGTH: 384
<212> TYPE: DNA
<213> ORGANISM: Plasmodium falciparum

<400> SEQUENCE: 3

```
atgatactag acaaatttaa aaatattgta aatcttagta atagtaatac agaaaaagaa        60
gaagggaaaa atgcagaaat aaatgaaaat aatgatccaa atacccagct agctcatgaa       120
ccttctattg ttgaagcaga tgaaaaaaca ttttttgatg aaatgttagg agctcctcaa       180
tatacttatg atgaattttt acaagtatta aaaaatccca tagaagaaag aggagataca       240
gaggatatga aaaagcattg gggatatcct aggagatgga agttattct atgggattta        300 catatacaaa attatatgaa taatgatttt aatgctttg tagattttga ttttggtggt        360
aacagggaag agtgtagaat acaa                                              384
```

<210> SEQ ID NO 4
<211> LENGTH: 1464
<212> TYPE: DNA
<213> ORGANISM: Plasmodium falciparum

<400> SEQUENCE: 4

| | | |
|---|---|---|
| atgaatgaag aaaactacaa tgtgaatgat aaggatagtc catcctttat attttatgaa | 60 | |
| aaaacatatg aaggtgatga cacgtgcttt tttaatataa ttataagttt taaaaaactg | 120 | |
| aaaatatata atgaaaaaga ttttgaagaa gttataaatt tgaatgcaga acatatattg | 180 | |
| aaggatattg taaagataga ggagggttta caaaggaata tatataatac tgaaataatt | 240 | |
| aaaaagagaa ataataaaaa gagaaacaaa aaaaagaag ttttgatat agatataaat | 300 | |
| aatgaaatgg ataatgaaaa tatgaatgac attaattata atcctaataa atatgataat | 360 | |
| tgtgatgatc tttataaaaa ttataaagag cggtttgaca tccttattaa tgaacttaat | 420 | |
| gattctaata taaaaagtta tacgctaaaa gaaaaatctg agggagaaga agaaaaaaaa | 480 | |
| aaattgtgtg taatgtggga acttgattta tcatataatt attttaaaga aatttctatt | 540 | |
| gataatatat tatccattat gataagcaaa aatattatcc ctcataagaa tattttacaa | 600 | |
| ttaaataatt taagaacatt aaacttaagg aagaataatt taatatattt tccttatatt | 660 | |
| tcaaattttg tattggatgg cttagttaat atacacatat cacataatta tataaatgga | 720 | |
| tgtaataatt atatagataa aatagataat atgcatatata aagtaaaaa cttatgtgaa | 780 | |
| gaggatataa aaaataaaat aaataatatc aattttaata atgaaggtac atggaataag | 840 | |
| ataataccta atttaaaaaa tatttatgta cagaataatt atttgcaatc ttttttttct | 900 | |
| ttaaatatt taattaataa acataaaaac ataaaatata taaatattag ttttaataaa | 960 | |
| attaacttct taacagattt atttatctta aaaaatgtag aacatataaa tttgtcttat | 1020 | |
| aacacttta tgaacgtaga aagtaatatg acatcacatg gaataacaaa agatataaac | 1080 | |
| aataacatgg atgaaaagaa cgatatatac cataataata ttaataaaaa tgagacaact | 1140 | |
| caacaagatg aagaaataac tataaacgta gatcacacaa ttgaacaaac gtctacacat | 1200 | |
| ttttgtatag aaggacaaga aaataaaaat atgttaattt cggatagcac atataaaaat | 1260 | |
| cagcatgata atgataataa caatgttcat aataaagaca ataataatga aattatattt | 1320 | |
| cataaccttt tattaaattt gaaattttt tttccatctt taaaaaatct aaatataaaa | 1380 | |
| tatacagaag tttaccaaaa atttaagctc tatataaaga aggaagatta taaatatgaa | 1440 | |
| cagaattatt ttattgattt taaa | 1464 | |

<210> SEQ ID NO 5
<211> LENGTH: 594
<212> TYPE: DNA
<213> ORGANISM: Plasmodium falciparum

<400> SEQUENCE: 5

| | | |
|---|---|---|
| gagcaaaaac acagggataa gaatgcaaaa ttaagaaaag agacagaatt aaagaaatcc | 60 | |
| ttagattaca tcaaaaatta tagatgggaa cgttgtatat cctatttgca ttattccaac | 120 | |
| tgcttaaaag ataagaatat agaatttgaa ttggaatata attattgtaa ccccacctta | 180 | |
| gaagagttaa aaaagatat gcattttttat gatgaagagg acgataatga agaagaaagt | 240 | |
| acacaaaatg ataatccaaa tgataaaaca gatgacgtac cattattatt acctttggat | 300 | |
| gtattcaatt taccatcaac ttatgatatg tatgattcat attataaatc ttccacatat | 360 | |
| tatagtaaag acgaaaaaga agataaggca aaaattaaat ttccagataa ttcacaaaac | 420 | |
| aaatttgata ttatgtgtga ttttaaaaaa tgcgaaaata ctaacatatc tgtggaagaa | 480 | |
| tcaattaatt taaatcatat gtattataac tttccttctt catattatgt cttcaactat | 540 | |
| ttatttaacg attatgtgga agatttatct gtggtagatc aaattagaat acaa | 594 | |

<210> SEQ ID NO 6
<211> LENGTH: 1356
<212> TYPE: DNA
<213> ORGANISM: Plasmodium falciparum

<400> SEQUENCE: 6

| | | | | | |
|---|---|---|---|---|---|
| gaaaaattta | ttggacaaga | tcaaacatat | ggtcaactga | atgaaaataa | cccagaacaa | 60 |
| aataatatat | tgtcaaaatg | taataataag | aagaatcgaa | acattcaaaa | taatcttcaa | 120 |
| tatgaaaata | cttgtagtac | accagaacaa | ataaattatc | acaatagttt | aattaaatgt | 180 |
| aaagcaaaca | ttgtagatat | caaatatgta | acctacatat | tcaaatcctt | tttaagaatc | 240 |
| tctttattta | atccaggaca | cctaaaaaat | aaaaaaaatt | ttattcaatt | acttgagaac | 300 |
| tctttcataa | attatgtcaa | cagatatata | tataattatc | aaaaggaaga | taaaaatttt | 360 |
| aatgaaataa | atgacacgaa | tcatttaata | aaaagaaaag | aaacacgtgg | aataaatgga | 420 |
| agctctcata | taatgtgtc | catagataat | caaaaaataa | atgtaacata | taatatgtat | 480 |
| gatgataaaa | atagtaatct | tttgtacaag | gaacctttc | attttaatat | ttatgataat | 540 |
| gatttaagtt | tatatgaatt | aagttccata | tgtgaatgct | ttttttcttgt | cgagtatata | 600 |
| aacagccaag | atttttcaaaa | tataaacaac | ataaaagttg | taagaaaaaa | gaaaaatata | 660 |
| caaaataata | atgctcatcg | tgtagaaaaa | gaaaagtgtg | taatattcaa | tagtgatgat | 720 |
| atatttgaaa | aactttata | tatattttta | gataaaatga | atagattcgt | ttgtaataaa | 780 |
| aaactaaatc | ttactacatc | taatgaggat | tatataaaaa | atgtattatt | ggaaaaattc | 840 |
| ttaaatcaag | gagatatatt | ttttaattat | tatttattat | taagattact | attacctta | 900 |
| ttatttagtg | catctcttga | tcattatata | ttattgagta | agagactcat | tgttcatata | 960 |
| ttatctttaa | tatttcacaa | aaaaatgaaa | gaacaaataa | acaaaggtat | aaagaacaat | 1020 |
| attttacata | ttacaaatgt | aatcaatgat | tatatgaagt | gggaaaattc | atttatatat | 1080 |
| ataaataatc | aaaggaggat | aaggaaacaa | accaaaaacca | aaatgaattt | attagatttt | 1140 |
| atttatacag | gtgagttcat | taggccttca | ttcatactta | ttctgattat | aaatgaatta | 1200 |
| aagaattatg | atgatatgtt | tgaccaattt | atacaaaata | ttttttaaaaa | tgatgctaac | 1260 |
| ataaaagaaa | ataagaaaga | tcttacaaat | tatatagaca | aaatgtacaa | aaaaatgtat | 1320 |
| gcccttgtta | ttaaaaagga | gaaggaaggg | ttatta | | | 1356 |

<210> SEQ ID NO 7
<211> LENGTH: 321
<212> TYPE: DNA
<213> ORGANISM: Plasmodium falciparum

<400> SEQUENCE: 7

| | | | | | |
|---|---|---|---|---|---|
| cccttggaca | ttctagtttg | tgcaggatta | ataagctcaa | aaaaattaat | tgaggctcaa | 60 |
| gctattttaa | aagaaaataa | taaaagatta | caagaagtga | agaattcttc | cttcgctaat | 120 |
| aattccaatg | aaaagagttt | agaaaaagaa | aaaaataaaa | accctaatga | aaatggatct | 180 |
| ttactttcta | attctttagc | tgtggaggta | gatttgagtg | gttgcttttt | ttttcattct | 240 |
| tcttttacat | gtcctattag | tagagataag | tcctccaggg | acaaccctcc | ttatctactt | 300 |
| acctgtggtc | atgccatttg | c | | | | 321 |

<210> SEQ ID NO 8
<211> LENGTH: 2565
<212> TYPE: DNA
<213> ORGANISM: Plasmodium falciparum

<400> SEQUENCE: 8

```
gcaagtaaaa acttcagcct ttcaaattac aatttagatt taattaaatg tttacaagat      60
gactcgggaa tatatttcat tttagatcct agtaaagcta ttaatgaaaa gaaacaatca     120
gatgtgtatg atatatttgt accagaggat acggaaggtg taacacttca tgttcaaaag     180
atgaatgatg aatataaatg tattggtgtt agtataacta aaaaaggtat agatataaat     240
tcaggaactc gtattttaa ttccaaaatt tcagattggc tagaacaatt atttgttttt      300
aataagaact taataaataa tggtttacaa atgaatgaga aaatgaaaaa aattccaaat     360
aacacttctg ttcttaacac aaataatgtt aactctggtg cttcttttat gaatggggat     420
attaacggaa atataaatat tcctataaat gctatcaatt ataagaatga taaatttata     480
aataaaggta gcaatatcaa tattataaat gaaggtagca atttaacaca ctctaaaaat     540
acaaattata ataatatgaa acgtgcatct ggcacctcga atttacaaga cacaacaact     600
actaatttaa taaaaaataa ataataataat ttagaatatt ttgaaaataa agagaaaaat    660
aacctaatgc ttcctaacaa taataataat aatatcaata atatgagtaa tatgaatggt     720
catattaaca attcacattt atcgaataaa aaggaaata aaaataataa ccaacacaat      780
tgcaatataa atcataatat caataataat aataataata ataataattt tgttggtaat    840
cataatttac cttcttcaca aatgcaaaaa caaaatagat taaatcttgt caataataat    900
aataataata aaaatgctca ttcaaataaa tcaaatacaa tgaattttaa aaatatgaat     960
tttgatgaaa aaaatagtaa attatttaac aatattagtg ctagcagttt attaatgaat    1020
aaaaatattc tatctaatgt aaatgcttta gcagctcaaa tatctcttgg agcaagctct    1080
gaatttatga agaataataa attaggtgta ggacatacaa ataacaatag ccagaaaaat    1140
aatacatata atttacataa tcatctgcaa aatgaattat ttaatttacc aaatcatctt    1200
caaaataatc ttatgtttaa taacaataat aataaatccc aattacatca attacaaaat    1260
tcacaaaatc aaaataatgt acatcaacac attcaaaatc aaaatgcatc aaatcaacaa    1320
ataaatcaat cttataatga taatttttaca tatcgaccta cattatttaa tttgttagaa    1380
gttttagcta accataatat cacaactccc gatcaacgtg tatgtattag aggtattgtt    1440
acagatttct tgaataatga attacctcat ggaaaaatat atgcatatat tggtgctgtt    1500
gtaggacatg atattctaca tgatatcatt aaaaaaattag aaaaggatcc caacagaaat    1560
gtggttccag atgcatcagg attagctaga attgaagcag cttttggctt aagcaagtca    1620
tcctatgatt ttattaataa taattcacag aattccaccg taggtaattt atctaatgtg    1680
ctatttaaca atcgtaattt aaatagtgca cttttaaata accaattttta ttctaatatt    1740
ttatcaaatg tagctaacaa tgctcttaat gctaataatc ttttaaataa taatgaaagg    1800
gtgagccttg ataatgataa aatattaagt agtaaagcag cagcagatat aagtaatttg    1860
ttgaaatacg caaaaaatga aaaaatgtct atgtctgcta ataataacgt aatgaatttt    1920
aatcgaaaaa aaggagcaaa ttttaataat ttgttgaatt taagaaatga tcctcccaat    1980
aataataata ataataataa taataataat aataatatga atactttaa taataataat     2040
atgaatactt ttaataataa taataataat aatagtaata ataatcatat aaataataat    2100
attaataatt tcaataataa tagtagaaat acaattcctc atgatcttat cagtgcagct    2160
acaagaaatt ttaatataca atgccaacat aaaaatagct tttctgatga agaagaagaa    2220
ttaatgaaag ttattaagaa aaatatagaa tcatataaaa tgaataatat taaaaatatc    2280
ctgatatcat cagttttttgg tagaattaaa tggttaaaaa ttatgaacga atcaccacat    2340
```

```
gcttatttat atggacatag tatagtaaaa tttggtaaca aattatatat gtttggtggt    2400
tcgaatggta aaaataaaaa aattccgttt actcatacat taacattcag tttaatttat    2460
tacaattata aattattacc tttaagtggt aattgtcctg aagagcgaga gggacatact    2520
acacatttag tttctttgca taatggttta tctgtattct tattt                   2565
```

<210> SEQ ID NO 9
<211> LENGTH: 1194
<212> TYPE: DNA
<213> ORGANISM: Plasmodium falciparum
<220> FEATURE:
<221> NAME/KEY: misc_feature
<222> LOCATION: (1)..(1194)
<223> OTHER INFORMATION: PFC0210c

<400> SEQUENCE: 9

```
atgatgagaa aattagctat tttatctgtt tcttcctttt tatttgttga ggccttattc      60
caggaatacc agtgctatgg aagttcgtca aacacaaggg ttctaaatga attaaattat     120
gataatgcag gcactaattt atataatgaa ttagaaatga attattatgg gaaacaggaa     180
aattggtata gtcttaaaaa aaatagtaga tcacttggag aaaatgatga tggaaataac     240
gaagacaacg agaaattaag gaaaccaaaa cataaaaaat taaagcaacc agcggatggt     300
aatcctgatc caaatgcaaa cccaaatgta gatcccaatg ccaacccaaa tgtagatcca     360
aatgcaaacc caaatgtaga tccaaatgca aacccaaatg caaacccaaa tgcaaaccca     420
aatgcaaacc caaatgcaaa cccaaatgca aacccaaatg caaacccaaa tgcaaaccca     480
aatgcaaacc caaatgcaaa cccaaatgca aacccaaatg caaacccaaa tgcaaaccca     540
aatgcaaacc ccaatgcaaa tcctaatgca aacccaaatg caaacccaaa cgtagatcct     600
aatgcaaatc caaatgcaaa cccaaacgca aaccccaatg caaatcctaa tgcaaacccc     660
aatgcaaatc ctaatgcaaa tcctaatgcc aatccaaatg caaatccaaa tgcaaaccca     720
aacgcaaacc ccaatgcaaa tcctaatgcc aatccaaatg caaatccaaa tgcaaaccca     780
aatgcaaacc caaatgcaaa ccccaatgca atcctaata aaaacaatca aggtaatgga     840
caaggtcaca atatgccaaa tgacccaaac cgaaatgtag atgaaaatgc taatgccaac     900
agtgctgtaa aaaataataa taacgaagaa ccaagtgata agcacataaa agaatattta     960
aacaaaatac aaaattctct ttcaactgaa tggtccccat gtagtgtaac ttgtggaaat    1020
ggtattcaag ttagaataaa gcctggctct gctaataaac ctaaagacga attagattat    1080
gcaaatgata ttgaaaaaaa aatttgtaaa atggaaaaat gttccagtgt gtttaatgtc    1140
gtaaatagtt caataggatt aataatggta ttatccttct tgttccttaa ttag          1194
```

<210> SEQ ID NO 10
<211> LENGTH: 819
<212> TYPE: DNA
<213> ORGANISM: Plasmodium falciparum
<220> FEATURE:
<221> NAME/KEY: misc_feature
<222> LOCATION: (1)..(819)
<223> OTHER INFORMATION: PFB0305c

<400> SEQUENCE: 10

```
atgaatatat tatgtattct atcatatatt tatttttttcg ttatttttta tagtttgaat     60
ttaaataata aaaatgaaaa tttttttggtt gtcagaagat taatgaatga cgaaaaagga    120
gaaggtggtt ttacaagtaa aaataaagag atggaaaata ataatagaaa taatgaaaat    180
```

-continued

```
gaactaaaag aagaaggttc tttacctact aagatgaatg aaaaaaattc caattcatca    240
gataaacagc caaatgatat ttcacatgat gaatcaaaga gcaattctaa taattcacaa    300
aatatccaaa aagaacctga agaaaaagag aacagtaacc ctaatttaga tagtagtgaa    360
aattcgagtg aaagcgcaac acgttctgtt gatatatcag aacataattc taataatcca    420
gagacgaaag aagagaatgg agaagaacct ttagatcttg aaattaatga aatgcagaa     480 ataggtcaag aacctccaaa tagattacat tttgacaatg tagatgatga ggtgccacat    540
tatagcgccc taagatataa taaagtagaa aaaaatgtaa ccgatgaaat gttattatat    600
aatatgatga gtgatcaaaa tagaaaatca tgtgccataa ataatggtgg atgttctgat    660
gatcaaatat gtataaatat aataatatat ggagttaaat gtatatgtaa ggatggatat    720
ttacttggta cgaaatgtat aatattgaat tcttattctt gccatccatt ttttctatt     780 cttatttata ttcattgtt tttgttatta ttcgtttaa                           819
```

<210> SEQ ID NO 11
<211> LENGTH: 440
<212> TYPE: PRT
<213> ORGANISM: Plasmodium falciparum

<400> SEQUENCE: 11

```
Met Ala Arg Val Arg Lys Gly Lys Ala Met Pro Val Met Ser Lys Asn
1               5                   10                  15

Ser Ile Phe Val Leu Asn Ile Ile Met Thr Ile Gly Phe Ile Ser Ala
                20                  25                  30

Ile Pro Gln Ile Phe Thr Thr Leu Met Thr Ser Trp Arg Glu Ala Glu
            35                  40                  45

Pro Ile Glu Tyr Lys Tyr Met Phe Arg Gly Ser Glu His Ser Leu Tyr
        50                  55                  60

Val Asp Tyr Thr Tyr Tyr Gly Leu Tyr Lys Val Val Tyr Asp Asn Lys
65                  70                  75                  80

His Val Glu Thr Trp Thr Gln Arg Val Gln Asn Met Lys Arg Lys Gly
                85                  90                  95

Ile Glu Gly Ile Gln Gln Gly Lys Asn Ser Glu Ser Ala Gly Ser Leu
            100                 105                 110

Ser Leu Trp Thr Ser Val Cys Pro Glu Ala Cys Arg Asp Ala Ile Val
        115                 120                 125

Arg Arg Ile Glu Ala Tyr Glu Arg Val Ser Phe Ile Ser Leu Val Leu
    130                 135                 140

Leu Cys Gly Ile Val Ile Ser Cys Thr Ile Val Ile Leu Ser Val Gly
145                 150                 155                 160

Trp Asn Leu Leu Phe Ser Lys Ser Ile Phe Ile Leu Met Gly Cys Phe
                165                 170                 175

Ile Phe Ser Phe Val Ile Asn Ala Gly Ile Gly Thr Tyr Trp Tyr Tyr
            180                 185                 190

Glu Thr Asp Met Ser Trp Asn Ser Ile Thr Lys Ala Gln Gln Tyr Pro
        195                 200                 205

Phe Pro Arg Cys Ser His Cys Phe Tyr Val Phe Met Ile Thr Thr Gly
    210                 215                 220

Ile Tyr Ala Leu Cys Phe Leu Ser Leu Leu Leu Asp Leu Phe Asn
225                 230                 235                 240

Lys Gly Lys Gln Lys Ser Ser His Arg Asp Gln Leu Asn Ala His Asn
                245                 250                 255

Arg Asn Pro Met Asn Asn Lys Ala Met Tyr Gln Pro Met Phe Asp Asn
```

```
                    260                 265                 270
Gln Pro Gly Met Met Met Gln Arg Ser Ala Ser Tyr Ser Asn Ile Met
                275                 280                 285

Pro Phe Val Lys Gly Met Asn Asn Asp Tyr Ser Asn Tyr Met Gln
            290                 295                 300

Tyr Asn Lys Met Gly Met Asn Met Asn Met Asn Met Asn Gln Met Pro
305                 310                 315                 320

Gln Gln Gly Phe Pro Asn Phe Arg Asn Met Gly Ser Asn Val Gly Pro
                325                 330                 335

Asn Met Gly Ser Pro Met Gly Ser Pro Met Gly Pro Ser Met Gly Ser
            340                 345                 350

Pro Met Gly Pro Ser Met Gly Ser Pro Met Gly Pro Asn Met Gly Ser
            355                 360                 365

Pro Met Ser Ser Pro Met Gly Ser His Met Gly Pro Asn Leu Asn Pro
            370                 375                 380

Asn Phe Phe Pro Gln Gln Ser Arg Gln Tyr Ser Tyr Ser Val Ser Pro
385                 390                 395                 400

Thr Tyr Gln Gln Asn Met Pro Asn Phe Asn Asn Phe Ser Asn Arg His
                405                 410                 415

Met Pro Ser Met Ser Asp Leu Tyr Phe Ala Arg Gln Tyr Ser Gly Met
                420                 425                 430

Lys Phe Gly Asp Met Asn Asn Ser
                435                 440

<210> SEQ ID NO 12
<211> LENGTH: 240
<212> TYPE: PRT
<213> ORGANISM: Plasmodium falciparum

<400> SEQUENCE: 12

Glu Asp Ile Asn Ile Tyr Glu Glu Lys Asn His Thr Asn Asn Lys Asn
1               5                   10                  15

Tyr Val Asn Asn Phe Glu Met Ser Asp Gln Lys Asp Glu Glu Glu Tyr
            20                  25                  30

Ser His Ser Ser Asn Arg Ser Glu Asp Glu Asp Glu Glu Arg Thr Ile
        35                  40                  45

Asp Asn Glu Ile Asn Arg Ser Pro Asn Lys Ser Tyr Lys Leu Gly Asn
    50                  55                  60

Ile Ile Gly Asn Gly Ser Phe Gly Val Val Tyr Glu Ala Ile Cys Ile
65                  70                  75                  80

Asp Thr Ser Glu Gln Val Ala Ile Lys Lys Val Leu Gln Asp Pro Gln
                85                  90                  95

Tyr Lys Asn Arg Glu Leu Met Ile Met Lys Asn Leu Asn His Ile Asn
            100                 105                 110

Ile Ile Tyr Leu Lys Asp Tyr Tyr Thr Glu Ser Phe Lys Lys Asn
        115                 120                 125

Glu Lys Asn Ile Phe Leu Asn Val Val Met Glu Tyr Ile Pro Gln Thr
    130                 135                 140

Val His Lys Tyr Met Lys Tyr Tyr Ser Arg Asn Asn Gln Ala Leu Pro
145                 150                 155                 160

Met Phe Leu Val Lys Leu Tyr Ser Tyr Gln Leu Cys Arg Ala Leu Ser
                165                 170                 175

Tyr Ile His Ser Lys Phe Ile Cys His Arg Asp Leu Lys Pro Gln Asn
            180                 185                 190
```

```
Leu Leu Ile Asp Pro Arg Thr His Thr Leu Lys Leu Cys Asp Phe Gly
            195                 200                 205

Ser Ala Lys Asn Leu Leu Ala Gly Gln Arg Ser Val Ser Tyr Ile Cys
        210                 215                 220

Ser Arg Phe Tyr Arg Ala Pro Glu Leu Met Leu Gly Ser Thr Asn Tyr
225                 230                 235                 240

<210> SEQ ID NO 13
<211> LENGTH: 128
<212> TYPE: PRT
<213> ORGANISM: Plasmodium falciparum

<400> SEQUENCE: 13

Met Ile Leu Asp Lys Phe Lys Asn Ile Val Asn Leu Ser Asn Ser Asn
1               5                   10                  15

Thr Glu Lys Glu Glu Gly Lys Asn Ala Glu Ile Asn Glu Asn Asn Asp
            20                  25                  30

Pro Asn Thr Gln Leu Ala His Glu Pro Ser Ile Val Glu Ala Asp Glu
        35                  40                  45

Lys Thr Phe Phe Asp Glu Met Leu Gly Ala Pro Gln Tyr Thr Tyr Asp
    50                  55                  60

Glu Phe Leu Gln Val Leu Lys Asn Pro Ile Glu Arg Gly Asp Thr
65                  70                  75                  80

Glu Asp Met Lys Lys His Trp Gly Tyr Pro Arg Arg Trp Lys Val Ile
                85                  90                  95

Leu Trp Asp Leu His Ile Gln Asn Tyr Met Asn Asn Asp Phe Asn Ala
            100                 105                 110

Phe Val Asp Phe Asp Phe Gly Gly Asn Arg Glu Glu Cys Arg Ile Gln
        115                 120                 125

<210> SEQ ID NO 14
<211> LENGTH: 488
<212> TYPE: PRT
<213> ORGANISM: Plasmodium falciparum

<400> SEQUENCE: 14

Met Asn Glu Glu Asn Tyr Asn Val Asn Asp Lys Asp Ser Pro Ser Phe
1               5                   10                  15

Ile Phe Tyr Glu Lys Thr Tyr Glu Gly Asp Asp Thr Cys Phe Phe Asn
            20                  25                  30

Ile Ile Ile Ser Phe Lys Lys Leu Lys Ile Tyr Asn Glu Lys Asp Phe
        35                  40                  45

Glu Glu Val Ile Asn Leu Asn Ala Glu His Ile Leu Lys Asp Ile Val
    50                  55                  60

Lys Ile Glu Glu Gly Leu Gln Arg Asn Ile Tyr Asn Thr Glu Ile Ile
65                  70                  75                  80

Lys Lys Arg Asn Asn Lys Lys Arg Asn Lys Lys Glu Val Phe Asp
                85                  90                  95

Ile Asp Ile Asn Asn Glu Met Asp Glu Asn Met Asn Asp Ile Asn
            100                 105                 110

Tyr Asn Pro Asn Lys Tyr Asp Asn Cys Asp Asp Leu Tyr Lys Asn Tyr
        115                 120                 125

Lys Glu Arg Phe Asp Ile Leu Ile Asn Glu Leu Asn Asp Ser Asn Ile
    130                 135                 140

Lys Ser Tyr Thr Leu Lys Glu Lys Ser Glu Gly Glu Glu Glu Lys Lys
145                 150                 155                 160
```

Lys Leu Cys Val Met Trp Glu Leu Asp Leu Ser Tyr Asn Tyr Phe Lys
                165                 170                 175

Glu Ile Ser Ile Asp Asn Ile Leu Ser Ile Met Ile Ser Lys Asn Ile
            180                 185                 190

Ile Pro His Lys Asn Ile Leu Gln Leu Asn Asn Leu Arg Thr Leu Asn
        195                 200                 205

Leu Arg Lys Asn Asn Leu Ile Tyr Phe Pro Tyr Ile Ser Asn Phe Val
    210                 215                 220

Leu Asp Gly Leu Val Asn Ile His Ile Ser His Asn Tyr Ile Asn Gly
225                 230                 235                 240

Cys Asn Asn Tyr Ile Asp Lys Ile Asp Asn Met Thr Tyr Ile Ser Lys
                245                 250                 255

Asn Leu Cys Glu Glu Asp Ile Lys Asn Lys Ile Asn Asn Ile Asn Phe
            260                 265                 270

Asn Asn Glu Gly Thr Trp Asn Lys Ile Ile Pro Asn Leu Lys Asn Ile
        275                 280                 285

Tyr Val Gln Asn Asn Tyr Leu Gln Ser Phe Phe Ser Leu Lys Tyr Leu
    290                 295                 300

Ile Asn Lys His Lys Asn Ile Lys Tyr Ile Asn Ile Ser Phe Asn Lys
305                 310                 315                 320

Ile Asn Phe Leu Thr Asp Leu Phe Ile Leu Lys Asn Val Glu His Ile
                325                 330                 335

Asn Leu Ser Tyr Asn Thr Phe Met Asn Val Glu Ser Asn Met Thr Ser
            340                 345                 350

His Gly Ile Thr Lys Asp Ile Asn Asn Met Asp Glu Lys Asn Asp
        355                 360                 365

Ile Tyr His Asn Asn Ile Asn Lys Asn Glu Thr Thr Gln Gln Asp Glu
    370                 375                 380

Glu Ile Thr Ile Asn Val Asp His Thr Ile Glu Gln Thr Ser Thr His
385                 390                 395                 400

Phe Cys Ile Glu Gly Gln Glu Asn Lys Asn Met Leu Ile Ser Asp Ser
                405                 410                 415

Thr Tyr Lys Asn Gln His Asp Asn Asp Asn Asn Val His Asn Lys
            420                 425                 430

Asp Asn Asn Asn Glu Ile Ile Phe His Asn Leu Leu Leu Asn Leu Lys
    435                 440                 445

Phe Phe Phe Pro Ser Leu Lys Asn Leu Asn Ile Lys Tyr Thr Glu Val
450                 455                 460

Tyr Gln Lys Phe Lys Leu Tyr Ile Lys Lys Glu Asp Tyr Lys Tyr Glu
465                 470                 475                 480

Gln Asn Tyr Phe Ile Asp Phe Lys
                485

<210> SEQ ID NO 15
<211> LENGTH: 198
<212> TYPE: PRT
<213> ORGANISM: Plasmodium falciparum

<400> SEQUENCE: 15

Glu Gln Lys His Arg Asp Lys Asn Ala Lys Leu Arg Lys Glu Thr Glu
1               5                   10                  15

Leu Lys Lys Ser Leu Asp Tyr Ile Lys Asn Tyr Arg Trp Glu Arg Cys
            20                  25                  30

Ile Ser Tyr Leu His Tyr Ser Asn Cys Leu Lys Asp Lys Asn Ile Glu
        35                  40                  45

Phe Glu Leu Glu Tyr Asn Tyr Cys Asn Pro Thr Leu Glu Glu Leu Lys
 50                  55                  60

Lys Asp Met His Phe Tyr Asp Glu Glu Asp Asn Glu Glu Glu Glu Ser
 65                  70                  75                  80

Thr Gln Asn Asp Asn Pro Asn Asp Lys Thr Asp Val Pro Leu Leu
                 85                  90                  95

Leu Pro Leu Asp Val Phe Asn Leu Pro Ser Thr Tyr Asp Met Tyr Asp
                100                 105                 110

Ser Tyr Tyr Lys Ser Ser Thr Tyr Tyr Ser Lys Asp Glu Lys Glu Asp
             115                 120                 125

Lys Ala Lys Ile Lys Phe Pro Asp Asn Ser Gln Asn Lys Phe Asp Ile
    130                 135                 140

Met Cys Asp Phe Lys Lys Cys Glu Asn Thr Asn Ile Ser Val Glu Glu
145                 150                 155                 160

Ser Ile Asn Leu Asn His Met Tyr Tyr Asn Phe Pro Ser Ser Tyr Tyr
                165                 170                 175

Val Phe Asn Tyr Leu Phe Asn Asp Tyr Val Glu Asp Leu Ser Val Val
                180                 185                 190

Asp Gln Ile Arg Ile Gln
            195

<210> SEQ ID NO 16
<211> LENGTH: 440
<212> TYPE: PRT
<213> ORGANISM: Plasmodium falciparum

<400> SEQUENCE: 16

Glu Lys Phe Ile Gly Gln Asp Gln Thr Tyr Gly Gln Leu Asn Glu Asn
1               5                   10                  15

Asn Pro Glu Gln Asn Asn Ile Leu Ser Lys Cys Asn Asn Lys Lys Asn
                20                  25                  30

Arg Asn Ile Gln Asn Asn Leu Gln Tyr Glu Asn Thr Cys Ser Thr Pro
            35                  40                  45

Glu Gln Ile Asn Tyr His Asn Ser Leu Ile Lys Cys Lys Ala Asn Ile
 50                  55                  60

Val Asp Ile Lys Tyr Val Thr Tyr Ile Phe Lys Ser Phe Leu Arg Ile
65                  70                  75                  80

Ser Leu Phe Asn Pro Gly His Leu Lys Asn Lys Lys Asn Phe Ile Gln
                85                  90                  95

Leu Leu Glu Asn Ser Phe Ile Asn Tyr Val Asn Arg Tyr Ile Tyr Asn
                100                 105                 110

Tyr Gln Lys Glu Asp Lys Asn Phe Asn Glu Ile Asn Asp Thr Asn His
            115                 120                 125

Leu Ile Lys Arg Lys Glu Thr Arg Gly Ile Asn Gly Ser Ser His Asn
    130                 135                 140

Asn Val Ser Ile Asp Asn Gln Lys Ile Asn Val Thr Tyr Asn Met Tyr
145                 150                 155                 160

Asp Asp Lys Asn Ser Asn Leu Leu Tyr Lys Glu Pro Phe His Phe Asn
                165                 170                 175

Ile Tyr Asp Asn Asp Leu Ser Leu Tyr Glu Leu Ser Ser Ile Cys Glu
                180                 185                 190

Cys Phe Phe Leu Val Glu Tyr Ile Asn Ser Gln Asp Phe Gln Asn Ile
            195                 200                 205

Asn Asn Ile Lys Val Val Lys Lys Lys Lys Asn Ile Gln Asn Asn Asn

```
Ala His Arg Val Glu Lys Glu Lys Cys Val Ile Phe Asn Ser Asp Asp
225                 230                 235                 240

Ile Phe Glu Lys Thr Leu Tyr Ile Phe Leu Asp Lys Met Asn Arg Phe
            245                 250                 255

Val Cys Asn Lys Lys Leu Asn Leu Thr Thr Ser Asn Glu Asp Tyr Ile
                260                 265                 270

Lys Asn Val Leu Leu Glu Lys Phe Leu Asn Gln Gly Asp Ile Phe Phe
            275                 280                 285

Asn Tyr Tyr Leu Leu Leu Arg Leu Leu Pro Leu Leu Phe Ser Ala
290                 295                 300

Ser Leu Asp His Tyr Ile Leu Leu Ser Lys Arg Leu Ile Val His Ile
305                 310                 315                 320

Leu Ser Leu Ile Phe His Lys Lys Met Lys Glu Gln Ile Asn Lys Gly
                325                 330                 335

Ile Lys Asn Asn Ile Leu His Ile Thr Asn Val Ile Asn Asp Tyr Met
            340                 345                 350

Lys Trp Glu Asn Ser Phe Ile Tyr Ile Asn Asn Gln Arg Arg Ile Arg
            355                 360                 365

Lys Gln Thr Lys Thr Lys Met Asn Leu Leu Asp Phe Ile Tyr Thr Gly
370                 375                 380

Glu Phe Ile Arg Pro Ser Phe Ile Leu Ile Leu Ile Asn Glu Leu
385                 390                 395                 400

Lys Asn Tyr Asp Asp Met Phe Asp Gln Phe Ile Gln Asn Ile Phe Lys
            405                 410                 415

Asn Asp Ala Asn Ile Lys Glu Asn Lys Lys Asp Leu Thr Asn Tyr Ile
                420                 425                 430

Asp Lys Met Tyr Lys Lys Met Tyr
            435                 440

<210> SEQ ID NO 17
<211> LENGTH: 107
<212> TYPE: PRT
<213> ORGANISM: Plasmodium falciparum

<400> SEQUENCE: 17

Pro Leu Asp Ile Leu Val Cys Ala Gly Leu Ile Ser Ser Lys Lys Leu
1               5                   10                  15

Ile Glu Ala Gln Ala Ile Leu Lys Glu Asn Asn Lys Arg Leu Gln Glu
            20                  25                  30

Val Lys Asn Ser Ser Phe Ala Asn Asn Ser Asn Glu Lys Ser Leu Glu
        35                  40                  45

Lys Glu Lys Asn Lys Asn Pro Asn Glu Asn Gly Ser Leu Leu Ser Asn
50                  55                  60

Ser Leu Ala Val Glu Val Asp Leu Ser Gly Cys Phe Phe His Ser
65                  70                  75                  80

Ser Phe Thr Cys Pro Ile Ser Arg Asp Lys Ser Arg Asp Asn Pro
                85                  90                  95

Pro Tyr Leu Leu Thr Cys Gly His Ala Ile Cys
            100                 105

<210> SEQ ID NO 18
<211> LENGTH: 840
<212> TYPE: PRT
<213> ORGANISM: Plasmodium falciparum
```

<400> SEQUENCE: 18

```
Ala Ser Lys Asn Phe Ser Leu Ser Asn Tyr Asn Leu Asp Leu Ile Lys
1               5                   10                  15

Cys Leu Gln Asp Asp Ser Gly Ile Tyr Phe Ile Leu Asp Pro Ser Lys
            20                  25                  30

Ala Ile Asn Glu Lys Lys Gln Ser Asp Val Tyr Asp Ile Phe Val Pro
        35                  40                  45

Glu Asp Thr Glu Gly Val Thr Leu His Val Gln Lys Met Asn Asp Glu
    50                  55                  60

Tyr Lys Cys Ile Gly Val Ser Ile Thr Lys Lys Gly Ile Asp Ile Asn
65                  70                  75                  80

Ser Gly Thr Arg Ile Phe Asn Ser Lys Ile Ser Asp Trp Leu Glu Gln
                85                  90                  95

Leu Phe Val Phe Asn Lys Asn Leu Ile Asn Asn Gly Leu Gln Met Asn
            100                 105                 110

Glu Lys Met Lys Lys Ile Pro Asn Asn Thr Ser Val Leu Asn Thr Asn
        115                 120                 125

Asn Val Asn Ser Gly Ala Ser Phe Met Asn Gly Asp Ile Asn Gly Asn
    130                 135                 140

Ile Asn Ile Pro Ile Asn Ala Ile Asn Tyr Lys Asn Asp Lys Phe Ile
145                 150                 155                 160

Asn Lys Gly Ser Asn Ile Asn Ile Ile Asn Glu Gly Ser Asn Leu Thr
                165                 170                 175

His Ser Lys Asn Thr Asn Tyr Asn Asn Met Lys Arg Ala Ser Gly Thr
            180                 185                 190

Ser Asn Leu Gln Asp Thr Thr Thr Asn Leu Ile Lys Asn Lys Tyr
        195                 200                 205

Asn Asn Leu Glu Tyr Phe Glu Asn Lys Glu Lys Asn Asn Leu Met Leu
    210                 215                 220

Pro Asn Asn Asn Asn Asn Ile Asn Asn Met Ser Asn Met Asn Gly
225                 230                 235                 240

His Ile Asn Asn Ser His Leu Ser Asn Lys Lys Gly Asn Lys Asn Asn
                245                 250                 255

Asn Gln His Asn Cys Asn Ile Asn His Asn Ile Asn Asn Asn Asn
            260                 265                 270

Asn Asn Asn Asn Phe Val Gly Asn His Asn Leu Pro Ser Ser Gln Met
    275                 280                 285

Gln Lys Gln Asn Arg Leu Asn Leu Val Asn Asn Asn Asn Asn Asn Lys
290                 295                 300

Asn Ala His Ser Asn Lys Ser Asn Thr Met Asn Phe Lys Asn Met Asn
305                 310                 315                 320

Phe Asp Glu Lys Asn Ser Lys Leu Phe Asn Asn Ile Ser Ala Ser Ser
                325                 330                 335

Leu Leu Met Asn Lys Asn Ile Leu Ser Asn Val Asn Ala Leu Ala Ala
            340                 345                 350

Gln Ile Ser Leu Gly Ala Ser Ser Glu Phe Met Lys Asn Asn Lys Leu
        355                 360                 365

Gly Val Gly His Thr Asn Asn Ser Gln Lys Asn Asn Thr Tyr Asn
370                 375                 380

Leu His Asn His Leu Gln Asn Glu Leu Phe Asn Leu Pro Asn His Leu
385                 390                 395                 400

Gln Asn Asn Leu Met Phe Asn Asn Asn Asn Lys Ser Gln Leu His
                405                 410                 415
```

```
Gln Leu Gln Asn Ser Gln Asn Gln Asn Asn Val His Gln His Ile Gln
            420                 425                 430

Asn Gln Asn Ala Ser Asn Gln Gln Ile Asn Gln Ser Tyr Asn Asp Asn
            435                 440                 445

Phe Thr Tyr Arg Pro Thr Leu Phe Asn Leu Leu Glu Val Leu Ala Asn
450                 455                 460

His Asn Ile Thr Thr Pro Asp Gln Arg Val Cys Ile Arg Gly Ile Val
465                 470                 475                 480

Thr Asp Phe Leu Asn Asn Glu Leu Pro His Gly Lys Ile Tyr Ala Tyr
            485                 490                 495

Ile Gly Ala Val Val Gly His Asp Ile Leu His Asp Ile Ile Lys Lys
            500                 505                 510

Leu Glu Lys Asp Pro Asn Arg Asn Val Val Pro Asp Ala Ser Gly Leu
            515                 520                 525

Ala Arg Ile Glu Ala Ala Phe Gly Leu Ser Lys Ser Ser Tyr Asp Phe
            530                 535                 540

Ile Asn Asn Asn Ser Gln Asn Ser Thr Val Gly Asn Leu Ser Asn Val
545                 550                 555                 560

Leu Phe Asn Asn Arg Asn Leu Asn Ser Ala Leu Leu Asn Asn Gln Phe
            565                 570                 575

Tyr Ser Asn Ile Leu Ser Asn Val Ala Asn Asn Ala Leu Asn Ala Asn
            580                 585                 590

Asn Leu Leu Asn Asn Asn Glu Arg Val Ser Leu Asp Asn Asp Lys Ile
            595                 600                 605

Leu Ser Ser Lys Ala Ala Ala Asp Ile Ser Asn Leu Leu Lys Tyr Ala
            610                 615                 620

Lys Asn Glu Lys Met Ser Met Ser Ala Asn Asn Asn Val Met Asn Phe
625                 630                 635                 640

Asn Arg Lys Lys Gly Ala Asn Phe Asn Asn Leu Leu Asn Leu Arg Asn
            645                 650                 655

Asp Pro Pro Asn Asn Asn Asn Asn Asn Asn Asn Asn Asn Asn Asn Asn
            660                 665                 670

Met Asn Thr Phe Asn Asn Asn Met Asn Thr Phe Asn Asn Asn Asn Asn
            675                 680                 685

Asn Asn Asn Ser Asn Asn Asn His Ile Asn Asn Asn Ile Asn Asn Phe
            690                 695                 700

Asn Asn Asn Ser Arg Asn Thr Ile Pro His Asp Leu Ile Ser Ala Ala
705                 710                 715                 720

Thr Arg Asn Phe Asn Ile Gln Cys Gln His Lys Asn Ser Phe Ser Asp
            725                 730                 735

Glu Glu Glu Glu Leu Met Lys Val Ile Lys Lys Asn Ile Glu Ser Tyr
            740                 745                 750

Lys Met Asn Asn Ile Lys Asn Ile Leu Ile Ser Ser Val Phe Gly Arg
            755                 760                 765

Ile Lys Trp Leu Lys Ile Met Asn Glu Ser Pro His Ala Tyr Leu Tyr
            770                 775                 780

Gly His Ser Ile Val Lys Phe Gly Asn Lys Leu Tyr Met Phe Gly Gly
785                 790                 795                 800

Ser Asn Gly Lys Asn Lys Lys Ile Pro Phe Thr His Thr Leu Thr Phe
            805                 810                 815

Ser Leu Ile Tyr Tyr Asn Tyr Lys Leu Leu Pro Leu Ser Gly Asn Cys
            820                 825                 830
```

Pro Glu Glu Arg Glu Gly His Thr
                835                 840

<210> SEQ ID NO 19
<211> LENGTH: 397
<212> TYPE: PRT
<213> ORGANISM: Plasmodium falciparum

<400> SEQUENCE: 19

Met Met Arg Lys Leu Ala Ile Leu Ser Val Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
                35                  40                  45

Asn Glu Leu Glu Met Asn Tyr Tyr Gly Lys Gln Glu Asn Trp Tyr Ser
            50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
                100                 105                 110

Asn Ala Asn Pro Asn Val Asp Pro Asn Ala Asn Pro Asn Val Asp Pro
            115                 120                 125

Asn Ala Asn Pro Asn Ala Asn Pro Asn Ala Asn Pro Asn Ala Asn Pro
            130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
                180                 185                 190

Asn Ala Asn Pro Asn Val Asp Pro Asn Ala Asn Pro Asn Ala Asn Pro
                195                 200                 205

Asn Ala Asn Pro Asn Ala Asn Pro Asn Ala Asn Pro Asn Ala Asn Pro
            210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
                260                 265                 270

Asn Lys Asn Asn Gln Gly Asn Gly Gln Gly His Asn Met Pro Asn Asp
            275                 280                 285

Pro Asn Arg Asn Val Asp Glu Asn Ala Asn Ala Asn Ser Ala Val Lys
            290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
                340                 345                 350

Lys Pro Lys Asp Glu Leu Asp Tyr Ala Asn Asp Ile Glu Lys Lys Ile
            355                 360                 365

```
Cys Lys Met Glu Lys Cys Ser Ser Val Phe Asn Val Asn Ser Ser
            370             375             380

Ile Gly Leu Ile Met Val Leu Ser Phe Leu Phe Leu Asn
385             390             395

<210> SEQ ID NO 20
<211> LENGTH: 260
<212> TYPE: PRT
<213> ORGANISM: Plasmodium falciparum

<400> SEQUENCE: 20

Met Asn Ile Leu Cys Ile Leu Ser Tyr Ile Tyr Phe Phe Val Ile Phe
1               5                   10                  15

Tyr Ser Leu Asn Leu Asn Asn Lys Asn Glu Asn Phe Leu Val Val Arg
                20                  25                  30

Arg Leu Met Asn Asp Glu Lys Gly Glu Gly Gly Phe Thr Ser Lys Asn
            35                  40                  45

Lys Glu Asn Gly Asn Asn Asn Arg Asn Asn Glu Asn Glu Leu Lys Glu
        50                  55                  60

Glu Gly Ser Leu Pro Thr Lys Met Asn Glu Lys Asn Ser Asn Ser Ser
65                  70                  75                  80

Asp Lys Gln Pro Asn Asp Ile Ser His Asp Glu Ser Lys Ser Asn Ser
                85                  90                  95

Asn Asn Ser Gln Asn Ile Gln Lys Glu Pro Glu Lys Glu Asn Ser
            100                 105                 110

Asn Pro Asn Leu Asp Ser Ser Glu Asn Ser Ser Glu Ser Ala Thr Arg
            115                 120                 125

Ser Val Asp Ile Ser Glu His Asn Ser Asn Asn Pro Glu Thr Lys Glu
        130                 135                 140

Glu Asn Gly Glu Glu Pro Leu Asp Leu Glu Ile Asn Glu Asn Ala Glu
145                 150                 155                 160

Ile Gly Gln Glu Pro Pro Asn Arg Leu His Phe Asp Asn Val Asp Asp
                165                 170                 175

Glu Val Pro His Tyr Ser Ala Leu Arg Tyr Asn Lys Val Glu Lys Asn
            180                 185                 190

Val Thr Asp Glu Met Leu Leu Tyr Asn Met Met Ser Asp Gln Asn Arg
        195                 200                 205

Lys Ser Cys Ala Ile Asn Asn Gly Gly Cys Ser Asp Asp Gln Ile Cys
    210                 215                 220

Ile Asn Ile Asn Asn Ile Gly Val Lys Cys Ile Cys Lys Asp Gly Tyr
225                 230                 235                 240

Leu Leu Gly Thr Lys Cys Ile Ile Leu Asn Ser Tyr Ser Cys His Pro
                245                 250                 255

Phe Phe Ser Ile
            260
```

SERUM ANTIBODY ASSAY FOR DETERMINING PROTECTION FROM MALARIA, AND PRE-ERYTHROCYTIC SUBUNIT VACCINES

STATEMENT OF GOVERNMENT RIGHTS

This invention was made with government support under Small Business Innovation Research (SBIR) grant numbers 4R44AI055229-08, 3R44AI055229-06S1, and 5R44AI058499-05awarded by the National Institute of Allergy and Infectious Diseases (NIAID). The government has certain rights in this invention.

FIELD OF THE INVENTION

This invention relates generally to the field of malaria immunology and vaccinology.

REFERENCE TO A SEQUENCE LISTING SUBMITTED ELECTRONICALLY VIA EFS-WEB

The content of the electronically submitted sequence listing Name: "2602—0150002—Sequence Listing.txt"; Size: 46,736 bytes; and date of creation: Dec. 28, 2017) filed herewith the application is incorporated by reference in its entirety.

BACKGROUND OF THE INVENTION

Malaria control interventions, including insecticide-impregnated bed nets, insecticide spraying, and antimalarial drugs, have reduced malaria morbidity and mortality substantially (World Health Organization, World Malaria Report: 2013 (2013; www.who/int/malaria/publications/world_malaria_report_2013/report/en/). However, in 2010, despite these measures, there were an estimated 220 million clinical cases and 0.66 to 1.24 million deaths caused by malaria (World Health Organization, World Malaria Report: 2012, C. J. Murray et al., Lancet 379, 413-431 (2012)). A highly effective vaccine will be ideal for preventing malaria in individuals and eliminating malaria in defined geographic areas. It would optimally target the parasite at asymptomatic, pre-erythrocytic stages (C. V. Plowe et al., J. Infect. Dis. 200, 1646-1649 (2009), malERA Consultative Group on Vaccines, A research agenda for malaria eradication: vaccines. PLoS Med. 8, e1000398 (2011)). The World Health Organization malaria vaccine technology roadmap set a vaccine efficacy goal of 80% by 2025 (Malaria Vaccine Technology Roadmap, 2006; www.malariavaccine.org/files/Malaria_Vaccine_TRM_Final.pdf).

On the other hand, it has been known for over 40 years that high-level, enduring protective immunity can be provided by means of the bites of >1000 mosquitoes, infected with radiation attenuated *Plasmodium falciparum* (Pf) sporozoites (SPZ) (R. S. Nussenzweig, et al., Nature 216, 160-162 (1967); D. F. Clyde, et al., Am. J. Med. Sci. 266, 169-177 (1973); K. H. Rieckmann, et al., Trans. R. Soc. Trop. Med. Hyg. 68, 258-259 (1974); S. L. Hoffman, et al., J. Infect. Dis. 185, 1155-1164 (2002)). However, mosquito bite is not a useful way to administer sporozoites and as a practical matter, a whole sporozoite vaccine approach would require the capacity to manufacture live, aseptic, radiation-attenuated, purified, preserved PfSPZ as the immunogen of an injectable vaccine that meets regulatory standards (T. C. Luke, et al., J. Exp. Biol. 206, 3803-3808 (2003); S. L. Hoffman, et al., Hum. Vac. 6, 97-106 (2010); J. E. Epstein, et al., Science 334, 475-480 (2011)).

The first clinical trial of PfSPZ Vaccine, comprising the Pf NF54 strain of SPZ (T. Ponnudurai, et al., Trans. R. Soc. Trop. Med. Hyg. 76, 242-250 (1982)) was conducted in 80 immunologically naïve adults (J. E. Epstein, et al. (2011)). They received up to 6 doses of 1.35×105 SPZ subcutaneously (SC) or intradermally (ID). PfSPZ Vaccine proved safe and well-tolerated, but elicited low-level immune response and minimal protection. It was hypothesized that the limited efficacy was due to the inefficiency of the ID and SC routes of administration (J. E. Epstein, et al. (2011)). Parallel and subsequent studies in non-human primates (NHP) with the PfSPZ Vaccine showed that IV, but not SC, administration elicited potent and durable PfSPZ-specific T-cell responses in peripheral blood, and most notably in the liver (J. E. Epstein, et al. (2011)), the likely site of immune protection (S. L. Hoffman, et al., Nat. Med. 6, 1218-1219 (2000)).

Based on these results, a phase 1 clinical trial was conducted to determine safety, immunogenicity and protective efficacy of IV administration of PfSPZ Vaccine (R. A. Seder, R. A. et al., Science, 341:1359-1365 (2013)—incorporated herein by reference in its entirety). PfSPZ Vaccine-induced protection against Pf malaria was safe, well tolerated and highly protective when administered up to 6 times IV to 40 adults. Six of six adult subjects receiving 6.75×10$^5$ SPZ in 5 doses were protected as were 6 of 9 adult subjects who received 5.4×10$^5$ SPZ in 4 doses (R. A. Seder, et al. (2013)). Additional clinical trials have now been conducted and are discussed herein.

Malaria vaccine development requires an accurate measure of efficacy. The early signs, symptoms and pathology of malaria are identifiable and, if identified early, malaria can be treated. Controlled human malaria infection (CHMI) of immunized subjects is used to assess protection. While effective, CHMI is cumbersome and expensive, requiring participation of several clinicians, experts, and hospital facilities. An assay that is easy to administer and provides high sensitivity (identification of protected individuals) and specificity (identification of unprotected individuals) would therefore be very useful.

SUMMARY OF THE INVENTION

Provided herein are methods for determining a state of protective immunity against *P. falciparum*-induced malaria in a human subject. In some embodiments, the method comprises testing a human body fluid sample for antibodies that bind to at least one of a subset of determinants, each of which having a sequence that is at least 85%, 90% 95%, 99% or 100% identical to an amino acid sequence comprising a sequence chosen from the group consisting of SEQ ID NOs:11-18 or a sequence encoded by a corresponding nucleic acid sequence chosen from the group consisting of SEQ ID NOs:1-8 or antigenic fragments thereof, and determining whether the human body fluid sample comprises antibodies that are specifically immunoreactive to the Pf immunologic determinants, wherein immunoreactivity above a cutoff for at least one recombinant polypeptide indicates a state of protective immunity against *P. falciparum*-induced malaria in the subject.

Further provided are compositions or subunit vaccines comprising at least one Pf-specific polypeptide comprising an amino acid sequences at least 85%, 90%, 95%, 99% or 100% identical to an amino acid sequence comprising a sequence chosen from the group consisting of SEQ ID NOs:11-18 or a sequence encoded by a corresponding nucleic acid sequence chosen from the group consisting of SEQ ID NOs:1-8 or antigenic fragments thereof. Another embodiment is directed to compositions or vaccines comprising nucleic acid sequences chosen from the group consisting of SEQ ID NOs:1-8 or antigenic fragments thereof.

DESCRIPTION OF THE FIGURES

In FIG. 1A the columns represent paired samples of preimmunization and post-immunization/pre CHMI for each subject. In FIG. 1B the columns represent the Delta of pre-immunization and pre-CHMI for each subject. The column headers, shaded in a gradient of light gray to black, represent trial dosing groups as follows (left to right): 1) 4 doses of $7.5 \times 10^3$ PfSPZ; 2) 6 doses of $7.5 \times 10^3$ PfSPZ; 3) 4 doses of $30 \times 10^4$ PfSPZ; 4) 6 doses of $30 \times 10^4$ PfSPZ; 5) 4 doses of $1.35 \times 10^5$ PfSPZ; and 6) 5 doses of $1.35 \times 10^5$ PfSPZ. In FIG. 1A, pre-immunization and pre-CHMI time points are ordered in paired columns, and rows are sorted by mean reactivity across the study population. The range of responses is depicted in a gray scale gradient from light gray to black, as shown in the shading key. In FIG. 1B, Deltas for each study subject are shown in a two shade gradient scale, with dark black representing increasing antibodies from baseline and light gray representing lower antibodies than baseline.

FIG. 6A represents linear models fit to post-immunization/pre-CHMI antibody levels. FIG. 6B represents antibody Deltas between protected and unprotected individuals. FIG. 6C represents pre-immunization antibody levels.

FIG. 7A represents a linear model of the top 6 selected antibodies (corresponding to SEQ ID NOs:11-14 & 19-20). FIG. 7B represents the linear model with the addition of 4 proteins (corresponding to SEQ ID NOs:15-18) to the linear model of FIG. 7A. Solid lines represent ROC curves modeled on data from all subjects, and dashed lines represent ROC curves modeled on leave-on-out cross-validation (LOOCV).

DETAILED DESCRIPTION OF THE INVENTION

Definitions

Figure 1A:
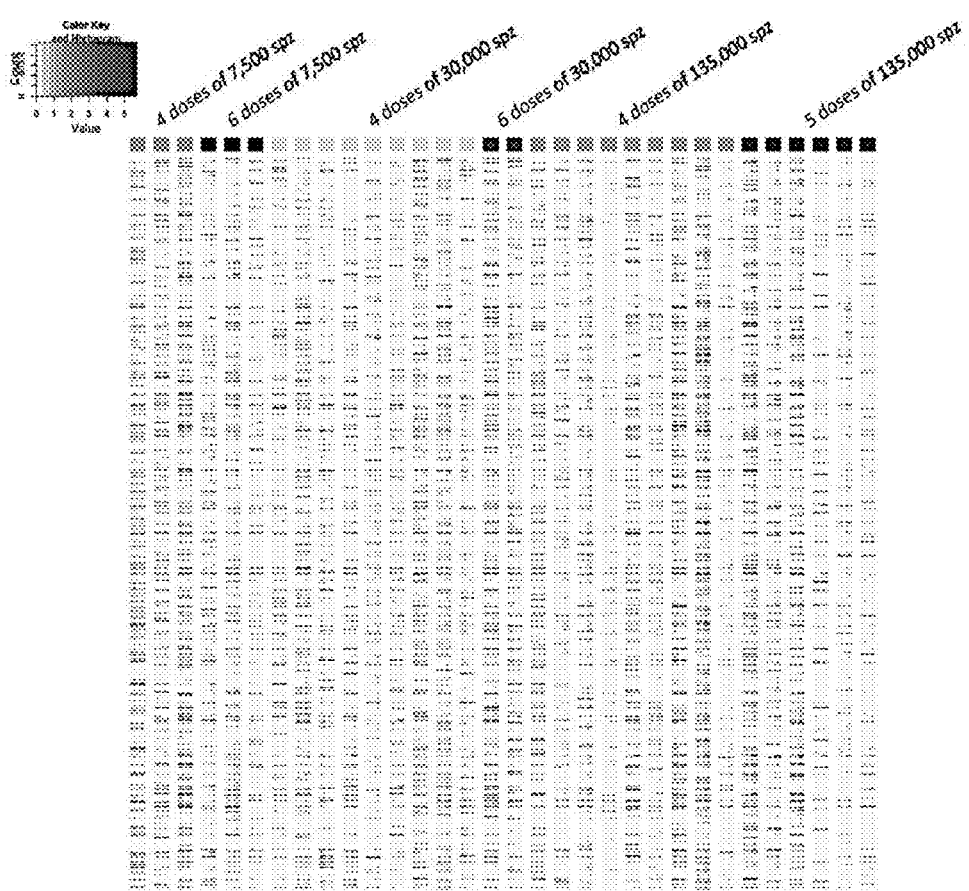
FIGS. 1A and 1B—Antibody reactivity profiles for pre- and post-immunization with PfSPZ using the high coverage Pf Whole Proteome Microarray (representing 91% of the Pf proteome). These heat maps represent the antibody profiles for 1,567 immunoreactive Pf proteins in PfSPZ-immunized volunteers. Rows represent individual antigens.

As used herein, "sensitivity" means the degree to which individuals with protective immunity are identified as positive. In the diagnostic embodiments described herein, sensitivity is the differential formation of complexes comprising an antigen binding molecule, e.g., antibodies in human body fluids, and a Pf immunologic determinant (positive reaction) in individuals that are determined to have protective immunity against malaria infection.

As used herein, "specificity" means the degree to which individuals lacking protective immunity are identified as negative. In the diagnostic embodiments described herein, specificity is the lack of differential formation of complexes comprising an antigen binding molecule, e.g., antibodies in human body fluids, and a Pf immunologic determinant (negative reaction) in individuals that are determined to lack protective immunity against malaria infection.

As used herein, "controlled human malaria infection," abbreviated "CHMI", means a controlled means of infecting individuals with malaria. After vaccination, CHMI serves to challenge subjects by exposing them to malaria-causing vectors and can be used to distinguish protected and unprotected individuals. CHMI can be accomplished, for example, by exposure of individuals to the bite of mosquitoes infected with *Plasmodium* or by direct inoculation of *Plasmodium* sporozoites.

As used herein, "Delta" or "antibody Delta" means the difference between the signals of pre-immunization and post-immunization immunoreactivities. In certain embodiments, Deltas are the difference between the intensities of measurement of certain Pf immunological determinants in human body fluid at a time after vaccination minus measurement of said Pf immunological determinants in human body fluid at a time before vaccination.

As used herein, "lacking" or to "lack" means being deficient in, or not having, a sufficient amount.

As used herein, "immunologic determinant" means an antigen, an antigenic epitope, or a sero-reactive peptide or protein.

As used herein, "differential reactivity" is the difference in the immunoreactivities of an immunologic determinant with an antigen binding molecule, e.g., antibodies in the human body fluids, of protected and unprotected subjects, wherein p-values are less than 0.05 as calculated using parametric and non-parametric hypothesis testing methods (e.g., two-tailed Student's t-test of unequal variance and Wilcoxon's rank-sum test).

As used herein, an immunologic determinant "encoded by a nucleic acid sequence" means those nucleic acid sequences are transcribed to mRNA, which is translated into the polypeptides which are the immunologic determinants.

As used herein, "seroprevalence" means the proportion of a population with positive reaction to a given immunoreactivity determination.

As used herein, "probing" a human body fluid means exposing that body fluid to one or more immunologic determinants and measuring the specific reactivity of the immunologic determinants to an antigen binding molecule, e.g., antibodies, in the human body fluid. As used herein, this measurement is referred to as an "immunoreactivity determination."

As used herein, a "human body fluid sample" refers to fluid that is removed from a subject, and can refer to fluid that is unprocessed or fluid that has been processed after removal. In some embodiment, the fluid sample is blood, saliva, excreta, body tissue or tissue fluids. In some embodiment, the fluid sample is derived from blood, saliva, excreta, body tissue or tissue fluids. In some embodiments, the human body fluid sample is serum or plasma.

As used herein, a "detection agent" is a molecule or a combination of molecules that specifically recognizes the complex formed by the binding of an immunologic determinant to an antigen binding molecule (e.g., an antibody).

As used herein, a "solid phase" refers to any structure for immobilization of immunological determinants, including but not limited to, glass and plastic (for example, polystyrene or polyvinylidene fluoride) including those treated with protein immobilizing agents such as poly-lysine, nitrocellulose or porous membranes. Solid phases may also include structures in liquid suspension, such as latex or metal microbeads, including those treated with protein immobilizing agents such as poly-lysine, nitrocellulose or porous membranes.

As used herein, "array" used in conjunction with solid phase refers to the immobilization of multiple immunological determinants such that each determinant is distinct from the others and a single human body fluid sample may be probed by the solid phase array in a single assay.

As used herein, the term "polypeptide" is intended to encompass a singular "polypeptide" as well as plural "polypeptides", and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide or antigenic fragment thereof of the invention may be of a size of about 15 or more, about 20 or more, about 25 or more, about 50 or more, about 75 or more, about 100 or more, about 200 or more, about 500 or more, about 1,000 or more amino acids. Polypeptides may have a defined three-dimensional structure, although they do not necessarily have such structure.

By an "isolated" polypeptide or a fragment, variant, or derivative thereof is intended a polypeptide that is not in its natural milieu. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides and immunogens of the present invention are fragments, derivatives, analogs, or variants of the foregoing polypeptides, and any combination thereof. The terms "fragment," "variant," "derivative," and "analog" polypeptides of the present application include any polypeptides that retain at least some of the properties of the corresponding polypeptide of the application. Fragments of polypeptides of the present invention include proteolytic fragments, as well as deletion fragments, in addition to specific antibody binding fragments discussed elsewhere herein. Variant polypeptides of the present application include fragments and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs." As used herein, a "derivative" of a polypeptide refers to a subject polypeptide having one or more residues chemically derivatized by reaction of a functional side group. Also included as "derivatives" are those peptides that contain one or more naturally occurring amino acid derivatives of the twenty standard amino acids. Derivatives of polypeptides of the present application may include polypeptides that have been altered so as to exhibit additional features not found on the reference polypeptide of the application.

The term "polynucleotide" is intended to encompass nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "lated" nucleic acid or polynucleotide is intended a nucleic acid molecule, DNA or RNA, that has been removed from its native environment. For example, a recombinant polynucleotide encoding polypeptide or antigenic fragment thereof contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a polypeptide or antigenic fragment, variant, or derivative thereof. Heterologous coding regions include without limitation specialized elements or motifs, such as a secretory signal peptide or a heterologous functional domain.

In certain embodiments, the polynucleotide or nucleic acid is DNA or RNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A "binding molecule" or "antigen binding molecule" of the present application refers in its broadest sense to a molecule that specifically binds an antigenic determinant of an antigen.

As used herein, "immunoreactive" means the binding of an immunologic determinant with an antigen binding molecule. When immunoreactivity occurs with immunologic determinants of human serum this is also referred to as "sero-reactive".

In certain embodiments, "specific immunoreactivity" or "specifically immunoreact" refers to direct binding to a particular polypeptide or Pf immunologic determinant.

As used herein, "immunodominant" means an antigenic determinant responsible in part for the major immune response in a host.

The term "cutoff", as used herein, refers to a threshold in the antibody levels, the antibody Delta measurement, or the predictive value. In some embodiments, the immunoreactivity of an immunological determinant above a certain cutoff is indicative of protective immunity in a subject. Cutoff refers to a single threshold for a single measurement (e.g., a Delta measurement) of a single immunological determinant (e.g., a Pf-specific polypeptide).

When combining cutoffs for multiple immunological determinants (e.g., to determine predictive value) one or more cutoff thresholds may be adjusted plus or minus 20% from the threshold stated for the threshold of a single determinant to optimize sensitivity and specificity. In some embodiments, the units used to describe the cutoffs herein are antibody Deltas, which are based on median fluorescence intensity (MFI) measurements from indirect antibody detection and are normalized before analysis ("Normalized MFI"), as described herein. Normalized MFI are translatable and scalable to optical density ("OD") measurements, such as those measured in ELISA assay. The scale of MFI for the methods described herein is approximately 0 to 60,000. Typical OD ranges for ELISA are from approximately 0.00 to 2.00 or 0.00 to 4.00, depending on the detection method. Antibody Deltas are translatable and scalable to OD ratios. In some embodiments, cutoffs for antibody Deltas are acquired by maximizing sensitivity and specificity on the receiver operating characteristic (ROC) curve at varying cutoffs.

The term "predictive value", as used herein, refers to the prediction estimated from regression models of one or more measurements of the immunological determinants. In some embodiments, the predictive value is estimated from logistic regression of antibody Delta measurements of one or more immunological determinants on the probability of being protected from *P. falciparum* malaria. In some embodiments, the predictive value is calculated by taking the sum of the products of logistic regression coefficients for each immunological determinant and the antibody Delta measurement for the corresponding immunological determinant (this is performed for each subject). In certain embodiments, the predictive value is used to estimate the performance characteristics of each combination of one or more immunological determinants in diagnosing protection from *P. falciparum* malaria.

The term "performance characteristics", as used herein, refers to a set of values estimated to determine the quality of an immunological determinant for determining if a vaccinated subject is protected from *P. falciparum* malaria. These estimates include "sensitivity", "specificity" and "area under the curve (AUC)" for the receiver operating characteristics (ROC) curve for predictive values or cutoff values.

In certain embodiments, as used herein, the term "about" means plus or minus 5% of the numerical value of the number with which it is being used. Therefore, about 85% means in the range of 80% to 90% as described herein.

In some embodiments, a binding molecule of the invention is an antibody or an antigen binding fragment thereof.

In some embodiments, an "antigen binding fragment" refers to one or more fragments of an antibody that retain the ability to specifically bind to an antigen (e.g., Pf antigen). Fragments of a full-length antibody can perform the antigen-binding function of an antibody. Examples of binding fragments include a Fab fragment, a F(ab')2 fragment, a Fd fragment; a Fv fragment, a single domain antibody fragment or dAb, and scFv.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

The portion of an antigen or polypeptide that specifically interacts with the antigen binding domain of an antibody is an "epitope," or an "antigenic determinant." An antigen or polypeptide may comprise a single epitope, but typically comprises at least two epitopes, and can include any number of epitopes, depending on the size, conformation, and type of antigen.

The terms "antigenic fragment" and "antibody binding fragment" are used interchangeably herein. An antigenic fragment, as used herein, is able to complex with the same antigen binding molecule, e.g., antibody in human body fluid, as the immunogenic determinant from which it is derived.

"Conferring protective immunity", as used herein, refers to providing to a population or a subject (i.e., an individual) the ability to generate an immune response to protect against a disease (e.g., malaria) caused by subsequent exposure to a pathogen (e.g., *Plasmodium falciparum*) such that the clinical manifestations, pathology, or symptoms of disease are reduced during subsequent exposure to the pathogen as compared to a non-treated host, or such that the rate at which infection, or clinical manifestations, pathology, or symptoms of disease appear within a population are reduced, as compared to a non-treated population.

"Immune response", as used herein, means a response in the recipient to the introduction of an immunogen (e.g., attenuated PfSPZ) generally characterized by, but not limited to, production of antibodies and/or T cells. Generally, an immune response may be a cellular response such as induction or activation of CD4+ T cells or CD8+ T cells specific for *Plasmodium*-species epitopes, a humoral response of increased production of *Plasmodium*-specific antibodies, or both cellular and humoral responses. With regard to a malaria vaccine, the immune response established by a vaccine comprising PfSPZ includes but is not limited to responses to proteins expressed by extracellular sporozoites or other stages of the parasite after the parasites have entered host cells, especially hepatocytes and mononuclear cells such as dendritic cells and/or components of said parasites. In certain embodiments, upon subsequent challenge by infectious organisms, the immune response prevents development of pathogenic parasites to the asexual erythrocytic stage that causes disease.

"Immunized", as used herein, means sufficiently vaccinated to achieve a protective immune response.

"Indication of Protection," as used herein, is a statistically significant profile. For example the increase in immunoreactivity to one or more of an identified subset of Pf-specific antibodies, in individuals that have been shown to be protected from Pf malaria by other means, for example by challenge using CHMI, and the absence of such profile in unprotected individuals. These Pf-specific antibodies may or may not be associated, in whole or in part with the mechanism of protection.

"Vaccine", as used herein, is a preparation comprising an immunogenic agent (also referred to herein as an immunogen) and a pharmaceutically acceptable diluent or carrier potentially in combination with excipient, adjuvant and/or additive or protectant. The immunogen may be comprised of a whole infectious agent or a molecular subset of the infectious agent (produced by the infectious agent, synthetically or recombinantly), e.g., a polypeptide, polynucleotide, or fragment thereof.

In certain embodiments, when the vaccine is administered to a subject, the immunogen stimulates an immune response that will, upon subsequent exposure to an infectious agent, protect the subject from illness or mitigate the pathology, symptoms or clinical manifestations caused by that agent. In some embodiments, a therapeutic (treatment) vaccine is given after infection and is intended to reduce or arrest disease progression. In some embodiments, preventive (prophylactic) vaccine is intended to prevent initial infection or reduce the rate or burden of the infection.

In some embodiments, agents used in vaccines against a parasitic disease such as malaria (e.g., *P. falciparum* vaccine) may be whole-killed (inactive) parasites, live-attenuated parasites (unable to fully progress through their life cycle), or purified or artificially manufactured molecules associated with the parasite—e.g., recombinant proteins, synthetic peptides, DNA plasmids, and recombinant viruses or bacteria expressing *Plasmodium* proteins. A vaccine may comprise sporozoites along with other components such as excipient, diluent, or carrier, for example, human serum albumin. A vaccine may further comprise preservative, adjuvant or other immune enhancer, or combinations thereof, as would be readily understood by those in the art As used herein, "inoculate" means to administer a clinically relevant dose of a vaccine, or multiple doses over time in a dosage regimen. In some embodiments, the vaccine is a *P. falciparum* vaccine, e.g., a *P. falciparum* whole parasite vaccine.

Diagnostics

In certain embodiments, the current application relates to detection of particular combinations of a subset of antibodies that can serve as an indicator of malaria protection, including protective immunity induced by vaccination, diagnostic assays, identification of subjects in need of further vaccination, and methods of treatment derived therefrom.

In certain embodiments, the current application relates to measured change in the immunoreactivity of a subset of antibodies from an initial state prior to vaccination to a subsequent state after vaccination. The difference serves as an indicator of malaria protection, including protective immunity induced by vaccination; and for the identification of subjects in need of further vaccination.

Certain embodiments of the application are directed to a method for determining a state of immunization or protective immunity against *P. falciparum*-induced malaria in a human subject said method comprising probing a human body fluid sample with at least one Pf immunologic determinant having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or antigenic fragments thereof, and determining whether said human body fluid sample comprises antibodies that are specifically immunoreactive to said Pf immunologic determinants, wherein specific immunoreactivity to said Pf immunologic determinants indicates protective immunity in said subject. In some embodiments, the method further comprises probing with a further Pf immunologic determinants having an amino acid sequence that is at least 85%, 90%, 95%, 99% or 100% identical to a polypeptide with an amino acid sequence of SEQ ID NO:19, SEQ ID NO:20, or antigenic fragments thereof, or encoded by a polynucleotide with the nucleic acid sequence of SEQ ID NO:9, SEQ ID NO:10, or antigenic fragments thereof.

In some embodiments, the method comprises probing with two or more Pf immunologic determinants each having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or antigenic fragments thereof.

In some embodiments, the method comprises probing with two or more Pf immunologic determinants each having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO: 19, or SEQ ID NO:20, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:10, or antigenic fragments thereof.

In some embodiments of the application a human body fluid sample comprising Pf-specific antibodies is probed with two or more Pf immunologic determinants each having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:19, or SEQ ID NO:20, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:9, or SEQ ID NO:10, or antigenic fragments thereof.

In some embodiments, the Pf immunologic determinant comprises DOC2, or a combination of DOC2/MSP5, DOC2/GSK3, DOC2/LRR9, DOC2/MSP5/GSK3, DOC2/MSP5/LRR9, DOC2/UNKPROT/LRR9, DOC2/GSK3/LRR9, DOC2/MSP5/GSK3/LRR9, CSP/DOC2, CSP/DOC2/MSP5, CSP/DOC2/GSK3, CSP/DOC2/LRR9, CSP/DOC2/MSP5/GSK3, or CSP/DOC2/MSP5/LLR9, or antigenic fragments thereof.

In some embodiments of the application the human body fluid is serum. In some embodiments the human body fluid is plasma.

In certain embodiments of the application Pf immunologic determinants are provided as an array affixed to a solid phase. In certain embodiments antibody immunoreactivity is determined by ELISA. In other embodiments, immunoreactivity is determined by WESTERN blot analysis. In other embodiments immunoreactivity is determined by rapid diagnostic tests such as lateral flow assays, chromatographic immunoassays, flow through nitrocellulose immunoassays and the like, in which antigens are affixed to a solid phase and contacted by sera, plasma or other human body fluid samples. These methods are known in the art. (See, e.g., B. D. Smith, et al., J. Infect. Dis. 204:825-831 (2011)). In other embodiments immunoreactivity is determined by immunoblot analysis.

In certain embodiments of this application the subject from whom body fluid is acquired was previously inoculated with a *P. falciparum*-specific prophylactic vaccine. In certain embodiments, the detection of certain Pf-specific antibodies from a subset of the Pf proteome in the body fluids of inoculated individuals is used to identify immunologic protection against Pf malaria.

Certain embodiments of this application are directed to a composition comprising at least one Pf-specific polypeptide each with an amino acid sequence being at least 85%, 90%, 95%, 99% or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide having the nucleic acid sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or antigenic fragments thereof.

In some embodiments, the composition comprises a further Pf immunologic determinant having an amino acid sequence that is at least 85%, 90%, 95%, 99% or 100% identical to a polypeptide with an amino acid sequence of SEQ ID NO:19, SEQ ID NO:20, or antigenic fragments thereof, or encoded by a polynucleotide with the nucleic acid sequence of SEQ ID NO:9, SEQ ID NO:10, or antigenic fragments thereof.

In some embodiments, the composition comprises two or more Pf immunologic determinants each having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO: 19, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or antigenic fragments thereof.

In some embodiments, the composition comprises two or more Pf immunologic determinants each having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:20, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:10, or antigenic fragments thereof.

In certain embodiments of this application the composition comprises two or more Pf specific polypeptides each having an amino acid sequence that is at least 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO: 19, or SEQ ID NO:20, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:9, or SEQ ID NO:10, or antigenic fragments thereof.

Certain embodiments of this application are directed to methods for identifying protective immunity against Pf-caused malaria in a human subject, wherein the protective immunity is identified by the detection of antibodies in a body fluid sample from said subject that is specific to at least one Pf-specific immunologic determinant affixed to one or more solid phases, wherein said method comprises:
  a. Applying said human body fluid sample to each solid phase, wherein each solid phase comprises at least one Pf-specific polypeptide each having an amino acid sequence that is at least 85%, 90%, 95%, 99% or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide having the nucleic acid sequence of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, or antigenic fragments thereof;
  b. Applying a detection agent that binds antibody-Pf determinants to the solid phase of (a); and
  c. Identifying protective immunity against Pf-induced malaria in said subject by detecting antibody binding to the polypeptides of (a).

In certain embodiments of this application, identification of protective immunity results from the detection of antibodies in a body fluid sample from a human subject that is specific to two or more Pf-specific immunologic determinants affixed to one or more solid phases, wherein the method comprises:
  a. Applying said human body fluid sample to each solid phase, wherein each solid phase comprises at least one Pf-specific polypeptide each having an amino acid sequence that is at least 85%, 90%, 95%, 99% or 100% identical to an amino acid sequence of SEQ ID NO:11, SEQ ID NO:12, SEQ ID NO:13, SEQ ID NO:14, SEQ ID NO:19, or SEQ ID NO:20, or antigenic fragments thereof, or encoded by a polynucleotide having the nucleic acid sequence of SEQ ID NO:1, SEQ ID NO:2, SEQ ID NO:3, SEQ ID NO:4, SEQ ID NO:9 or SEQ ID NO:10, or antigenic fragments thereof;
  b Applying a detection agent that binds antibody-Pf determinants to the solid phase of (a); and
  d. Identifying protective immunity against Pf-induced malaria in said subject by detecting antibody binding to the polypeptides of (a).

Pf Antigens

A subset of ten Pf antigens (SEQ ID NOs:1-10) were identified from the Pf proteome based on the immunoreactivity of sera taken after immunization as compared to the immunoreactivity of sera taken before immunization in individuals who were protected against CHMI as compared to those who were not protected. Of these 10, 6 Pf antigens (SEQ ID NO:11, SEQ ID NO:12, SEQ ID NO:13, SEQ ID NO:14, SEQ ID NO:19, SEQ ID NO:20) were selected for further analysis (Table 9). The LOOCV AUCs for the combination of these 6 antigens were 0.89 for pre-CHMI antibody levels and 0.82 for antibody Deltas, while addition of the other 4 antigens (SEQ ID NO:15, SEQ ID NO:16, SEQ ID NO:17, SEQ ID NO:18) resulted in LOOCV AUCs of 0.91 and 0.81, respectively.

Pf CSP (encoded by SEQ ID NO:9) and MSP5 (encoded by SEQ ID NO:10) were disclosed in PCT/US2014/053745, filed Sep. 2, 2014, which claims priority to U.S. 61/872,527, filed Aug. 30, 2013—filed by the same applicant as the present application.

GSK3 (SEQ ID NO:14), DOC2 (SEQ ID NO:13), LRR9 (SEQ ID NO:12) and PF3D7_1030200 (SEQ ID NO:10) are disclosed herein.

Pf GSK3 (SEQ ID NO:14) is a 51.6 kDa protein implicated in ATP-binding and phosphorylation (E. Droucheau, et al., Biochim. Biophys. Acta 1697, 181-96 (2004) and has been identified as part of the phosphoproteome (M. Treeck, et al., Cell Host Microbe, 10, 410-9 (2011); E. Lasonder, et al., J. Proteome Res., 11, 5323-37 (2012)). It has been identified as a potential target for drug therapies against Pf malaria (D. I. Osolodkin, et al., Parasitology, 138, 725-35 (2011); F.-J. Gamo, et al., Nature 465, 305-10 (2010)). Although it has been associated with Maurer's clefts in the intraerythrocytic cycle (M. Lanzer, et al., Int. J. Parasitol., 36, 23-36 (2006)), a high number of spectra and sequences have been observed by mass spectrometry in Pf salivary gland sporozoites (S. E. Lindner, S. E., et al., Mol. Cell. Proteomics 12, 1127-43 (2013)).

Pf DOC2 (SEQ ID NO:13) is a 221 kDa implicated in calcium-dependent phospholipid binding and entry into host cells and has been annotated as a component of cytoplasmic vesicles and host cell plasma membranes. DOC2 proteins were shown to be important for microneme secretion and had an effect on invasion, but not egress, when knocked down (A. Farrell, et al., Science 335, 218-21 (2012)), and it binds calcium when associated with membrane fractions (S. Jean, et al., Exp. Parasitol., 144, 91-5 (2014)).

Pf LRR9 (SEQ ID NO:12) is a 58.6 kDa with little annotation, has orthologs in non-human primate species of malaria, but not murine species, and has an annotated GO component as integral to membranes.

All three, GSK3, DOC2 and LRR9 have no predicted transmembrane domains, and they may be proteins that induce bystander antibody responses in parallel to alternative mechanism of sterile protection after PfSPZ vaccination.

The conserved protein, PF3D7_1030200 (SEQ ID NO:11), is a 51.3 kDa protein with 4 predicted transmembrane domains, GO component terms for cytoplasm, membrane and nucleus and annotated nucleotide binding function. It also has high levels of expression and multiple spectra by mass spectrometry in sporozoites (Lindner (2013)). Our data suggests that this uncharacterized sporozoite protein should be further investigated for functional immune responses.

The four additional antigens (SEQ ID NOs:15-18) include 3 uncharacterized conserved unknown function proteins and a C3HC4-type zinc finger motif (Table 8).

The conserved protein of unknown function, PF3D7_1438800 (SEQ ID NO:5), is an 84 kDa protein with no known transmembrane domains or signal peptides, but with annotated GO Component Terms for apicoplast, cytoplasm and plasma membranes. Gene expression of said sequence has been detected in the sporozoite and gametocyte stages.

The conserved protein of unknown function, PF3D7_0828100 (SEQ ID NO:16), is a 125 kDa protein with no known transmembrane domains or signal peptides and no annotated functions. Gene expression of said sequence has not been detected in the sporozoite stage to date and has been detected at the gametocyte stage. Our data suggests that this uncharacterized protein should be further investigated.

The putative C3HC4-type zinc finger protein, PF3D7_0728600 (SEQ ID NO:17), is a 253 kDa protein with no known transmembrane domains or signal peptides. Its annotated GO Function Terms include protein and zinc ion binding. Said gene sequence shows high gene expression in sporozoite and gametocyte stages. Our data suggests that this protein should be further investigated.

The conserved protein of unknown function, PF3D7_1468100 (SEQ ID NO:18), is a 296 kDa protein with no known transmembrane domains or signal peptides, but has a predicted GO Function Term for ATP binding and a predicted GO Component Term for cytoplasm and nucleus. Said protein has a multitude of spectra by mass spectrometry in sporozoites (Lindner (2013)).

Assay for Identifying Pf Proteins

As disclosed herein, plasma from 32 healthy U.S. volunteers immunized with PfSPZ and subjected to controlled human malaria infection (CHMI) was screened using partial and whole Plasmodium falciparum (N) proteome microarrays representing 4,805 unique genes, or approximately 91% of the Pf proteome. A total of 52 Pf proteins were identified as significant based on their immunogenic profile, association with sterile protection after CHMI and/or they had features associated with protection in generalizable combinatorial models.

In certain embodiments, the statistical methods used to determine immunogenicity ("Immunogenic Profile"): 1) paired T tests of antibody measurements before and after vaccination to compare means at each time point; 2) ordinary least squares (OLS) regression of PfSPZ dose on antibody Deltas to identify immunogenic dose responses; and 3) linear mixed effects regression (LMER) to model the effect of having been vaccinated, adjusted by PfSPZ dose, on antibody measurements, adding subject-level random effects to control for repeated measures.

In certain embodiments, the statistical methods used to determine association with sterile protection after CHMI ("Association with Protection"): 1) Estimation of the area under the ROC curve (AUC) for antibody measurements before CHMI and antibody Deltas specific to each protein in the classification of subjects as "protected" or "susceptible" as compared to the true diagnosis of protected or susceptible according to the gold standard of thick and thin blood smear by microscopy (as part of the CHMI protocol); 2) Wilcoxon's rank sum test of antibody measurements before CHMI and antibody Deltas to compare protected and susceptible group means.

In certain embodiments, the statistical methods used to determine association with protection in generalizable combinatorial models ("Combinatorial Analysis"): 1) fit generalized linear models of antibody measurements before vaccination and before CHMI and antibody Deltas on the probability of being protected (logistic regression) via penalized maximum likelihood using lasso and/or elastic net penalization, while restricting the models to combinations of a minimum of 2 antibody measurements and a maximum of 30 antibody measurements at a time—this is performed using data from all 32 study subjects; 2) perform Leave-One-Out Cross-Validation (LOOCV) by fitting generalized linear models of antibody measurements before vaccination and before CHMI and antibody Deltas on the probability of being protected (logistic regression) via penalized maximum likelihood using lasso and/or elastic net penalization, while restricting the models to combinations of a minimum of 2 antibody measurements and a maximum of 30 antibody measurements at a time—this is performed iteratively using data from 31 subjects ("Training Set"), varying the subject omitted so that each subject is excluded once; 3) Estimate a prediction value for each subject for each model generated, and estimate a prediction value for each "left-out" subject using the corresponding Training Set models; 4) Estimate the AUC of the best model per level of the model fit on all data (e.g., 2 combination models, 3 combination models . . . 30 combination models); 5) Estimate the mean AUC of all Training Set models per level of the model (e.g., 2 combination models, 3 combination models . . . 30 combination models); 5) Estimate the AUC of the prediction values from the "left-out" subjects per level of the model (e.g., 2 combination models, 3 combination models . . . 30 combination models); 6) Report the model parameters from the best model fit on all data corresponding to the level of the models with the highest "left-out" subject AUC.

In addition to the Pf circumsporozoite protein (CSP) and Pf merozoite protein 5 (MSP5) (described in PCT/US2014/053745), Pf glycogen synthase kinase 3 (GSK3), Pf double C2-like domain-containing protein (DOC2), Pf leucine-rich repeat protein (LRR9) and a conserved Pf protein of unknown function (PF3D7_1030200) were identified, both individually and in combination with each other and with CSP and/or MSP5, as effective in methods to demonstrate protection against Pf-induced malaria and as subunit vaccine targets.

Four additional proteins (conserved proteins of unknown function (PF3D7_1438800, PF3D7_0828100, and PF3D7_1468100) and zinc finger, C3HC4 type (PF3D7_0728600) were also identified.

Controlled Human Malaria Infection (CHMI)

The evaluation of the efficacy of malaria vaccines and treatments benefits from carefully monitoring results in early diagnosis of the onset of the signs, symptoms and pathology of malaria and its rapid and effective treatment thereafter. CHMI has become a method by which the efficacy of vaccination against malaria can be measured. In the trial described in Seder et al., Science, 341:1359-1365 (2013), CHMI was achieved by means of exposing subjects to Pf-infected mosquitoes that met standard infectivity criteria (K. E. Kester, et al., (2009); S. L. Hoffman, et al. (2002); J. D. Chulay, et al. Am. J. Trop. Med. Hyg. 35, 66-68 (1986); L. S. Rickman, et al. Am. J. Trop. Med. Hyg. 43, 441-445 (1990); K. E. Lyke, et al., PLoS ONE 5, e13490 (2010)) approximately 3 weeks after the last dose of PfSPZ Vaccine. The mosquitoes used were infected with Pf NF54 or a clone thereof. Subjects were monitored as outpatients for 7 days after CHMI and then admitted to the NIH Clinical Center for up to 11 consecutive nights or until diagnosis and cure of parasitemia was documented. Daily thick blood smears were performed, with additional smears performed when needed, based on clinical presentation. Treatment with chloroquine or atovaquone/proguanil was initiated when a thick blood smear had ≥2 Pf parasites in 0.5 µL blood, confirmed by an expert malaria microscopist. Subjects were discharged after two consecutive days with negative malaria smears or on post-CHMI day 18 if not parasitemic. Subjects were considered protected if smears were negative through day 28 post-CHMI. Quantitative PCR (qPCR) was performed to detect parasite DNA in blood.

In the clinical trial of Seder et al., antibody titers to CSP were measured. Two weeks after the final PfSPZ Vaccine administration, there was a relationship between the total dosage of vaccine and results of PfCSP ELISA. When used alone, measurement of serum antibodies to CSP exhibits 77% specificity with regard to distinguishing between protected and unprotected subjects, which is too low to be useful as a clinical alternative for CHMI. As disclosed herein, the multiplex reactivity of serum antibodies from human subjects directed to Pf antigens of CSP and MSP5 demonstrate better combined sensitivity and specificity. Furthermore, several of the newly identified subset of antigens, either alone or in combination show both high sensitivity and specificity (Table 1) making them an improved alternative to CHMI.

Cutoffs and Predictive Values

In certain embodiments, the predictive values for each study subject are estimated by logistic regression models of antibody Deltas for one or more immunological determinants on the probability of being protected against *P. falciparum* CHMI. In some embodiments, the predictive values are used to estimate the performance characteristics, also known as sensitivity analysis, for a given immunological determinant or a combination of immunological determinants. The resulting sensitivity, specificity and AUC calculations give an indication of the quality of said immunological determinants or combinations thereof. This can be interpreted that there exists an antibody Deltas cutoff for each immunological determinant that can be applied diagnose protection in vaccines with the same sensitivity and specificity. Cutoff values for individual immunological determinants can be estimated (e.g., as shown in Table 1). Cutoff values for multiple immunological determinant tests can vary according to a trade-off between the antibody Deltas for each immunological determinant tested. For example, increases in the antibody Deltas for Immunological Determinant A above the corresponding single-immunological determinant cutoff may reduce the required antibody Deltas level of Immunological Determinant B to a level below the corresponding single-immunological determinant cutoff. The range of acceptable cutoff values for a multi-immunological determinant test is determined by empirical testing.

In certain embodiments, the cutoff value for each immunological determinant is used as criteria for diagnosing the state of "protected" or "susceptible" for each subject. Antibody levels are measured as normalized median fluorescence intensity, or "normalized MFI" (or optical density ["OD"] or like measurements), for pre-immunization levels and post-immunization levels using human bodily fluids taken before and after immunization. Then antibody Deltas will be calculated by subtracting the pre-immunization normalized MFI values (or OD values or like) from the post-immunization normalized MFI values (or OD values or like). The cutoff values are used to score a subject as "protected" if the antibody Delta(s) exceed the cutoff values or "susceptible" if the antibody Delta(s) are below the cutoff values. In certain embodiments, when multiple cutoffs are used in combination as a multiple immunological determinant test, cutoff values may deviate from the stated optimal cutoff for a single immunological determinant by the empirically determined optimal cutoff for a given combination, deviating not more than 20% above or below the stated optimal cutoff, (e.g., about 1-20% above, about 5-20% above, about 10-20% above, about 15-20% above, about 1-15% above, about 1-10% above, or about 1-5% above).

TABLE 1

Optimal cutoff values for antibody Deltas (difference between pre-immunization and post-immunization immunoreactivities) against individual Pf antigens in discriminating protection and susceptibility to *P. falciparum* CHMI.

| Antigens | Cutoff * |
| --- | --- |
| CSP (PF3D7_0304600) | 4.90 |
| MSP5 (PF3D7_0206900.1) | 0.60 |
| Conserved/unknown protein (PF3D7_1030200)** | 0.67 |
| GSK3 (PF3D7_0312400) | 0.68 |
| DOC2 (PF3D7_1243900) | 1.36 |
| LRR9 (PF3D7_0906700) | 0.92 |

* Cutoff: the cutoff value is the antibody Deltas measurement estimated by maximizing sensitivity and specificity for determining protection against *P. falciparum* CHMI.
**As used herein, the conserved/unknown protein PF3D7_1030200 is referred to as "Conserved/unknown protein" or "UNKPROT".

TABLE 2

Performance characteristics of antibody Deltas (difference between pre-immunization and post-immunization immunoreactivities) against combinations of 6 Pf antigens in discriminating protection and susceptibility to CHMI.

| Antigens | Predictive Value * | Sensitivity | Specificity | False Positives | False Negatives |
| --- | --- | --- | --- | --- | --- |
| CSP (PF3D7_0304600) | 4.90 | 92% | 79% | 4 | 1 |
| MSP5 (PF3D7_0206900.1) | 0.60 | 85% | 79% | 4 | 2 |
| Conserved/unknown protein (PF3D7_1030200)** | 0.67 | 92% | 89% | 2 | 1 |
| GSK3 (PF3D7_0312400) | 0.68 | 85% | 89% | 2 | 2 |
| DOC2 (PF3D7_1243900) | 1.36 | 92% | 95% | 1 | 1 |
| LRR9 (PF3D7_0906700) | 0.92 | 85% | 84% | 3 | 2 |
| CSP, MSP5 | 5.13 | 85% | 89% | 2 | 2 |
| CSP, Conserved/unknown protein | 4.22 | 92% | 84% | 3 | 1 |
| CSP, GSK3 | 3.52 | 85% | 79% | 4 | 2 |
| CSP, DOC2 | 4.83 | 100% | 89% | 2 | 0 |
| CSP, LRR9 | 4.04 | 85% | 84% | 3 | 2 |
| MSP5, Conserved/unknown protein | 1.79 | 85% | 89% | 2 | 2 |
| MSP5, GSK3 | 1.30 | 85% | 89% | 2 | 2 |
| MSP5, DOC2 | 1.38 | 92% | 95% | 1 | 1 |
| MSP5, LRR9 | 1.30 | 85% | 89% | 2 | 2 |
| Conserved/unknown protein, GSK3 | 0.98 | 92% | 89% | 2 | 1 |
| Conserved/unknown protein, DOC2 | 2.27 | 92% | 89% | 2 | 1 |
| Conserved/unknown protein, LRR9 | 1.59 | 85% | 89% | 2 | 2 |
| GSK3, DOC2 | 1.68 | 92% | 95% | 1 | 1 |

TABLE 2-continued

Performance characteristics of antibody Deltas (difference between pre-immunization and post-immunization immunoreactivities) against combinations of 6 Pf antigens in discriminating protection and susceptibility to CHMI.

| Antigens | Predictive Value * | Sensitivity | Specificity | False Positives | False Negatives |
|---|---|---|---|---|---|
| GSK3, LRR9 | 1.23 | 85% | 89% | 2 | 2 |
| DOC2, LRR9 | 1.93 | 92% | 95% | 1 | 1 |
| CSP, MSP5, Conserved/unknown protein | 4.83 | 85% | 89% | 2 | 2 |
| CSP, MSP5, GSK3 | 4.32 | 85% | 89% | 2 | 2 |
| CSP, MSP5, DOC2 | 4.83 | 100% | 89% | 2 | 0 |
| CSP, MSP5, LRR9 | 4.49 | 85% | 89% | 2 | 2 |
| CSP, Conserved/unknown protein, GSK3 | 3.47 | 85% | 84% | 3 | 2 |
| CSP, Conserved/unknown protein, DOC2 | 5.99 | 85% | 89% | 2 | 2 |
| CSP, Conserved/unknown protein, LRR9 | 4.03 | 85% | 84% | 3 | 2 |
| CSP, GSK3, DOC2 | 4.86 | 100% | 89% | 2 | 0 |
| CSP, GSK3, LRR9 | 4.13 | 92% | 84% | 3 | 1 |
| CSP, DOC2, LRR9 | 4.25 | 100% | 89% | 2 | 0 |
| MSP5, Conserved/unknown protein, GSK3 | 1.77 | 85% | 89% | 2 | 2 |
| MSP5, Conserved/unknown protein, DOC2 | 2.25 | 92% | 89% | 2 | 1 |
| MSP5, Conserved/unknown protein, LRR9 | 2.52 | 85% | 89% | 2 | 2 |
| MSP5, GSK3, DOC2 | 1.66 | 92% | 95% | 1 | 1 |
| MSP5, GSK3, LRR9 | 1.24 | 85% | 89% | 2 | 2 |
| MSP5, DOC2, LRR9 | 1.94 | 92% | 95% | 1 | 1 |
| Conserved/unknown protein, GSK3, DOC2 | 2.29 | 92% | 89% | 2 | 1 |
| Conserved/unknown protein, GSK3, LRR9 | 1.10 | 92% | 84% | 3 | 1 |
| Conserved/unknown protein, DOC2, LRR9 | 2.33 | 92% | 95% | 1 | 1 |
| GSK3, DOC2, LRR9 | 1.94 | 92% | 95% | 1 | 1 |
| CSP, MSP5, Conserved/unknown protein, GSK3 | 4.52 | 85% | 89% | 2 | 2 |
| CSP, MSP5, Conserved/unknown protein, DOC2 | 5.91 | 85% | 89% | 2 | 2 |
| CSP, MSP5, Conserved/unknown protein, LRR9 | 4.35 | 85% | 89% | 2 | 2 |
| CSP, MSP5, GSK3, DOC2 | 4.86 | 100% | 89% | 2 | 0 |
| CSP, MSP5, GSK3, LRR9 | 4.71 | 92% | 89% | 2 | 1 |
| CSP, MSP5, DOC2, LRR9 | 4.34 | 100% | 89% | 2 | 0 |
| CSP, Conserved/unknown protein, GSK3, DOC2 | 6.25 | 85% | 89% | 2 | 2 |
| CSP, Conserved/unknown protein, GSK3, LRR9 | 4.09 | 92% | 84% | 3 | 1 |
| CSP, Conserved/unknown protein, DOC2, LRR9 | 5.38 | 85% | 89% | 2 | 2 |
| CSP, GSK3, DOC2, LRR9 | 5.78 | 92% | 89% | 2 | 1 |
| MSP5, Conserved/unknown protein, GSK3, DOC2 | 2.27 | 92% | 89% | 2 | 1 |
| MSP5, Conserved/unknown protein, GSK3, LRR9 | 2.35 | 85% | 89% | 2 | 2 |
| MSP5, Conserved/unknown protein, DOC2, LRR9 | 2.29 | 92% | 89% | 2 | 1 |
| MSP5, GSK3, DOC2, LRR9 | 1.88 | 92% | 95% | 1 | 1 |
| Conserved/unknown protein, GSK3, DOC2, LRR9 | 2.33 | 92% | 89% | 2 | 1 |
| CSP, MSP5, Conserved/unknown protein, GSK3, DOC2 | 6.21 | 85% | 89% | 2 | 2 |
| CSP, MSP5, Conserved/unknown protein, GSK3, LRR9 | 5.32 | 85% | 89% | 2 | 2 |
| CSP, MSP5, Conserved/unknown protein, DOC2, LRR9 | 5.39 | 85% | 89% | 2 | 2 |
| CSP, MSP5, GSK3, DOC2, LRR9 | 5.75 | 92% | 89% | 2 | 1 |
| CSP, Conserved/unknown protein, GSK3, DOC2, LRR9 | 5.66 | 92% | 89% | 2 | 1 |
| MSP5, Conserved/unknown protein, GSK3, DOC2, LRR9 | 2.28 | 92% | 89% | 2 | 1 |
| CSP, MSP5, Conserved/unknown protein, GSK3, DOC2, LRR9 | 5.60 | 92% | 89% | 2 | 1 |

* Predictive Value: The predictive value displayed is the optimal logistic regression prediction ("predictive value") for maximizing sensitivity and specificity performance characteristics in determining protection against *P. falciparum* malaria.
**As used herein, the conserved/unknown protein PF3D7_1030200 is referred to as "Conserved/unknown protein" or "UNKPROT".

As shown in Table 2, 9 combinations (DOC2, DOC2/MSP5, DOC2/GSK3, DOC2/LRR9, DOC2/MSP5/GSK3, DOC2/MSP5/LRR9, DOC2/UNKPROT/LRR9, DOC2/GSK3/LRR9, DOC2/MSP5/GSK3/LRR9) demonstrate 92% sensitivity combined with 95% specificity and having no more than 1 false positive and 1 false negative out of the 32 individuals assayed by CHMI. Six combinations (CSP/DOC2, CSP/DOC2/MSP5, CSP/DOC2/GSK3, CSP/DOC2/LRR9, CSP/DOC2/MSP5/GSK3, CSP/DOC2/MSP5/LLR9) demonstrate 100% sensitivity and 89% specificity and having 2 false positives and no false negatives out of the 32 individuals assayed by CHMI. In total, 15 combinations have no more than 2 combined false positives and negatives of the 32 individuals assayed.

In certain embodiments, new patients receiving vaccination have bodily fluid specimens taken before initial vaccination and after completion of a full vaccine regimen. A diagnostic test is then performed (e.g., ELISA-, Western- or alternative immunoblotting technique-based) generating pre-immunization and post-immunization antibody levels for each immunological determinant. The pre-immunization antibody levels are subtracted from the corresponding post-immunization levels to calculate antibody Deltas for each immunological determinant. Antibody Delta values are inserted into the corresponding formula for estimating predictive value (as shown in the Table 3). If a subject's predictive value exceeds that of the established cutoff criteria (Shown in Table 2), the subject is diagnosed as protected from *P. falciparum* malaria. If a subject's predictive value does not exceed the established cutoff criteria, then the patient is not diagnosed as protected or is diagnosed as not protected. In some embodiments, if the patient is not diagnosed as protected or is diagnosed as not protected, a further vaccination dose or other anti-malarial intervention can be administered.

TABLE 3

Predictive Value Formulas

| Antigen Combination | Predictive Value Formula** |
|---|---|
| CSP | 1.35 * CSP |
| MSP5 | 3.48 * MSP5 |
| UNKPROT | 2.3 * UNKPROT |
| GSK3 | 2.25 * GSK3 |
| DOC2 | 5.46 * DOC2 |
| LRR9 | 3.99 * LRR9 |
| CSP, MSP5 | 1.18 * CSP + 2.06 * MSP5 |
| CSP, UNKPROT | 1.04 * CSP + 0.718 * UNKPROT |
| CSP, GSK3 | 0.957 * CSP + 0.873 * GSK3 |
| CSP, DOC2 | 1.28 * CSP + 4.48 * DOC2 |
| CSP, LRR9 | 0.951 * CSP + 3.23 * LRR9 |
| MSP5, UNKPROT | 2.92 * MSP5 + 2.13 * UNKPROT |
| MSP5, GSK3 | 1.34 * MSP5 + 2.04 * GSK3 |
| MSP5, DOC2 | 0.367 * MSP5 + 5.27 * DOC2 |
| MSP5, LRR9 | 2.1 * MSP5 + 2.98 * LRR9 |
| UNKPROT, GSK3 | 1.22 * UNKPROT + 1.56 * GSK3 |
| UNKPROT, DOC2 | 1.51 * UNKPROT + 4.72 * DOC2 |
| UNKPROT, LRR9 | 1.36 * UNKPROT + 3.05 * LRR9 |
| GSK3, DOC2 | 1.19 * GSK3 + 3.86 * DOC2 |
| GSK3, LRR9 | 1.27 * GSK3 + 2.38 * LRR9 |
| DOC2, LRR9 | 4.04 * DOC2 + 2.19 * LRR9 |
| CSP, MSP5, UNKPROT | 0.868 * CSP + 2.44 * MSP5 + 0.876 * UNKPROT |
| CSP, MSP5, GSK3 | 0.986 * CSP + 1.71 * MSP5 + 0.576 * GSK3 |
| CSP, MSP5, DOC2 | 1.28 * CSP + −0.0307 * MSP5 + 4.49 * DOC2 |
| CSP, MSP5, LRR9 | 0.927 * CSP + 1.7 * MSP5 + 2.31 * LRR9 |
| CSP, UNKPROT, GSK3 | 0.856 * CSP + 0.432 * UNKPROT + 0.758 * GSK3 |
| CSP, UNKPROT, DOC2 | 1.11 * CSP + 0.503 * UNKPROT * 4.45 * DOC2 |
| CSP, UNKPROT, LRR9 | 0.933 * CSP + 0.0793 * UNKPROT + 3.2 * LRR9 |
| CSP, GSK3, DOC2 | 1.3 * CSP + −0.0427 * GSK3 * 4.52 * DOC2 |
| CSP, GSK3, LRR9 | 1.02 * CSP + −0.298 * GSK3 + 3.63 * LRR9 |
| CSP, DOC2, LRR9 | 1.03 * CSP + 3.67 * DOC2 + 1.77 * LRR9 |
| MSP5, UNKPROT, GSK3 | 2.43 * MSP5 + 1.56 * UNKPROT + 0.957 * GSK3 |
| MSP5, UNKPROT, DOC2 | 1.08 * MSP5 + 1.6 * UNKPROT + 4.22 * DOC2 |
| MSP5, UNKPROT, LRR9 | 2.59 * MSP5 + 1.49 * UNKPROT + 1.74 * LRR9 |
| MSP5, GSK3, DOC2 | −0.0717 * MSP5 + 1.19 * GSK3 + 3.88 * DOC2 |
| MSP5, GSK3, LRR9 | 1.28 * MSP5 + 1 * GSK3 + 2.09 * LRR9 |
| MSP5, DOC2, LRR9 | −0.0995 * MSP5 + 4.07 * DOC2 + 2.22 * LRR9 |
| UNKPROT, GSK3, DOC2 | 1.34 * UNKPROT + 0.443 * GSK3 + 4.28 * DOC2 |
| UNKPROT, GSK3, LRR9 | 1.09 * UNKPROT + 0.879 * GSK3 + 2.17 * LRR9 |
| UNKPROT, DOC2, LRR9 | 1.24 * UNKPROT + 4.04 * DOC2 + 1.73 * LRR9 |
| GSK3, DOC2, LRR9 | 0.394 * GSK3 + 3.79 * DOC2 + 1.82 * LRR9 |
| CSP, MSP5, UNKPROT, GSK3 | 0.821 * CSP + 2.27 * MSP5 + 0.776 * UNKPROT + 0.281 * GSK3 |
| CSP, MSP5, UNKPROT, DOC2 | 1.09 * CSP + 0.27 * MSP5 + 0.525 * UNKPROT + 4.34 * DOC2 |
| CSP, MSP5, UNKPROT, LRR9 | 0.857 * CSP + 1.92 * MSP5 + 0.311 * UNKPROT + 2.09 * LRR9 |
| CSP, MSP5, GSK3, DOC2 | 1.3 * CSP + 0.00652 * MSP5 + −0.0434 * GSK3 + 4.52 * DOC2 |
| CSP, MSP5, GSK3, LRR9 | 1.13 * CSP + 2.54 * MSP5 + −0.919 * GSK3 + 3.08 * LRR9 |
| CSP, MSP5, DOC2, LRR9 | 1.03 * CSP + −0.302 * MSP5 + 3.75 * DOC2 + 1.89 * LRR9 |
| CSP, UNKPROT, GSK3, DOC2 | 1.16 * CSP + 0.549 * UNKPROT + −0.194 * GSK3 + 4.61 * DOC2 |
| CSP, UNKPROT, GSK3, LRR9 | 1 * CSP + 0.0754 * UNKPROT + −0.297 * GSK3 + 3.61 * LRR9 |
| CSP, UNKPROT, DOC2, LRR9 | 0.968 * CSP + 0.309 * UNKPROT + 3.75 * DOC2 + 1.62 * LRR9 |
| CSP, GSK3, DOC2, LRR9 | 1.16 * CSP + −0.825 * GSK3 + 3.79 * DOC2 + 3.24 * LRR9 |
| MSP5, UNKPROT, GSK3, DOC2 | 0.91 * MSP5 + 1.45 * UNKPROT + 0.335 * GSK3 + 3.98 * DOC2 |
| MSP5, UNKPROT, GSK3, LRR9 | 2.38 * MSP5 + 1.41 * UNKPROT + 0.311 * GSK3 + 1.52 * LRR9 |
| MSP5, UNKPROT, DOC2, LRR9 | 0.703 * MSP5 + 1.3 * UNKPROT + 3.82 * DOC2 + 1.41 * LRR9 |
| MSP5, GSK3, DOC2, LRR9 | −0.245 * MSP5 + 0.409 * GSK3 + 3.86 * DOC2 + 1.89 * LRR9 |
| UNKPROT, GSK3, DOC2, LRR9 | 1.26 * UNKPROT + −0.0668 * GSK3 + 4.08 * DOC2 + 1.81 * LRR9 |
| CSP, MSP5, UNKPROT, GSK3, DOC2 | 1.15 * CSP + 0.525 * MSP5 + 0.61 * UNKPROT + −0.266 * GSK3 + 4.46 * DOC2 |
| CSP, MSP5, UNKPROT, GSK3, LRR9 | 1.05 * CSP + 2.83 * MSP5 + 0.393 * UNKPROT + −0.982 * GSK3 + 2.88 * LRR9 |
| CSP, MSP5, UNKPROT, DOC2, LRR9 | 0.97 * CSP + −0.0678 * MSP5 + 0.303 * UNKPROT + 3.76 * DOC2 + 1.65 * LRR9 |
| CSP, MSP5, GSK3, DOC2, LRR9 | 1.17 * CSP + 0.649 * MSP5 + −0.908 * GSK3 + 3.65 * DOC2 + 3.03 * LRR9 |
| CSP, UNKPROT, GSK3, DOC2, LRR9 | 1.09 * CSP + 0.342 * UNKPROT + −0.856 * GSK3 + 3.88 * DOC2 + 3.17 * LRR9 |
| MSP5, UNKPROT, GSK3, DOC2, LRR9 | 0.775 * MSP5 + 1.34 * UNKPROT + −0.141 * GSK3 + 3.88 * DOC2 + 1.52 * LRR9 |
| CSP, MSP5, UNKPROT, GSK3, DOC2, LRR9 | 1.1 * CSP + 1.03 * MSP5 + 0.424 * UNKPROT + −0.99 * GSK3 + 3.67 * DOC2 + 2.8 * LRR9 |

* Indicates multiplied by the antibody Delta of the corresponding determinant.
**In some embodiments, coefficient values in Table 3 can vary up to about 20%, about 15%, about 10%, about 5%, about 2%, about 1%, or about 0.5%.

In certain embodiments, assays have been developed in which immunological determinants described herein are affixed in a solid phase, for example, on a chip as a microarray as described herein upon which human body fluids are probed and specific antibodies to said immunological determinants are detected. In some embodiments these chips are provided to the clinician for use in assays of the sera from immunized individuals to look for reactivity patterns (specified combinations of immunodeterminants) indicating protective efficacy, for example as part of a clinical trial protocol, either in lieu of or in addition to CHMI. Additionally, these assays can be used to screen a population of subjects that have potentially been exposed to PfSPZ to determine those in need of vaccination as evidenced by their lacking the reactivity patterns (specified combinations of immunodeterminants) indicating protective efficacy. Probing of the sera of subjects is conducted and evaluated as described above. Alternatively, other immunodeterminative tests can be employed to determine seroreactivity to specific, identified multiplex Pf immunological determinants. Sera can be assessed for antibodies against PfSPZ by immunofluorescence assay (IFA) (J. E. Epstein, et al. (2011)) or to recombinant polypeptides having the sequence of SEQ ID NO:11-20 or encoded by SEQ ID NO:1-10 or antigenic fragments thereof or any Pf multiplex combinations thereof by enzyme linked immunosorbent assay (ELISA) as described (R. A. Seder, et al. (2013)). Alternatively, said immunological determinants may be fixed to solid phase membranes, for example, nitrocellulose as performed in standard Western blot, and immunoreactivity of the sera of subjects may be tested using lateral flow assays that detect antibodies bound to immunological determinants by protein A-celluloid gold complex to produce a visible diagnostic test line, as have been developed for diagnosis of HIV (or example, HIV 1/2 STAT-PAK® tests by ChemBio Diagnostic Systems, Inc., Medford, N.Y.) or Hepatitis C (for example, OraQuick® HCV test by OraSure Technologies, Inc., Bethlehem, Pa.).

Assays of humoral antibodies of vaccinated individuals that are easy to administer and have substantial sensitivity and specificity for identifying those individuals that are or are not protected will have great value, not only during the clinical testing of malaria vaccines, but also as a public health tool during post licensure vaccination campaigns. In addition, assays of the application that can be processed quickly and provide rapid results provide an advantage over current assays (e.g., CHMI) for protective immunity. The assays disclosed herein are easy to administer and provide high sensitivity (identification of protected individuals) and specificity (identification of unprotected individuals).

In some embodiments, the methods of the application are used to determine a satisfactory end point for vaccination. For example, the methods of the application can be used to determine whether immunization or protective immunity has been achieved and, optionally, whether further treatment is needed.

In one embodiment, the end point has been achieved and no further vaccine is administered to the subject when antibodies that specifically immunoreact with the specified combinations of immunodeterminants disclosed herein.

In another embodiment, the end point is not achieved and a subject is given a further dose of, or inoculated with a P. falciparum vaccine when antibodies that specifically immunoreact the specified combinations of immunodeterminants disclosed herein are not detected.

Certain embodiments are directed to a method for determining a state of protective immunity against P. falciparum-induced malaria in a human subject, comprising: (a) probing a human body fluid sample with at least one recombinant polypeptide comprising a sequence that is 85%, 90%, 95%, 99% or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide having a nucleic acid sequence chosen from SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or an antigenic fragment thereof; (b) determining whether said human body fluid sample comprises an antibody that is specifically immunoreactive to said at least one recombinant polypeptide, wherein positive specific immunoreactivity indicates a state of protective immunity in said subject.

Certain embodiments are directed to a method to assess the response to a malaria vaccine in a human subject comprising: (a) testing for the presence of an antibody binding to at least one recombinant polypeptide comprising a sequence that is at least 80%, 85%, 90%, 95%, 99% or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide having a nucleic acid sequence chosen from SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or an antigenic fragment thereof in a body fluid sample taken from the subject after a first dose of a malaria vaccine is administered to the subject; and (b) determining that the subject has protective immunity against P. falciparum-induced malaria if the presence of antibody binding to the at least one recombinant polypeptide from step (a) is detected.

Certain embodiments are directed to a method for determining a state of protective immunity against P. falciparum-induced malaria in a human subject, comprising: (a) probing a human body fluid sample with a polypeptide comprising DOC2 or an antigenic fragment thereof or DOC2 or an antigenic fragment thereof in combination with one of the following: (i) MSP5 or an antigenic fragment thereof, (ii) GSK3 or an antigenic fragment thereof, (iii) LRR9 or an antigenic fragment thereof, (iv) MSP5 or an antigenic fragment thereof and GSK3 or an antigenic fragment thereof, (v) MSP5 or an antigenic fragment thereof, LRR9 or an antigenic fragment thereof, (vi) UNKPROT or an antigenic fragment thereof and LRR9 or an antigenic fragment thereof, (vii) GSK3 or an antigenic fragment thereof and LRR9 or an antigenic fragment thereof, (viii) MSP5 or an antigenic fragment thereof, GSK3 or an antigenic fragment thereof, and LRR9 or an antigenic fragment thereof, (ix) CSP or an antigenic fragment thereof, (x) CSP or an antigenic fragment thereof and MSP5 or an antigenic fragment thereof, (xi) CSP or an antigenic fragment thereof and GSK3 or an antigenic fragment thereof, (xii) CSP or an antigenic fragment thereof and LRR9 or an antigenic fragment thereof, (xiii) CSP or an antigenic fragment thereof, MSP5 or an antigenic fragment thereof, and GSK3 or an antigenic fragment thereof, or (xiv) CSP or an antigenic fragment thereof, MSP5 or an antigenic fragment thereof, and LLR9 or an antigenic fragment thereof; (b) determining whether said human body fluid sample comprises an antibody that is specifically immunoreactive to said at least one recombinant polypeptide, wherein positive specific immunoreactivity indicates a state of protective immunity in said subject.

Certain embodiments are directed to a method to assess the response to a malaria vaccine in a human subject comprising: (a) testing for the presence of an antibody binding to at least one a polypeptide comprising DOC2 or an antigenic fragment thereof or DOC2 or an antigenic fragment thereof in combination with one of the following: (i) MSP5 or an antigenic fragment thereof, (ii) GSK3 or an antigenic fragment thereof, (iii) LRR9 or an antigenic fragment thereof, (iv) MSP5 or an antigenic fragment thereof and GSK3 or an antigenic fragment thereof, (v) MSP5 or an antigenic fragment thereof, LRR9 or an antigenic fragment thereof, (vi) UNKPROT or an antigenic fragment thereof and LRR9 or an antigenic fragment thereof, (vii) GSK3 or an antigenic fragment thereof and LRR9 or an antigenic fragment thereof, (viii) MSP5 or an antigenic fragment thereof, GSK3 or an antigenic fragment thereof, and LRR9 or an antigenic fragment thereof, (ix) CSP or an antigenic fragment thereof, (x) CSP or an antigenic fragment thereof and MSP5 or an antigenic fragment thereof, (xi) CSP or an antigenic fragment thereof and GSK3 or an antigenic fragment thereof, (xii) CSP or an antigenic fragment thereof and LRR9 or an antigenic fragment thereof, (xiii) CSP or an antigenic fragment thereof, MSP5 or an antigenic fragment thereof, and GSK3 or an antigenic fragment thereof, or (xiv) CSP or an antigenic fragment thereof, MSP5 or an antigenic fragment thereof, and LLR9 or an antigenic fragment thereof in a body fluid sample taken from the subject after a first dose of a malaria vaccine is administered to the subject; and (b) determining that the subject has protective immunity against *P. falciparium*-induced malaria if the presence of antibody binding to the at least one recombinant polypeptide from step (a) is detected.

Methods of Immunizing or Conferring Protective Immunity

Certain embodiments are directed to a method for immunizing or conferring protective immunity against *Plasmodium*-induced malaria, particularly Pf-induced malaria, to a subject comprising: (a) determining if an antibody that specifically immunoreacts with a Pf immunologic determinant comprising (i) a polypeptide having a sequence that is at least 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide selected from the group of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, an antigenic fragment thereof, or any combination thereof is in a body fluid sample from said subject; and (b) administering a *P. falciparum* vaccine to the subject if the body fluid sample lacks the antibody that specifically immunoreacts with the Pf immunologic determinant of (a).

Another embodiment is directed to a method for immunizing or conferring protective immunity against *Plasmodium*-induced malaria, particularly Pf-induced malaria, to a subject, wherein the method comprises: (a) determining if an antibody in a body fluid sample from said subject specifically immunoreacts with a Pf immunologic determinant comprising a polypeptide having a sequence that is at least 80%, 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide selected from the group of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, an antigenic fragment thereof, or any combination thereof; (b) administering a *P. falciparum* vaccine to the subject having a sample determined to lack immunoreactivity in (a).

Another embodiment is directed to a method of immunizing or conferring protective immunity against *Plasmodium*-induced malaria, particularly Pf-induced malaria, to a subject lacking an antibody that specifically immunoreacts with a Pf immunologic determinant, comprising administering a *P. falciparum* vaccine to the subject, wherein the Pf immunologic determinant comprises a polypeptide comprising a sequence that is at least 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide having a nucleic acid sequence chosen from the group of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, an antigenic fragment thereof, or any combination thereof.

Another embodiment is directed to a method for treating a subject lacking protective immunity against *Plasmodium*-induced malaria, particularly Pf-induced malaria, after being inoculated with a *P. falciparum* vaccine comprising: (a) inoculating a subject with a *P. falciparum* vaccine; (b) determining if an antibody in a body fluid sample from the subject specifically immunoreacts with a Pf immunologic determinant comprising a polypeptide comprising a sequence that is at least 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide selected from the group of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, an antigenic fragment thereof, or any combination thereof and (c) administering a dose of the *P. falciparum* vaccine to the subject if the sample lacks an antibody that specifically immunoreacts with the Pf immunologic determinant of (b).

In some embodiments, the Pf immunologic determinant comprises DOC2, or a combination of DOC2/MSP5, DOC2/GSK3, DOC2/LRR9, DOC2/MSP5/GSK3, DOC2/MSP5/LRR9, DOC2/UNKPROT/LRR9, DOC2/GSK3/LRR9, DOC2/MSP5/GSK3/LRR9, CSP/DOC2, CSP/DOC2/MSP5, CSP/DOC2/GSK3, CSP/DOC2/LRR9, CSP/DOC2/MSP5/GSK3, or CSP/DOC2/MSP5/LLR9, or antigenic fragments thereof.

In some embodiments, the sensitivity of the Pf immunological determinant is at least 89%, 90%, 91%, 92%, 93%, 94%, 95%, 96%, 97%, 98%, 99%, or 100%.

In some embodiments, the specificity of the Pf immunological determinant is at least 89%, 90%, 91%, 92%, 93%, 94%, 95%, 96%, 97%, 98%, 99%, or 100%.

Certain embodiments are directed to a method for immunizing a subject against *Plasmodium*-induced malaria, particularly Pf-induced malaria, comprising: (a) determining if a body fluid sample from a subject comprises an antibody that specifically immunoreacts with at least one recombinant polypeptide having a sequence that is at least 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide chosen from SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or an antigenic fragment thereof; and (b) administering a *P. falciparum* vaccine to the subject if the sample lacks the antibody that specifically immunoreacts with the at least one polypeptide of (a).

Certain embodiments are directed to a method for immunizing a subject lacking an antibody that specifically immunoreacts with at least one Pf immunologic determinants, comprising administering a *P. falciparum* vaccine to the subject, wherein the at least one Pf immunologic determinants is a recombinant polypeptide comprising a sequence that is at least 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or antigenic fragments thereof, or encoded by a polynucleotide having a nucleic acid sequence chosen from SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or an antigenic fragment thereof.

Certain embodiments are directed to a method for immunizing a subject against *Plasmodium*-induced malaria, particularly Pf-induced malaria, comprising: (a) determining if a body fluid sample from a subject comprises an antibody that specifically immunoreacts with a polypeptide comprising DOC2 or an antigenic fragment thereof or DOC2 or an antigenic fragment thereof in combination with one of the following: (i) MSP5 or an antigenic fragment thereof, (ii) GSK3 or an antigenic fragment thereof, (iii) LRR9 or an antigenic fragment thereof, (iv) MSP5 or an antigenic fragment thereof and GSK3 or an antigenic fragment thereof, (v) MSP5 or an antigenic fragment thereof, LRR9 or an antigenic fragment thereof, (vi) UNKPROT or an antigenic fragment thereof and LRR9 or an antigenic fragment thereof, (vii) GSK3 or an antigenic fragment thereof and LRR9 or an antigenic fragment thereof, (viii) MSP5 or an antigenic fragment thereof, GSK3 or an antigenic fragment thereof, and LRR9 or an antigenic fragment thereof, (ix) CSP or an antigenic fragment thereof, (x) CSP or an antigenic fragment thereof and MSP5 or an antigenic fragment thereof, (xi) CSP or an antigenic fragment thereof and GSK3 or an antigenic fragment thereof, (xii) CSP or an antigenic fragment thereof and LRR9 or an antigenic fragment thereof, (xiii) CSP or an antigenic fragment thereof, MSP5 or an antigenic fragment thereof, and GSK3 or an antigenic fragment thereof, or (xiv) CSP or an antigenic fragment thereof, MSP5 or an antigenic fragment thereof, and LLR9 or an antigenic fragment thereof and (b) administering a *P. falciparum* vaccine to the subject if the sample lacks the antibody that specifically immunoreacts with the at least one polypeptide of (a).

Certain embodiments are directed to a method for immunizing a subject lacking an antibody that specifically immunoreacts with at least one Pf immunologic determinant, comprising administering a *P. falciparum* vaccine to the subject, wherein the at least one Pf immunologic determinant is DOC2 or an antigenic fragment thereof or DOC2 or an antigenic fragment thereof in combination with one of the following: (i) MSP5 or an antigenic fragment thereof, (ii) GSK3 or an antigenic fragment thereof, (iii) LRR9 or an antigenic fragment thereof, (iv) MSP5 or an antigenic fragment thereof and GSK3 or an antigenic fragment thereof, (v) MSP5 or an antigenic fragment thereof, LRR9 or an antigenic fragment thereof, (vi) UNKPROT or an antigenic fragment thereof and LRR9 or an antigenic fragment thereof, (vii) GSK3 or an antigenic fragment thereof and LRR9 or an antigenic fragment thereof, (viii) MSP5 or an antigenic fragment thereof, GSK3 or an antigenic fragment thereof, and LRR9 or an antigenic fragment thereof, (ix) CSP or an antigenic fragment thereof, (x) CSP or an antigenic fragment thereof and MSP5 or an antigenic fragment thereof, (xi) CSP or an antigenic fragment thereof and GSK3 or an antigenic fragment thereof, (xii) CSP or an antigenic fragment thereof and LRR9 or an antigenic fragment thereof, (xiii) CSP or an antigenic fragment thereof, MSP5 or an antigenic fragment thereof, and GSK3 or an antigenic fragment thereof, or (xiv) CSP or an antigenic fragment thereof, MSP5 or an antigenic fragment thereof, and LLR9 or an antigenic fragment thereof.

Vaccine Compositions

Pharmaceutical compositions comprising polypeptides having the amino acid sequences disclosed herein, and methods of using these compositions as the immunogen in prophylactic vaccines to prevent malaria are provided. These compositions and methods are useful to generate immune responses and provide partial, enhanced, or full protection in human and other mammalian subjects not previously exposed to a malaria-causing pathogen, or exposed, but not fully protected. These compositions and vaccines are similarly useful to reduce the chance of developing a disease-producing infection from parasites that causes malaria, including species of *Plasmodium* having a human host range, particularly *P. falciparum, P. vivax, P. ovale, P. malariae, P. knowlesi, P. coatneyi, P. cynomolgi, P. simium* and the like, and reduce the chance of becoming ill when one is infected, reduce the severity of the illness, such as fever, when one becomes infected, reduce the concentration of parasites in the infected person, or reduce mortality rates from malaria in populations exposed to malaria parasites. In many cases even partial protection or delay in the time it takes an immunized individual as compared to a non-immunized individual to become infected with the parasites or ill from infection is beneficial. Similarly, a vaccine treatment strategy that results in any of these benefits in about 30% of a population may have a significant impact on the health of a community and of the individuals residing in the community.

In certain embodiments, the application is directed to a composition comprising one, two, three, four or more Pf immunologic determinants each having an amino acid sequence that is at least 80%, 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO: 19, or SEQ ID NO:20, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, or antigenic fragments thereof.

In some embodiments of this application, the composition comprises two, three, four or more Pf specific polypeptides each having an amino acid sequence that is at least 80%, 85%, 90%, 95%, 99% or 100% identical to a polypeptide with an amino acid sequence of SEQ ID NO:11, SEQ ID NO:12, SEQ ID NO:13, SEQ ID NO:14, SEQ ID NO:19, or SEQ ID NO:20, or antigenic fragments thereof, or encoded by a polynucleotide with the nucleic acid sequence of SEQ ID NO:1, SEQ ID NO:2, SEQ ID NO:3, SEQ ID NO:4, SEQ ID NO:9, or SEQ ID NO:10, or antigenic fragments thereof.

In some embodiments, the composition comprises DOC2, or a combination of DOC2/MSP5, DOC2/GSK3, DOC2/LRR9, DOC2/MSP5/GSK3, DOC2/MSP5/LRR9, DOC2/UNKPROT/LRR9, DOC2/GSK3/LRR9, DOC2/MSP5/GSK3/LRR9, CSP/DOC2, CSP/DOC2/MSP5, CSP/DOC2/

GSK3, CSP/DOC2/LRR9, CSP/DOC2/MSP5/GSK3, or CSP/DOC2/MSP5/LLR9, or antigenic fragments thereof.

In some embodiments the vaccine comprises one or more recombinant or synthetic subunit vaccine components, including but not limited to a recombinant protein, or synthetic polypeptides comprising at least one of SEQ ID NO:11-20 or an antigenic fragment thereof.

In some embodiments the vaccine comprises a polynucleotide (e.g., DNA or RNA) encoding at least one of SEQ ID NO:1-10 or an antigenic fragment thereof. In some embodiments, the polynucleotide is functionally incorporated in a vector, recombinant virus, recombinant bacteria, or recombinant parasite.

It is known that there is cross reactivity among the orthologous immunogens of different species of *Plasmodium*, particularly among the *Plasmodium* species of human host range. Therefore, a vaccine comprising an immunogen derived from *P. falciparum* is expected to confer a degree of protection to malarias whose etiologies are Plasmodia of other human host range species, particularly *P. vivax, P. ovale, P. malariae*, and *P. knowlesi*.

Provided are methods for generation of an immune response and prevention of malaria in a subject. The methods comprise administering to the subject a vaccine, which has been prepared aseptically and comprises polypeptides or DNA having one or more of the amino acid sequences disclosed herein in an amount effective to generate an immune response or to prevent malaria.

The subject to which the vaccine is administered in accordance with these methods may be any human or other mammal, susceptible to infection with a malaria parasite. For such methods, administration can be via the alimentary tract, such as oral, or administration can be parenteral, including, but not limited to mucosal, intranasal, epidermal, cutaneous, intramuscular, subcutaneous, intradermal, submucosal, intravenous and the like. Moreover, the administration may be by continuous infusion or by single or multiple boluses as well as delivery mediated by microneedles.

The prevention and/or treatment of malaria may be readily ascertained by the skilled practitioner by means of evaluation of clinical or pathological manifestations associated with malarial infection, for example elevated temperature, headache, fatigue, coma, or percent of erythrocytes parasitized. Thus, according to the methods of the present invention, the subject shows improved or absent clinical signs, symptoms or pathological manifestations of malaria following administration of a vaccine comprising purified live attenuated *Plasmodium* sporozoites.

Effective and optimal doses and dosage ranges for vaccines and immunogens can be determined using methods known in the art. Guidance as to appropriate dosages to achieve an anti-malarial effect is provided from the exemplified assays disclosed herein. More specifically, results from the immunization pattern described herein and in cited references can be extrapolated by persons having skill in the requisite art to provide a test vaccination schedule. Volunteer subjects are inoculated with varying doses at scheduled intervals and test blood samples are evaluated for levels of protection against malaria upon subsequent challenge with infective parasites. Such results can be used to refine an optimized immunization dose and dosage regimen (schedule) for effective immunization of mammalian, specifically human, subjects. It is anticipated that optimized doses and dosage regimens will vary generally with the general body mass of the subject and infants and small children will require proportionally less immunogen than adults. Furthermore, optimized doses and dosage regimens vary depending on the mode of administration, with intra dermal, subcutaneous and intramuscular administration requiring more immunogen than intravenous administration. Methods of formulating pharmaceutical compositions and vaccines are well known to those of ordinary skill in the art (see, e.g., Remington, The Science and Practice of Pharmacy 21st Edition, Hendrickson, ed. (USIP: 2005)). Comprehended by the invention are vaccine compositions comprising the polypeptides disclosed herein, and in certain embodiments these polypeptides are integrated into vectors along with appropriate diluent and buffer. Diluents, commonly Phosphate Buffered Saline (PBS), or Normal Saline (NS), are of various buffer content pH and ionic strength. Such compositions may also include an excipient such as serum albumin, particularly human serum albumin. Serum albumin may be purified from naturally occurring sources such as human blood, or be produced by recombinant DNA or synthesis technologies. Such compositions may also include additives such as anti-oxidants e.g., ascorbic acid, sodium metabisulfite, and/or preservatives or cryopreservatives. Incorporation of the material into particulate preparations of polymeric compounds such as polylactic acid, polyglycolic acid, etc. or into liposomes may also be used. This may also include *Plasmodium*-related DNA vaccines or a recombinant virus, such as adenovirus, that express *Plasmodium*-related proteins, as a prime and purified, attenuated sporozoites vaccine as a boost, or vice versa. It may also include sequential or mixed immunization with attenuated *Plasmodium* species sporozoites and some form of erythrocytic stage parasites, including, killed and live attenuated. A vaccine complex comprising separate components may be referred to as a vaccine regimen, a prime/boost regimen, component vaccine, a component vaccine kit or a component vaccine package, comprising separate vaccine components. For example, a vaccine complex may comprise as a component, a vaccine comprising purified, aseptic, live attenuated sporozoites. The complex may additionally comprise one or more recombinant or synthetic subunit vaccine components, including but not limited to recombinant protein, synthetic polypeptide, DNA encoding these elements per se or functionally incorporated in recombinant virus, recombinant bacteria, or recombinant parasite. A vaccine component may also include aseptic attenuated axenic sporozoites that are allowed to develop to the early liver stage extracellularly. Toll-like receptor agonists may be included in the vaccine formulation or conjugated directly to the polypeptides to control and direct their immunogenicity.

Kits

Certain embodiments are directed to a kit for identifying a human subject lacking immunization or protective immunity against *P. falciparum*-induced malaria comprising, in one or more containers, (a) at least one recombinant polypeptide having a sequence that is at least 80%, 85%, 90%, 95%, 99%, or 100% identical to an amino acid sequence of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO: 20, or antigenic fragments thereof, or encoded by a polynucleotide comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, or an antigenic fragment thereof, wherein the at least one recombinant polypeptide of (a) are immobilized on one or more solid supports; and (b) an immunologic determinants-antibody detection reagent.

In some embodiments, the at least one recombinant polypeptide is DOC2, or a combination of DOC2/MSP5, DOC2/GSK3, DOC2/LRR9, DOC2/MSP5/GSK3, DOC2/MSP5/LRR9, DOC2/UNKPROT/LRR9, DOC2/GSK3/LRR9, DOC2/MSP5/GSK3/LRR9, CSP/DOC2, CSP/DOC2/MSP5, CSP/DOC2/GSK3, CSP/DOC2/LRR9, CSP/DOC2/MSP5/GSK3, or CSP/DOC2/MSP5/LLR9, or antigenic fragments thereof.

EXAMPLES

Example 1

A clinical trial testing the immunogenicity and efficacy of aseptic, radiation-attenuated, purified, cryopreserved sporozoites used as the immunogen in a vaccine formulation (Sanaria® PfSPZ Vaccine, provided by Sanaria Inc.), and administered by intravenous injection, resulted in 13 individuals that were protected against controlled human malaria infection (CHMI) and 19 that were not protected (Table 4). In the group receiving the highest dosage (675,000 total PfSPZ), 6 out of 6 individuals were protected; and the group receiving the next lower dosage (540,000 total PfSPZ) had 6 out of 9 protected (Seder et al., Science 2013).

TABLE 4

Protection efficacy

| PfSPZ per Dose | Doses | Total dosage of PfSPZ | # volunteers | # Protected | Protection % | Protection % Combined |
|---|---|---|---|---|---|---|
| 7500 (low) | 4 | 30000 | 3 | 0 | 0% | 0% |
|  | 6 | 45000 | 3 | 0 | 0% |  |
| 30000 (medium) | 4 | 120000 | 9 | 1 | 11% | 9% |
|  | 6 | 180000 | 2 | 0 | 0% |  |
| 135000 (high) | 4 | 540000 | 9 | 6 | 67% | 80% |
|  | 5 | 675000 | 6 | 6 | 100% |  |

The 5-dose (675000 SPZ) group in which all subjects were protected differed from other groups, e.g., these subjects received the highest overall dosage of SPZ and there was a 7-week interval between the fourth and fifth doses. The sera from both protect and unprotected individuals was used to identify immunogenic determinants.

Example 2

*P. falciparum* Proteome Microarray Chip Fabrication

*P. falciparum* (Pf) genes, representing 91% of the Pf proteome, were selected and cloned into the *Escherichia coli* (*E. coli*) expression vector pXT7. Included among these genes were those corresponding to SEQ ID NOs:1-10. Custom polymerase chain reaction (PCR) primers comprising 20-bp gene-specific sequences with 33-bp adapter sequences were used to amplify target amplicons from Pf genomic DNA. The adapter sequences, which flank the target amplicons, are homologous to the adapter sequences at the ends of the linearized T7 expression vector pXT7 into which they were cloned. The homology allows the amplified PCR products to be cloned into the expression vector by in vivo homologous recombination in competent DH5a cells. The resulting clone mixtures were then verified by PCR using sequence specific primers and subsequently sequenced. For proteins microarray chip fabrication, Pf proteins were expressed in *E. coli*-based cell-free in vitro transcription and translation (IVTT) system (Rapid Translation System 100 High Yield [RTS 100 HY] kits from 5 PRIME, Gaithersburg, MD) according to the manufacturer's instructions. Expressed Pf proteins were then printed onto nitrocellulose-coated glass AVID slides (Grace Bio-Labs, Inc., Bend, Oreg.) using an OmniGrid Accent microarray printer (DigiLab, Inc., Marlborough, Mass.). Fabricated proteins microarray chips were QC using monoclonal anti-polyhistidine (clone His-1; Sigma-Aldrich, St. Louis, Mo.) and anti-hemagglutinin (clone 3F10; Roche, Indianapolis, Ind.) antibodies.

Proteome Microchip Design

Two types of Pf proteome microarrays were used: a down-selected microarray of highly reactive Pf proteins (Pf1000), and a whole proteome microarray with 91% coverage of the Pf proteome (PfWPM). Each Pf1000 chip contained 1,087 Pf peptide fragments representing proteins from 861 unique Pf genes, 32 IgG positive control spots and 16 spotted IVTT reactions without Pf ORFs (IVTT controls). For each Pf1000 chip, 8 replicates were printed per microarray slide on 8 nitrocellulose "pads". PfWPM chips contained 7,455 Pf peptide fragments, representing proteins from 4,805 unique genes, 302 IgG positive control spots and 192 IVTT control spots. For each PfWPM chip, 3 replicates were printed per microarray slide on 3 pads. IgG positive control spots were included as an assay control, while IVTT control spots were included as a sample-level normalization factor.

Serum Probing Using *P. falciparum* Protein Microarray

Sera from human trial subjects was collected no sooner than 7 days after administration of the last dose of the vaccine regimen, preferably within 10-14 days after administration of the last dose. Plasma samples were diluted 1:100 in a 3mg/mL *E. coli* lysate solution in protein arraying buffer (Maine Manufacturing, Sanford, Me., USA) and incubated at room temperature for 30 min. Chips were rehydrated in blocking buffer for 30 min. Blocking buffer was removed, and chips were probed with pre-incubated serum samples using sealed, fitted slide chambers to ensure no cross-contamination of sample between pads. Chips were incubated overnight at 4° C. with agitation. Chips were washed five times with TBS-0.05% Tween 20, followed by incubation with biotin-conjugated goat anti-human IgG (Jackson ImmunoResearch, West Grove, Pa., USA) diluted 1:200 in blocking buffer at room temperature. Chips were washed three times with TBS-0.05% Tween 20, followed by incubation with streptavidin-conjugated SureLight P-3 (Columbia Biosciences, Frederick, Md., USA) at room temperature protected from light. Chips were washed three times with TBS-0.05% Tween 20, three times with TBS, and once with water. Chips were air dried by centrifugation at 1,000×g for 4 min and scanned on a ScanArray Express HT spectral scanner (Perkin-Elmer, Waltham, Mass., USA), and spot and background intensities were measured using an annotated grid file (.GAL). Data were exported in Microsoft Excel.

Protein Microarray Data Analysis

Raw spot and local background fluorescence intensities, spot annotations and sample phenotypes were imported and merged in the R statistical environment, where all subsequent procedures were performed (www.r-project.org). Foreground spot intensities were adjusted by local background by subtraction, and negative values were converted to 1. Next, all foreground values were transformed using the base 2 logarithm (Log2). The dataset was normalized to remove systematic effects by subtracting the median signal intensity of the IVTT controls for each sample. Since the IVTT control spots carry the chip, sample and batch-level systematic effects, but also antibody background activity to the IVTT system, this procedure normalizes the data and provides a relative measure of the specific antibody binding to the non-specific antibody binding to the IVTT controls (a.k.a. background). With the normalized data, a value of 0.0 means that the intensity is no different than the background, and a value of 1.0 indicates a doubling with respect to background.

A seropositivity threshold was established as twice the IVTT background, or a normalized signal of 1.0, which was more conservative than two or three standard deviations above the mean of the IVTT controls. Reactive antigens were defined as those that had seropositive responses in at least 10% of the study population, or 4 subjects, at either pre-immunization or pre-CHMI time points. Non-reactive antigens were filtered before group comparisons were performed.

Figure 1B:
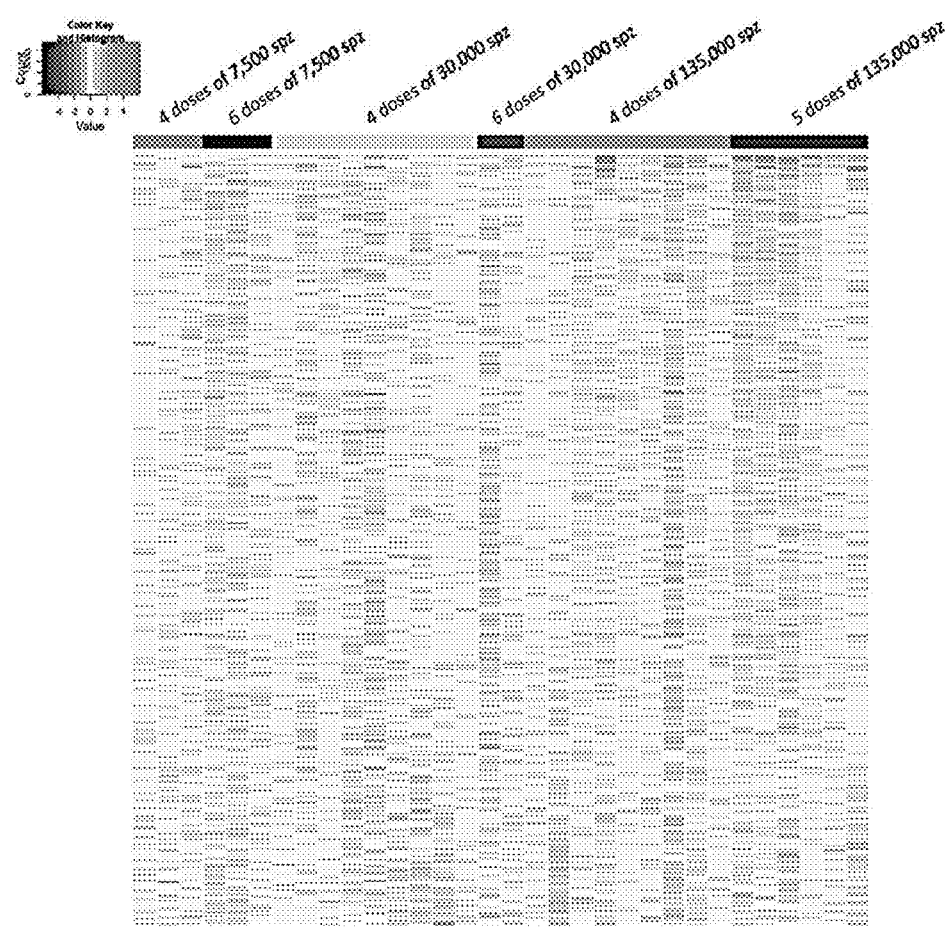

A high coverage, Pf Whole Proteome Microarray (Pf-WPM) was used to test antibodies against a total of 7,455 whole or partial Pf proteins, representing proteins from 4,805 unique genes, or approximately 91% of the Pf proteome. Among those antigens, 1,567 were identified as immunoreactive in PfSPZ-immunized volunteers, according to our reactivity criteria of 10% seroprevalence for a given antigen. The reactivity profile of all subjects at pre-immunization and post-immunization (pre-CHMI) time points are shown in FIG. 1A, and difference between pre- and post-immunization, or "Deltas" in FIG. 1B.

Figure 2:
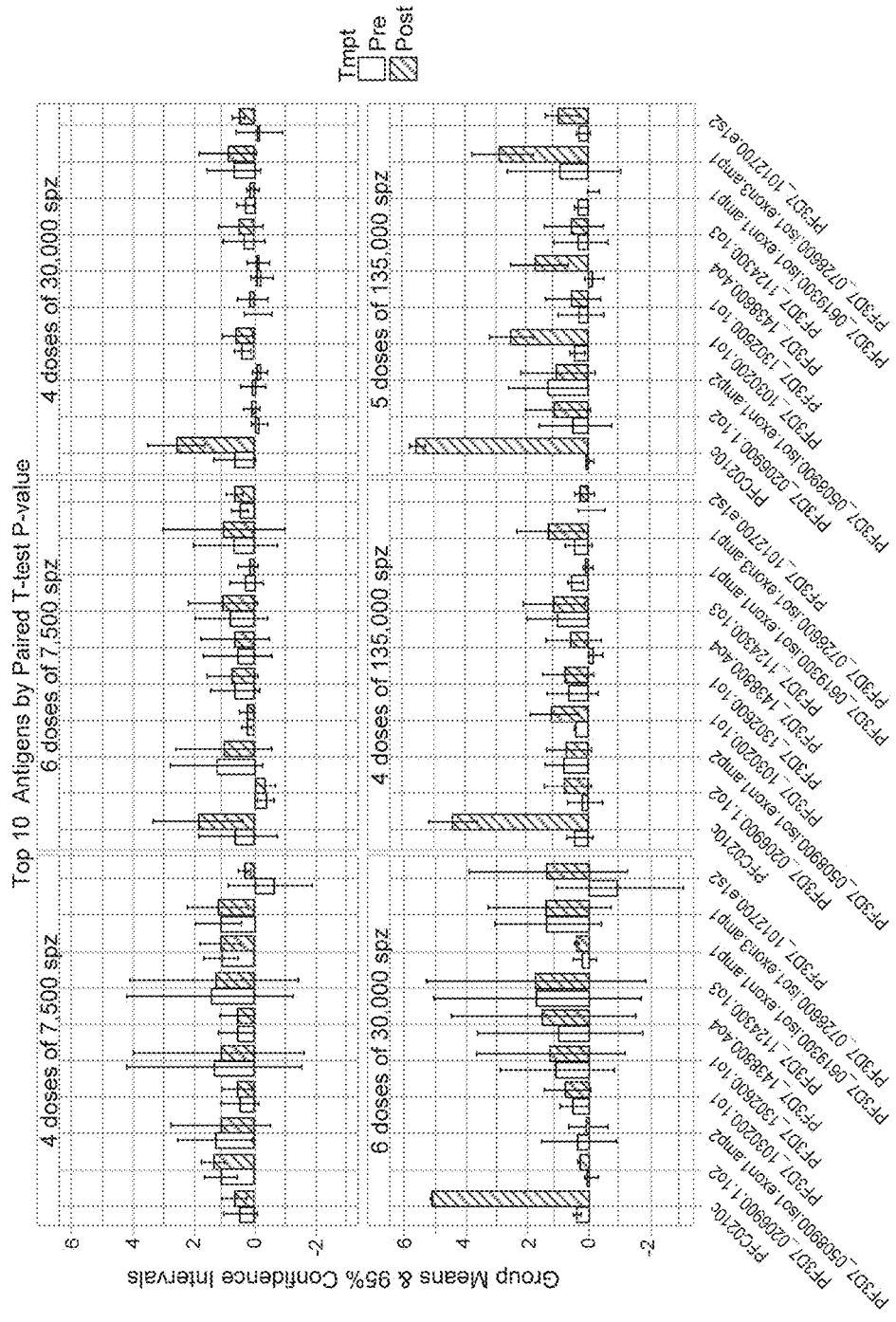
FIG. 2—Immunogenicity profile for 10 antigens of Pf protection by paired T-test. The comparison of post-immunization vs. pre-immunization was tested using paired T-tests. White bars represent pre-immunization mean antibody levels per antigen, and hashed bars represent post-immunization antibody levels. Data are stratified by dosing groups. Error bars represent the 95% confidence interval of the group means.
Figure 3:
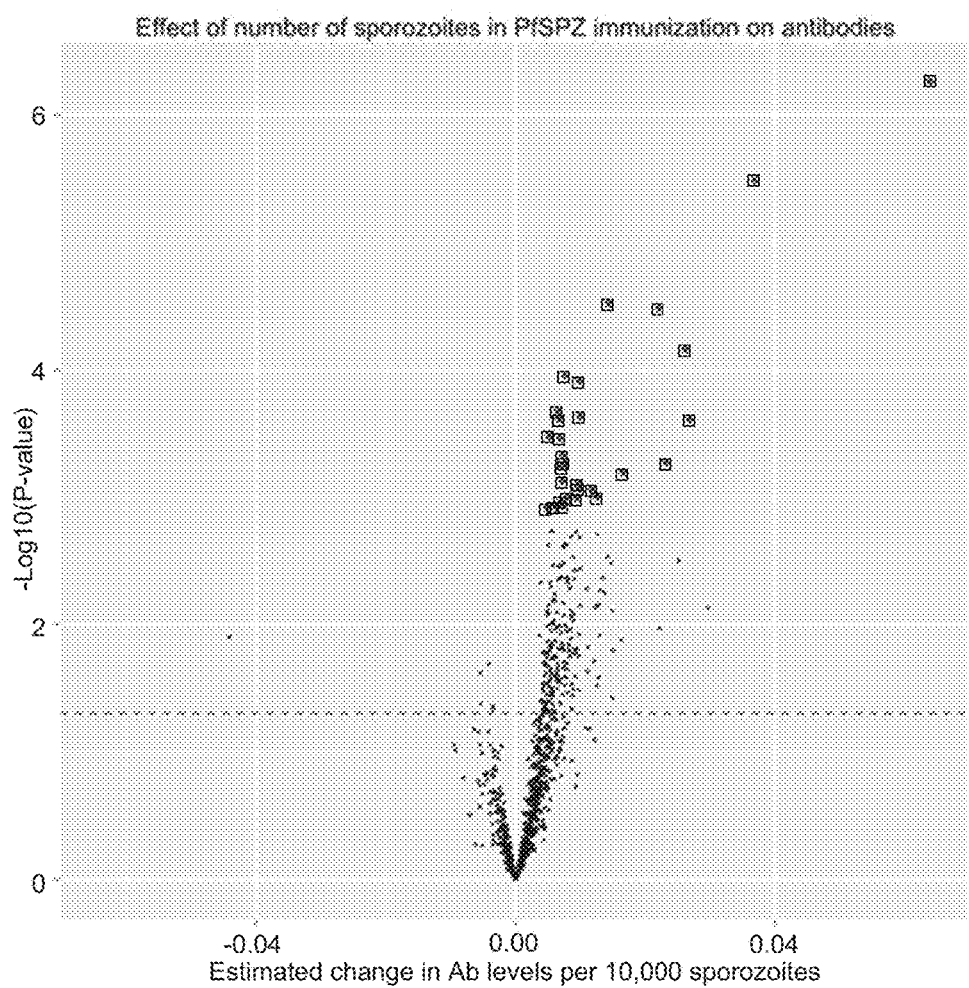
FIG. 3—Effect of PfSPZ dose on antibody levels. The volcano plot depicts the estimated effect of the total dosage (number of PfSPZ administered) on antibody levels. Log change in antibody levels per 10,000 PfSPZ received is shown on the x-axis with the inverse log P-value on the y-axis. The dashed line represents P=0.05, and the triangle points represent 31 antigens that remained significant after correction for the false discovery rate.

A subset of antigens were identified with an "Immunogenic Profile" from paired T-tests (FIG. 2), from the linear regression of antibody Delta measurements (Table 5 and FIG. 3), and from linear mixed effects regression (not shown due to overlap). The dose of sporozoites was significantly associated with antibody levels in 31 antigens after adjusting P-values for multiple testing to avoid false discoveries, also known as correction for the false discovery rate (Table 5 "BH P-value" and FIG. 3 gray triangles).

TABLE 5

Antigens associated with number of sporozoites administered for deltas by linear regression

| Antigen Gene ID | Description | Coefficient | P-value | BH P-value* |
|---|---|---|---|---|
| PF3D7_0304600 | circumsporozoite (CS) protein (CSP) | 0.064 | 5.5E−7 | 0.0005 |
| PF3D7_0312400 | glycogen synthase kinase 3 (GSK3) | 0.037 | 3.3E−6 | 0.002 |
| PF3D7_1468100 | conserved Plasmodium protein, unknown function | 0.014 | 3E−5 | 0.008 |
| PF3D7_1243900 | double C2-like domain-containing protein | 0.022 | 3.3E−5 | 0.008 |
| PF3D7_1030200 | conserved Plasmodium protein, unknown function | 0.026 | 7E−5 | 0.013 |
| PF3D7_0204200 | conserved Plasmodium protein, unknown function | 0.008 | 0.0001 | 0.016 |
| PF3D7_0930300 | merozoite surface protein 1 (MSP1) | 0.010 | 0.0001 | 0.016 |
| PF3D7_1124000 | endoplasmic reticulum oxidoreductin, putative | 0.006 | 0.0002 | 0.021 |
| PF3D7_0904900 | Cu2 -transporting ATPase, putative (CUP) | 0.010 | 0.0002 | 0.021 |
| PF3D7_0906700 | leucine-rich repeat protein (LRR9) | 0.027 | 0.0002 | 0.021 |
| PF3D7_1332200 | conserved Plasmodium protein, unknown function | 0.007 | 0.0002 | 0.021 |
| PF3D7_1011700 | DNA repair protein RAD23, putative | 0.005 | 0.0003 | 0.024 |
| PF3D7_0404600 | conserved Plasmodium membrane protein, unknown function | 0.007 | 0.0003 | 0.024 |
| PF3D7_0215700 | DNA-directed RNA polymerase II second largest subunit, putative | 0.007 | 0.0005 | 0.031 |
| PF3D7_1438800 | conserved Plasmodium protein, unknown function | 0.023 | 0.0005 | 0.031 |
| PF3D7_0929400 | high molecular weight rhoptry protein 2 (RhopH2) | 0.008 | 0.0005 | 0.031 |
| PF3D7_1409800 | RNA binding protein Bruno, putative (HoBo) | 0.007 | 0.0006 | 0.032 |
| PF3D7_0726100 | Plasmodium exported protein, unknown function | 0.017 | 0.0006 | 0.033 |
| PF3D7_1227500 | cyclin (CYC2) | 0.007 | 0.0007 | 0.035 |
| PF3D7_1417200 | NOT family protein, putative | 0.010 | 0.0008 | 0.035 |
| PF3D7_1139500 | AAA family ATPase, putative | 0.010 | 0.0009 | 0.035 |
| PF3D7_0206900 | merozoite surface protein 5 (MSP5), truncated | 0.010 | 0.0009 | 0.035 |
| PF3D7_1427600 | CorA-like Mg2 transporter protein, putative | 0.012 | 0.0009 | 0.035 |
| PF3D7_1110200 | pre-mRNA-processing factor 6, putative (PRPF6) | 0.013 | 0.001 | 0.036 |
| PF3D7_1438000 | eukaryotic translation initiation factor eIF2A, putative | 0.008 | 0.001 | 0.036 |

TABLE 5-continued

Antigens associated with number of sporozoites administered for deltas by linear regression

| Antigen Gene ID | Description | Coefficient | P-value | BH P-value* |
|---|---|---|---|---|
| PF3D7_1247500 | serine/threonine protein kinase, putative | 0.009 | 0.001 | 0.036 |
| PF3D7_1122800 | calcium dependent protein kinase 6 (CDPK6) | 0.007 | 0.001 | 0.036 |
| PF3D7_1327300 | conserved Plasmodium protein, unknown function | 0.007 | 0.001 | 0.036 |
| PF3D7_1432300 | conserved Plasmodium protein, unknown function | 0.006 | 0.001 | 0.036 |
| PF3D7_1469600 | biotin carboxylase subunit of acetyl CoA carboxylase, putative (ACC1) | 0.007 | 0.001 | 0.036 |
| PF3D7_0301700 | Plasmodium exported protein, unknown function | 0.005 | 0.001 | 0.036 |

*BH = Benjamin-Hochberg adjustment for the false discovery rate.

Example 3

Figure 4:
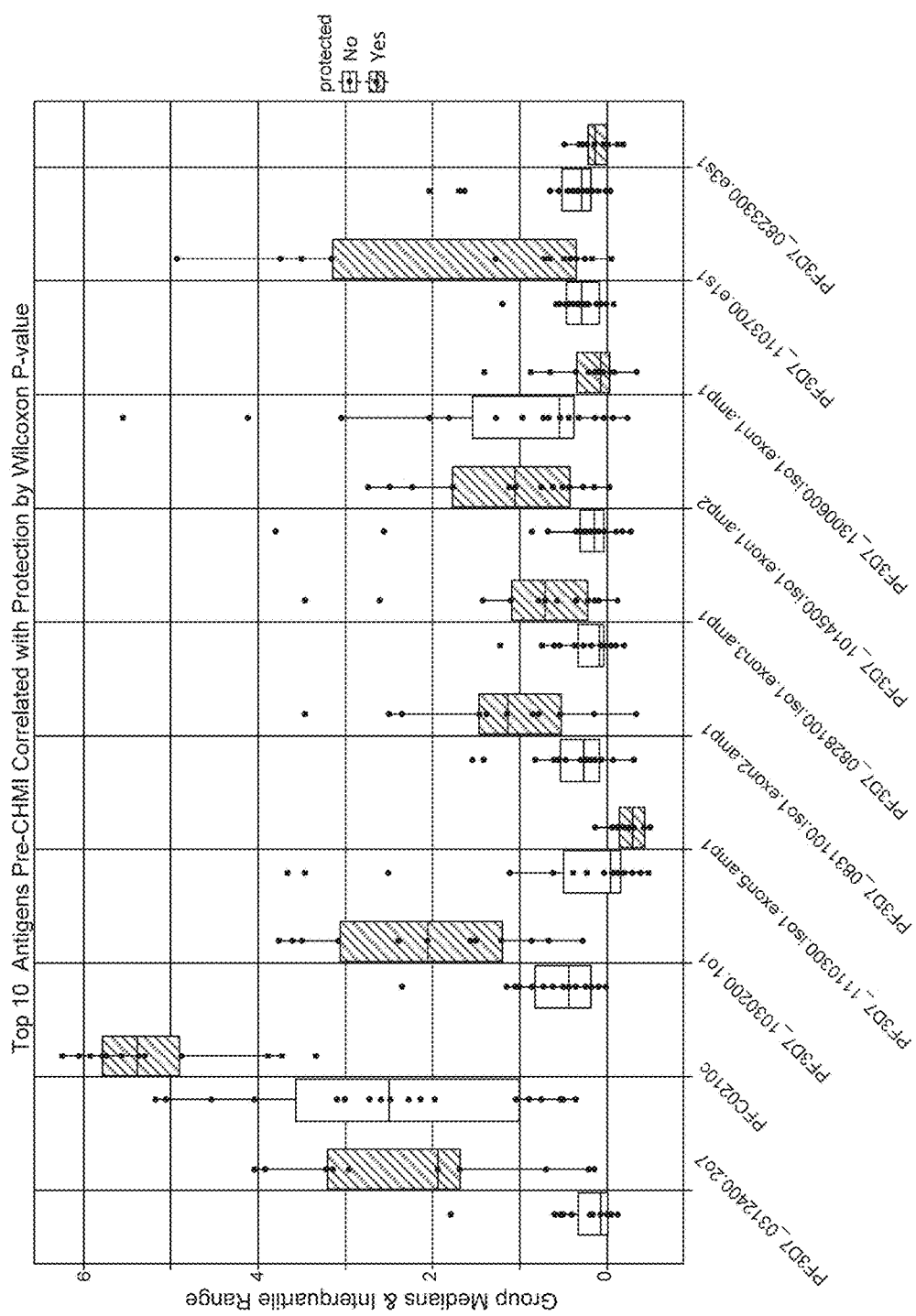
FIG. 4—Ten antigens by Wilcoxon rank-sum test between protected and susceptible volunteers, post immunization/pre-CHMI. The figure presents a comparison of the median and interquartile ranges of pre-CHMI antibody levels between protected and unprotected subjects for each antigen. The vertical "Whisker" bars represent the highest or lowest value within 1.5*IQR of the upper and lower quartiles, respectively. The top 10 antigens are sorted by P-values from Wilcoxon rank-sum tests. Black dots represent individuals' measurements.

Among the 1,567 immunoreactive antigens, a subset of proteins was identified as useful for identifying of protected subjects, or being "Associated with Protection." In addition to CSP and MSP5, pre-CHMI antibodies against antigens with high AUC were glycogen synthase kinase 3, or GSK3 (gene id: PF3D7_0312400; AUC: 0.94, BH P-value=0.004) and a conserved protein of unknown function (PF3D7_1030200; AUC: 0.88, BH P-value=0.036). These antigens and other top antigen are shown in FIG. 4.

Figure 5:
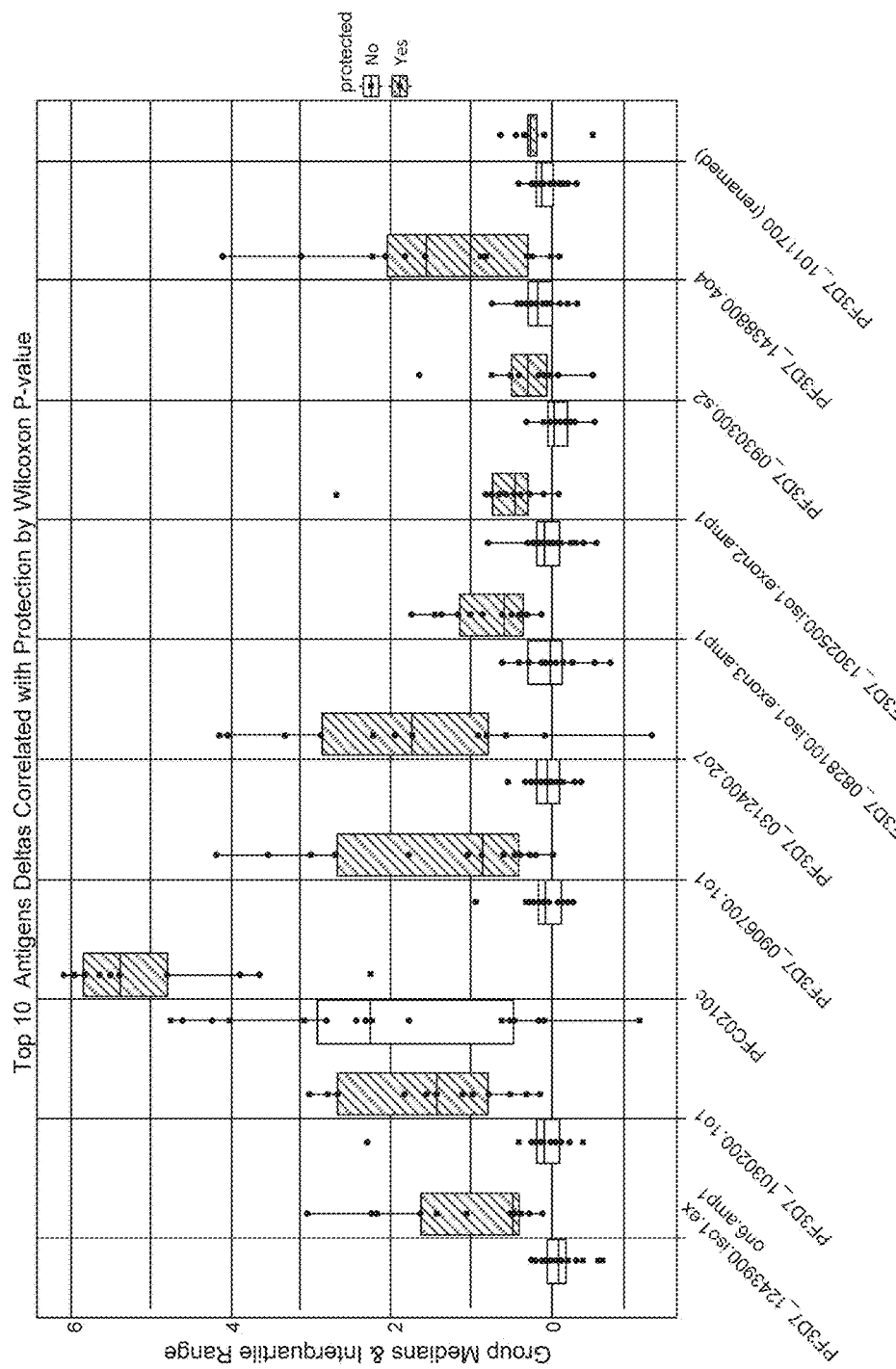
FIG. 5—Deltas for the ten antigens (by Wilcoxon rank-sum test) between protected and susceptible volunteers. The figure presents a comparison of the median and interquartile ranges of antibody Deltas (pre-CHMI minus pre-immunization) between protected and unprotected subjects for each antigen. The vertical "Whisker" bars represent the highest or lowest value within 1.5*IQR of the upper and lower quartiles, respectively. The ten antigens are sorted by P-values from Wilcoxon rank-sum tests. Black dots represent individuals' measurements.

For antibody Deltas (the difference between pre-immunization and pre-CHMI), we identified a leucine-rich repeat protein, called LRR9 (PF3D7_0906700; AUC: 0.90, BH P-value=0.003), and a protein described as double C2-like domain-containing protein, or DOC2 (PF3D7_1243900; AUC: 0.96, BH P-value=0.0005) with high AUC for protection. These antigens and other top antigens are shown in Table 6 and FIG. 5. As with the down-selected chip, the CSP was a top candidate with a pre-CHMI AUC of 0.93 (BH P-value=0.004) and AUC of 0.93 (BH P-value=0.003) for antibody Deltas.

Example 4

Figure 6A:
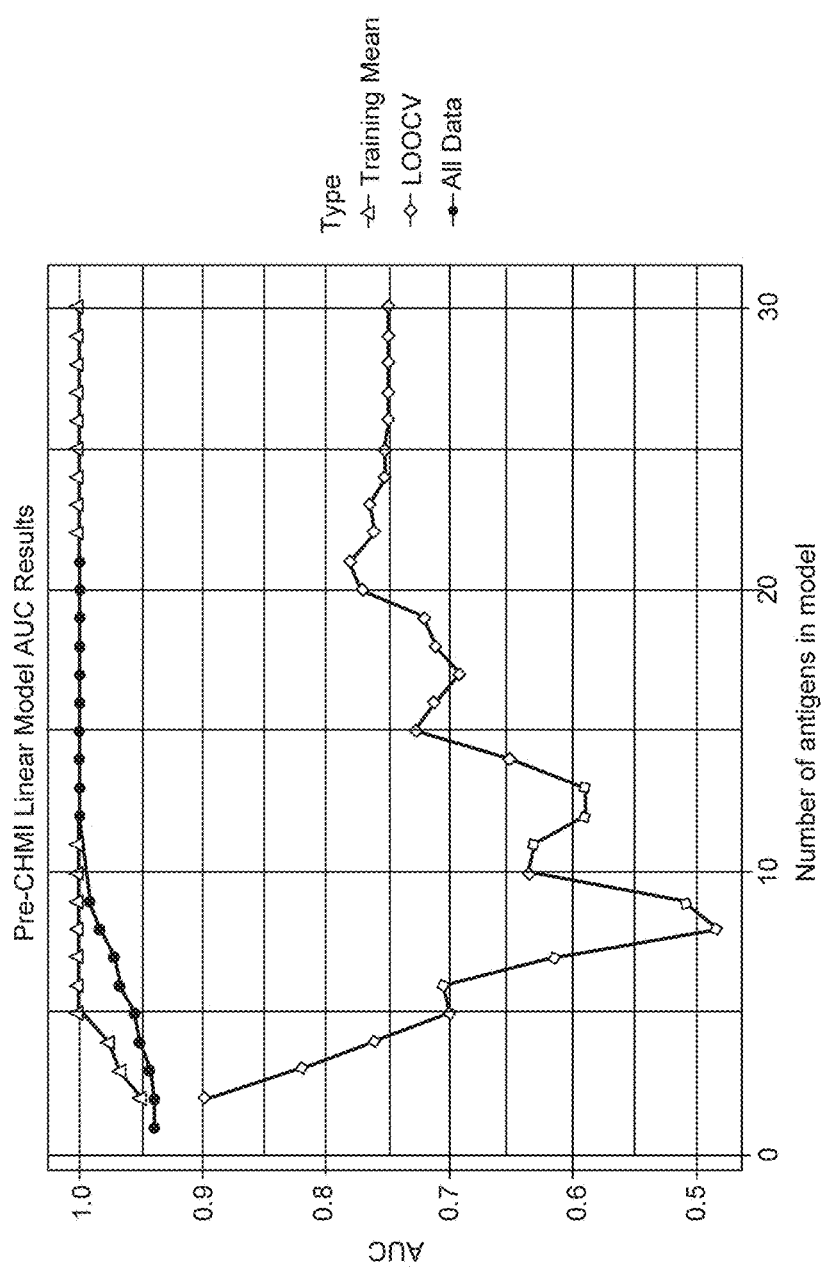
FIGS. 6A-6C—Combinatorial analysis of antibodies associated with protection. The figures represent AUCs modeled on two- to thirty-antibody combinations. The points and lines represent the highest AUCs for linear models fit to varying combinations of antibodies by number of features in the model. The triangle line represents mean highest AUCs for the models fit to all training data sets. The circle lines represent those models fit to the full data set. The diamond line represents the AUC of the best fit models in the training data set on the leave-one-out cross-validation (LOOCV) samples.
Figure 6B:
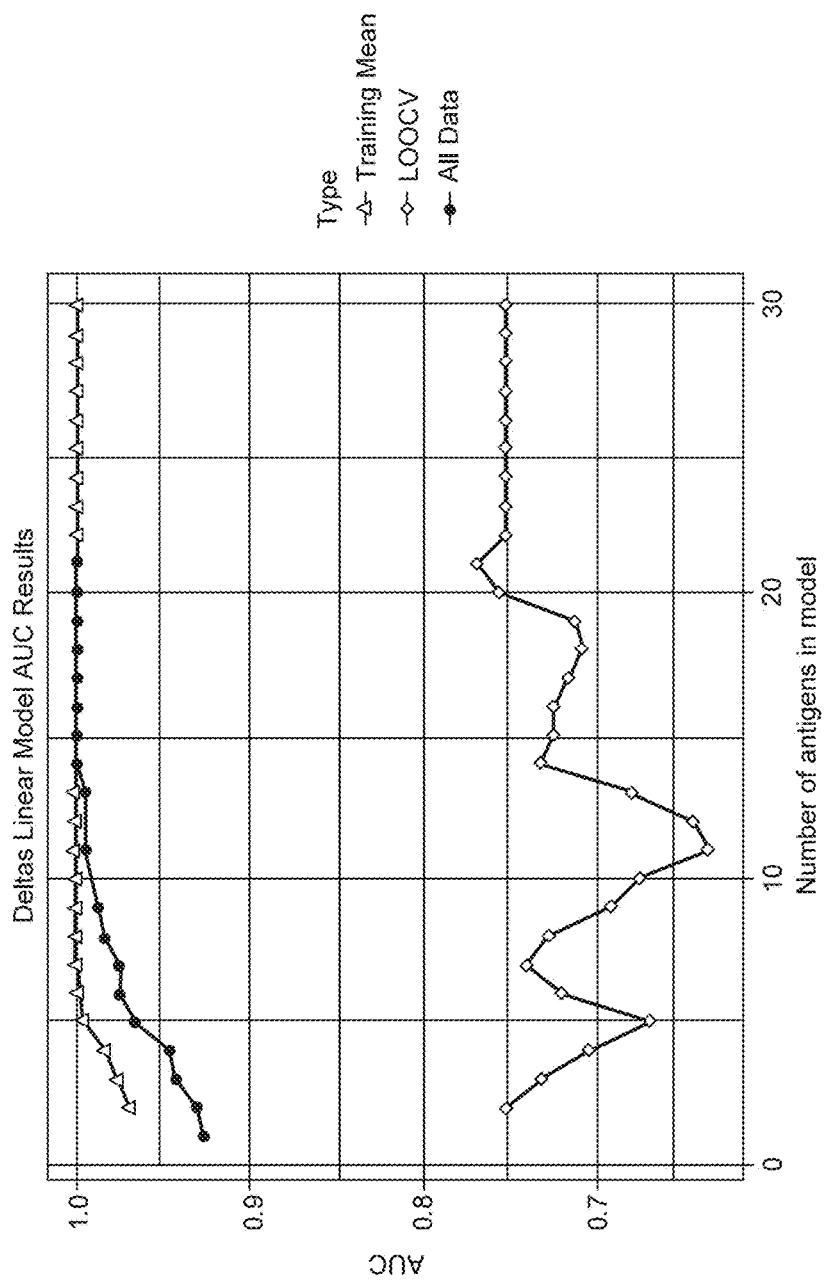
Figure 6C:
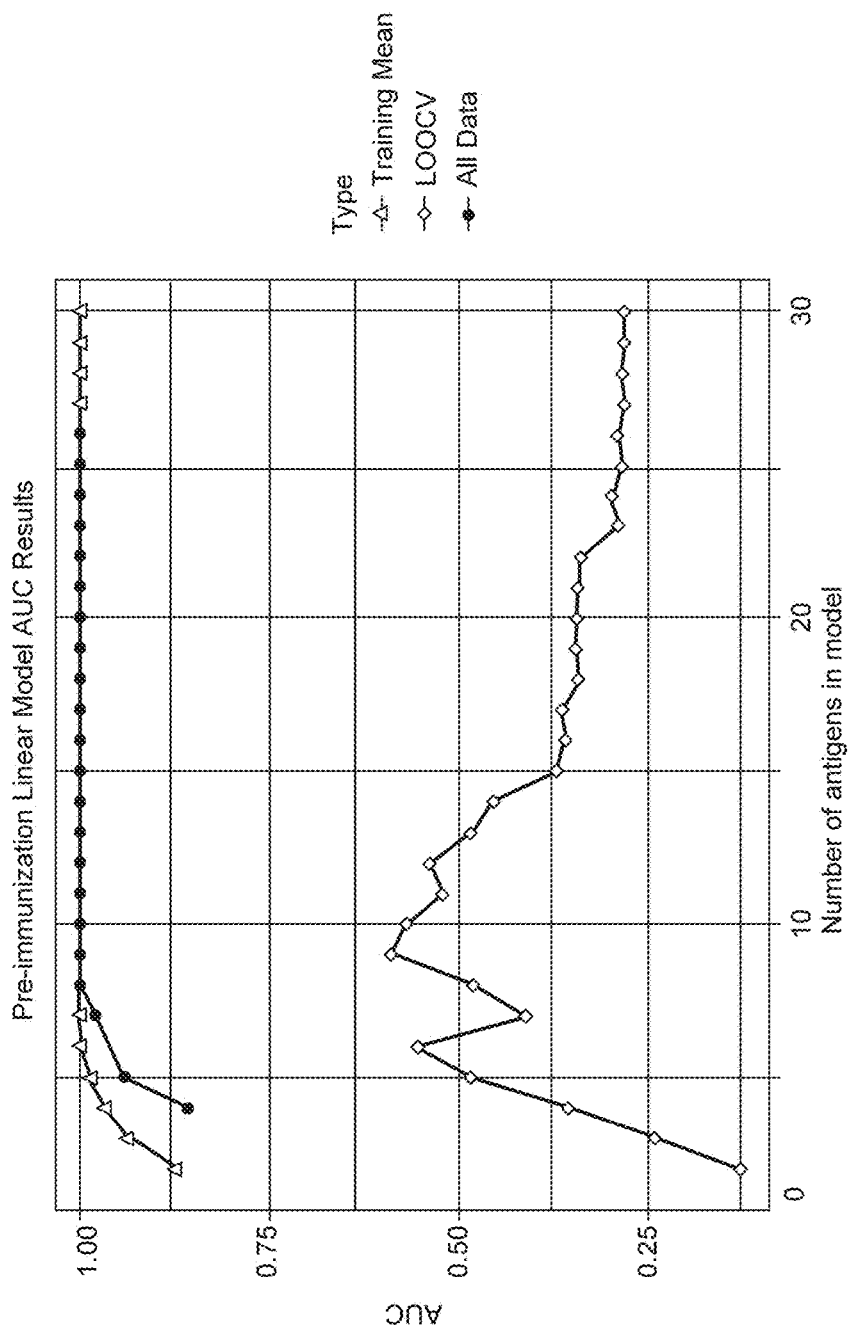

Next, Combinatorial Analysis was performed selecting the highest ranking feature sets by AUC for combinations of two to thirty antigens. The generalizability of each set of features was tested using LOOCV. 960 models were tested on the data from the 32 subjects for pre-CHMI antibody levels or antibody Deltas. For antibody Deltas, the best combinations came from 21-antigen models shown in Table 7 and FIG. 6B (number of antigens in model with the highest LOOCV AUC). Notably, numerous smaller antibody models gave similar AUC in the LOOCV, indicating that a subset of the 21 antigens is probably contributing the most to the AUC, and that there may be antigens in the model that increase the AUC through random noise, and that these antigens may be filtered, as they are not likely to be validated. FIG. 6C illustrates the combinatorial models applied to the pre-immunization time point, which should not bear any antibody combinations that differentiate protected and susceptible individuals. Indeed, the LOOCV AUCs for most antigen combinations fluctuate around 0.5. In contrast, the AUCs for models fit to the training sample set or the full data set quickly approach 1.0 with addition of more antigens.

TABLE 6

Top 10 antigens by Wilcoxon Rank-Sum test between protected and susceptible volunteers, Deltas

| Antigen Gene ID | Description | AUC | P-value | BH P-value* |
|---|---|---|---|---|
| PF3D7_1243900 | double C2-like domain-containing protein (DOC2) | 0.96 | 5.6E-7 | 0.0005 |
| PF3D7_1030200 | conserved Plasmodium protein, unknown function | 0.94 | 5.2E-6 | 0.002 |
| PF3D7_0304600 | circumsporozoite (CS) protein (CSP) | 0.93 | 9.1E-6 | 0.003 |
| PF3D7_0906700 | leucine-rich repeat protein (LRR9) | 0.90 | 4.0E-5 | 0.009 |
| PF3D7_0312400 | glycogen synthase kinase 3 (GSK3) | 0.89 | 7.7E-5 | 0.014 |
| PF3D7_0828100 | conserved Plasmodium protein, unknown function | 0.84 | 0.0007 | 0.114 |
| PF3D7_1302500 | conserved Plasmodium protein, unknown function | 0.84 | 0.0009 | 0.115 |
| PF3D7_0930300 | merozoite surface protein 1 (MSP1) | 0.83 | 0.001 | 0.124 |
| PF3D7_1438800 | conserved Plasmodium protein, unknown function | 0.83 | 0.001 | 0.124 |
| PF3D7_1011700 | DNA repair protein RAD23, putative | 0.83 | 0.001 | 0.131 |

*BH = Benjamin-Hochberg adjustment for the false discovery rate.

TABLE 7

Deltas top antibody combination associated with protection in a linear model

| Antigen Gene ID | Description | Coefficient | Protected Means | Susceptible Means |
|---|---|---|---|---|
| PF3D7_0704700 | conserved Plasmodium membrane protein, unknown function | 2.02 | 0.085 | −0.084 |
| PF3D7_1015900 | enolase (ENO) | 1.96 | 0.192 | −0.011 |
| PF3D7_0631800 | Rifin | 1.79 | 0.303 | −0.275 |
| PF3D7_0604100 | transcription factor with AP2 domain(s) | 1.69 | 0.086 | −0.026 |
| PF3D7_1468100 | conserved Plasmodium protein, unknown function | 1.26 | 0.57 | −0.072 |
| PF3D7_1369200 | conserved Plasmodium protein, unknown function | 1.01 | 0.052 | −0.173 |
| PF3D7_0304600 | circumsporozoite (CS) protein (CSP) | 0.835 | 5.03 | 1.89 |
| PF3D7_0828100 | conserved Plasmodium protein, unknown function | 0.775 | 0.665 | −0.012 |
| PF3D7_0910400 | selenide water dikinase, putative | 0.523 | 0.013 | −0.21 |
| PF3D7_1110200 | pre-mRNA-processing factor 6, putative (PRPF6) | 0.353 | 0.425 | −0.175 |
| PF3D7_0422500 | pre-mRNA-splicing helicase BRR2, putative (BRR2) | 0.332 | 0.256 | −0.098 |
| PF3D7_0206900 | merozoite surface protein 5 (MSP5) | 0.251 | 0.526 | 0.029 |
| PF3D7_0728600 | zinc finger, C3HC4 type, putative | 0.199 | 1.57 | 0.152 |
| PF3D7_1243900 | double C2-like domain-containing protein | 0.134 | 1.07 | −0.076 |
| PF3D7_1417200 | NOT family protein, putative | 0.045 | 0.341 | −0.143 |
| PF3D7_0905300 | dynein heavy chain, putative | 0.031 | 0.15 | −0.087 |
| PF3D7_1412200 | conserved Plasmodium protein, unknown function | 0.002 | 0.073 | −0.167 |
| PF3D7_0701600 | Pfmc-2TM Maurer's cleft two transmembrane protein | −0.297 | −0.051 | 0.141 |
| PF3D7_0704800 | conserved Plasmodium protein, unknown function | −1.07 | −0.177 | 0.072 |
| PF3D7_1219300 | erythrocyte membrane protein 1, PfEMP1 | −1.24 | −0.298 | −0.092 |
| PF3D7_1141600 | dolichol phosphate mannose synthase (DPM1) | −3.95 | −0.115 | 0.101 |

Example 5

Using an inclusive approach to antigen selection, antibodies against 52 *P. falciparum* antigens were identified that showed significant vaccine immunogenicity and dose responsiveness ("Immunogenicity Profile", had a significant association with distinguishing protection or susceptibility to CHMI ("Association with Protection") or were found as a top signature of protection in combinatorial analysis ("Combinatorial Analysis"). These are shown in Table 8.

Figure 7A:
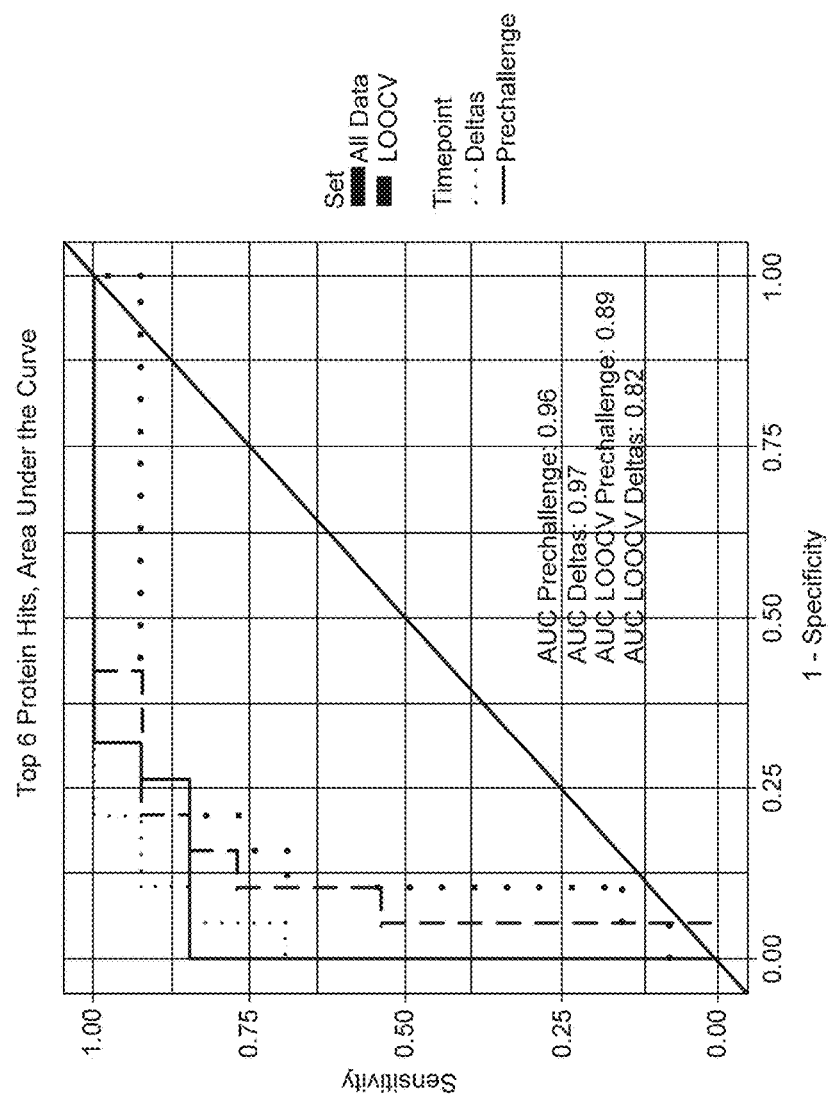
FIGS. 7A and 7B—Show the performance of the antibodies in combinatorial models of antibody Deltas. The ROC curves represent the true positive rate (sensitivity) and false positive rate (1-specificity) of the linear combinations of the down-selected list of antibody targets for the comparison of protected and susceptible vaccines following CHMI.
Figure 7B:
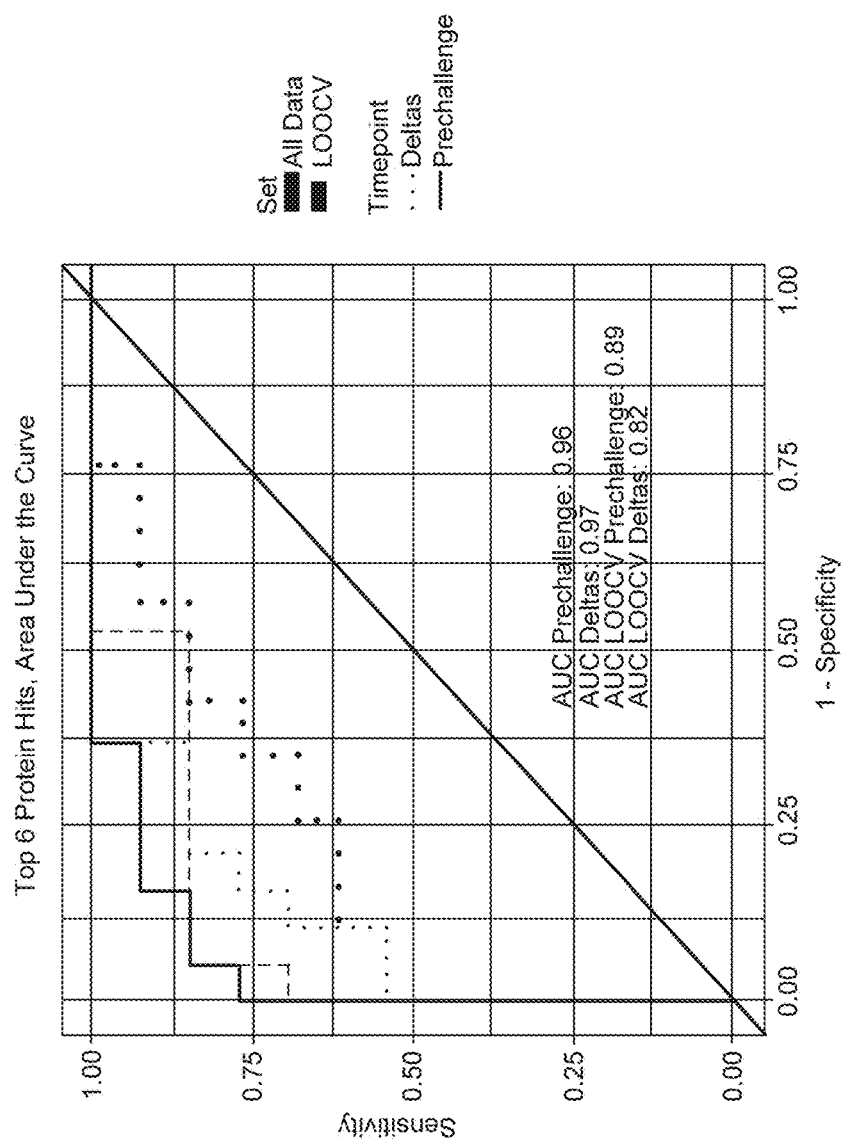

Antibody levels for each listed antigen were individually inspected and graded on immunogenicity, protection and AUC. Ten antigens were further identified from the set of 52 that fulfilled our criteria for the best candidates for further development (Table 9). Of those 10 antigens, 6 had the highest performance. The LOOCV AUCs for the combination of top 6 protein hits was 0.89 for pre-CHMI antibody levels and 0.82 for antibody Deltas, while addition of the next 4 targets resulted in LOOCV AUCs of 0.91 and 0.81, respectively (FIG. 7A-B).

TABLE 8

Total of 52 antigens down-selected from 1,567 immunoreactive antigens. Criteria for down-selecting antigens was demonstration of a significant immunogenicity profile, significant association with protection or a component of optimal antigen combinations in combinatorial analysis.

| | Gene ID | Description | Criteria For Selection |
|---|---|---|---|
| 1 | PF3D7_0204200 | conserved Plasmodium protein, unknown function | Immunogenicity Profile |
| 2 | PF3D7_0206900 | merozoite surface protein 5 (MSP5) | Immunogenicity Profile |
| 3 | PF3D7_0206900 | merozoite surface protein 5 (MSP5), truncated | Immunogenicity Profile; Associated With Protection; Combinatorial Analysis |
| 4 | PF3D7_0207500 | serine repeat antigen 6 (SERA6) | Immunogenicity Profile |
| 5 | PF3D7_0215700 | DNA-directed RNA polymerase II second largest subunit, putative | Immunogenicity Profile |
| 6 | PF3D7_0301700 | Plasmodium exported protein, unknown function | Immunogenicity Profile |

TABLE 8-continued

Total of 52 antigens down-selected from 1,567 immunoreactive antigens.
Criteria for down-selecting antigens was demonstration of a significant
immunogenicity profile, significant association with protection or a component
of optimal antigen combinations in combinatorial analysis.

| | Gene ID | Description | Criteria For Selection |
|---|---|---|---|
| 7 | PF3D7_0304600 | circumsporozoite (CS) protein (CSP) | Immunogenicity Profile; Associated With Protection; Combinatorial Analysis |
| 8 | PF3D7_0312400 | glycogen synthase kinase 3 (GSK3) | Immunogenicity Profile; Associated With Protection; Combinatorial Analysis |
| 9 | PF3D7_0404600 | conserved Plasmodium membrane protein, unknown function | Immunogenicity Profile |
| 10 | PF3D7_0422500 | pre-mRNA-splicing helicase BRR2, putative (BRR2) | Combinatorial Analysis |
| 11 | PF3D7_0508900 | conserved Plasmodium protein, unknown function | Immunogenicity Profile |
| 12 | PF3D7_0604100 | transcription factor with AP2 domain(s) | Combinatorial Analysis |
| 13 | PF3D7_0631800 | Rifin | Combinatorial Analysis |
| 16 | PF3D7_0701600 | Pfmc-2TM Maurer's cleft two transmembrane protein | Combinatorial Analysis |
| 14 | PF3D7_0704700 | conserved Plasmodium membrane protein, unknown function | Combinatorial Analysis |
| 15 | PF3D7_0704800 | conserved Plasmodium protein, unknown function | Combinatorial Analysis |
| 17 | PF3D7_0726100 | Plasmodium exported protein, unknown function | Immunogenicity Profile |
| 18 | PF3D7_0728600 | zinc finger, C3HC4 type, putative | Combinatorial Analysis |
| 19 | PF3D7_0828100 | conserved Plasmodium protein, unknown function | Combinatorial Analysis |
| 20 | PF3D7_0904900 | Cu2 -transporting ATPase, putative (CUP) | Immunogenicity Profile |
| 21 | PF3D7_0905300 | dynein heavy chain, putative | Combinatorial Analysis |
| 22 | PF3D7_0906700 | leucine-rich repeat protein (LRR9) | Immunogenicity Profile; Associated With Protection |
| 23 | PF3D7_0910400 | selenide water dikinase, putative | Combinatorial Analysis |
| 24 | PF3D7_0918900 | gamma-glutamylcysteine synthetase (gammaGCS) | Immunogenicity Profile |
| 25 | PF3D7_0929400 | high molecular weight rhoptry protein 2 (RhopH2) | Immunogenicity Profile |
| 26 | PF3D7_0930300 | merozoite surface protein 1 (MSP1) | Immunogenicity Profile |
| 27 | PF3D7_1011700 | DNA repair protein RAD23, putative | Immunogenicity Profile |
| 28 | PF3D7_1015900 | enolase (ENO) | Combinatorial Analysis |
| 29 | PF3D7_1030200 | conserved Plasmodium protein, unknown function | Immunogenicity Profile; Associated With Protection |
| 30 | PF3D7_1110200 | pre-mRNA-processing factor 6, putative (PRPF6) | Immunogenicity Profile; Combinatorial Analysis |
| 31 | PF3D7_1122800 | calcium dependent protein kinase 6 (CDPK6) | Immunogenicity Profile |
| 32 | PF3D7_1124000 | endoplasraic reticulum oxidoreductin, putative | Immunogenicity Profile |
| 33 | PF3D7_1139500.1 | AAA family ATPase, putative | Immunogenicity Profile |
| 34 | PF3D7_1141600 | dolichol phosphate mannose synthase (DPM1) | Combinatorial Analysis |
| 35 | PF3D7_1219300 | erythrocyte membrane protein 1, PfEMP1 | Combinatorial Analysis |
| 36 | PF3D7_1221000 | histone-lysine N-methyltransferase, H3 lysine-4 specific (SET10) | Immunogenicity Profile |
| 37 | PF3D7_1227500 | cyclin (CYC2) | Immunogenicity Profile |
| 38 | PF3D7_1243900 | double C2-like domain-containing protein | Immunogenicity Profile; Associated With Protection; Combinatorial Analysis |
| 39 | PF3D7_1247500 | serine/threonine protein kinase, putative | Immunogenicity Profile |
| 40 | PF3D7_1327300 | conserved Plasmodium protein, unknown function | Immunogenicity Profile |
| 41 | PF3D7_1332200 | conserved Plasmodium protein, unknown function | Immunogenicity Profile |
| 42 | PF3D7_1369200 | conserved Plasmodium protein, unknown function | Combinatorial Analysis |
| 43 | PF3D7_1409800 | RNA binding protein Bruno, putative (HoBo) | Immunogenicity Profile |
| 44 | PF3D7_1412200 | conserved Plasmodium protein, unknown function | Combinatorial Analysis |
| 45 | PF3D7_1417200 | NOT family protein, putative | Immunogenicity Profile; Combinatorial Analysis |

TABLE 8-continued

Total of 52 antigens down-selected from 1,567 immunoreactive antigens. Criteria for down-selecting antigens was demonstration of a significant immunogenicity profile, significant association with protection or a component of optimal antigen combinations in combinatorial analysis.

| | Gene ID | Description | Criteria For Selection |
|---|---|---|---|
| 46 | PF3D7_1427600 | CorA-like Mg2 transporter protein, putative | Immunogenicity Profile |
| 47 | PF3D7_1431100 | conserved Plasmodium protein, unknown function | Immunogenicity Profile |
| 48 | PF3D7_1432300 | conserved Plasmodium protein, unknown function | Immunogenicity Profile |
| 49 | PF3D7_1438000 | eukaryotic translation initiation factor eIF2A, putative | Immunogenicity Profile |
| 50 | PF3D7_1438800 | conserved Plasmodium protein, unknown function | Immunogenicity Profile |
| 51 | PF3D7_1468100 | conserved Plasmodium protein, unknown function | Immunogenicity Profile; Combinatorial Analysis |
| 52 | PF3D7_1469600 | biotin carboxylase subunit of acetyl CoA carboxylase, putative (ACC1) | Immunogenicity Profile |

TABLE 9

List of ten antigens for identifying PfSPZ vaccine protection.

| Antigen Gene ID | Description | Nucleic Acid Sequence | Protein Sequence |
|---|---|---|---|
| PF3D7_0304600 | circumsporozoite (CS) protein (CSP) | SEQ ID NO: 9 | SEQ ID NO: 19 |
| PF3D7_0206900 | merozoite surface protein 5 (MSP5) | SEQ ID NO: 10 | SEQ ID NO: 20 |
| PF3D7_1030200 | conserved Plasmodium protein, unknown function | SEQ ID NO: 1 | SEQ ID NO: 11 |
| PF3D7_0312400 | glycogen synthase kinase 3 (GSK3) | SEQ ID NO: 4 | SEQ ID NO: 14 |
| PF3D7_1243900 | double C2-like domain-containing protein (DOC2) | SEQ ID NO: 3 | SEQ ID NO: 13 |
| PF3D7_0906700 | leucine-rich repeat protein (LRR9) | SEQ ID NO: 2 | SEQ ID NO: 12 |
| PF3D7_1438800 | conserved Plasmodium protein, unknown function | SEQ ID NO: 5 | SEQ ID NO: 15 |
| PF3D7_0828100 | conserved Plasmodium protein, unknown function | SEQ ID NO: 6 | SEQ ID NO: 16 |
| PF3D7_0728600 | zinc finger, C3HC4 type, putative | SEQ ID NO: 7 | SEQ ID NO: 17 |
| PF3D7_1468100 | conserved Plasmodium protein, unknown function | SEQ ID NO: 8 | SEQ ID NO: 18 |

Example 6

An additional set of P. falciparum whole proteome microarray experiments were run on a set of samples derived from an independent clinical trial of PfSPZ Vaccine, "Study of Controlled Human Malaria Infections to Evaluate Protection After Intravenous or Intramuscular Administration of PfSPZ Vaccine in Malaria-Naive Adults" (ClinicalTrials.gov Identifier: NCT02015091). Serum samples assayed were from the trial arm receiving 3 doses of 9×10$^5$ PfSPZ Vaccine and given controlled human malaria infection (CHMI), for which 9 out of 14 volunteers were protected.

As a validation data set, only the 6 Pf antigens (PF3D7_1030200 (SEQ ID NO:11);

LRR9 (SEQ ID NO:12); DOC2 (SEQ ID NO:13); GSK3 (SEQ ID NO:14); CSP (SEQ ID NO:19); and MSP5 (SEQ ID NO:20) were assessed for correlation with protection. These statistical methods used to determine association with sterile protection after CHMI: 1) classification of subjects as "protected" or "susceptible" using fitted generalized linear models of antibody measurements after third vaccination and before CHMI and antibody Deltas (baseline to post-third vaccination and baseline to pre-CHMI) on the probability of being protected (logistic regression); 2) Estimation of the area under the ROC curve (AUC) in the classification of subjects as "protected" or "susceptible" as compared to the true diagnosis of protected or susceptible according to the gold standard of thick and thin blood smear by microscopy (as part of the CHMI protocol); 3) calculation of sensitivity and specificity of the 6 Pf antigen combinatorial model.

Figure 8:
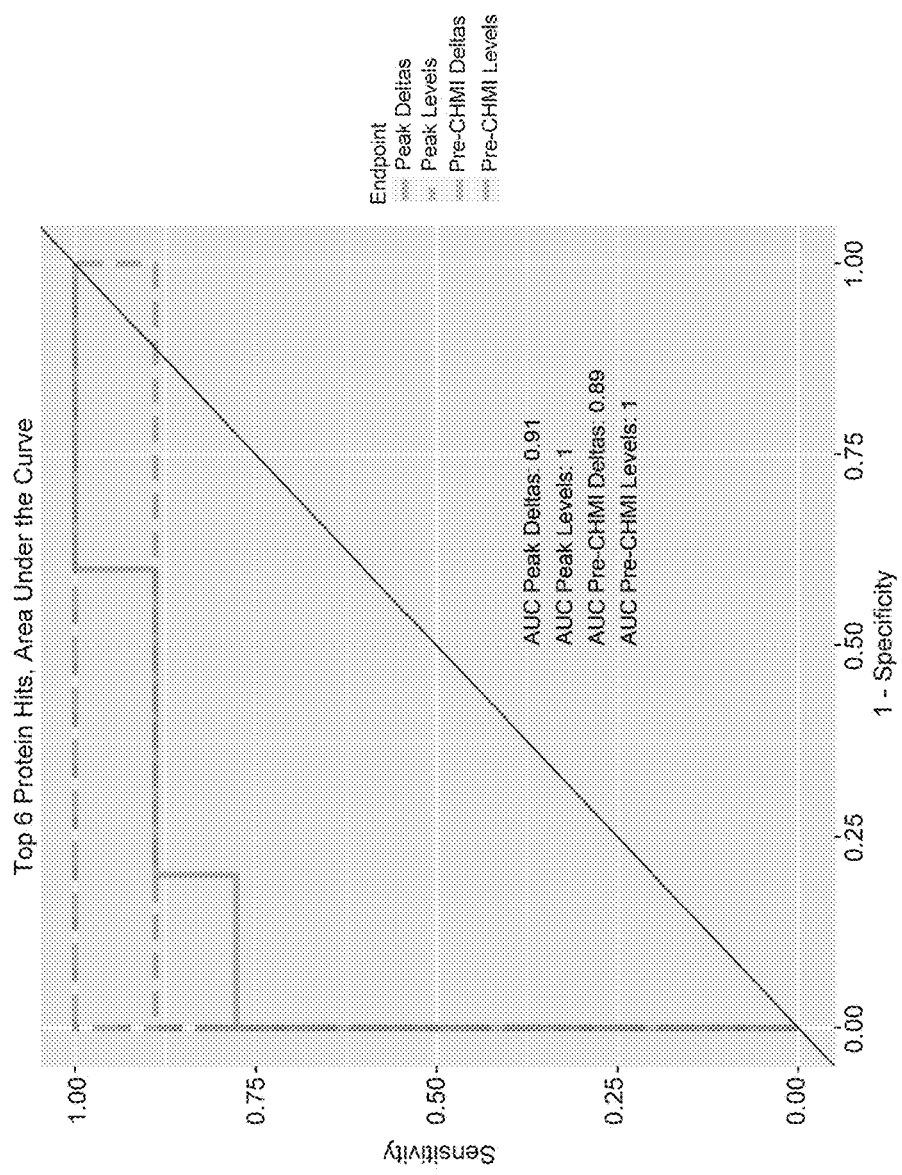
FIG. 8—Shows the performance of the 6 Pf antibodies in combinatorial models of Peak antibody levels and antibody Deltas and Pre-CHMI antibody levels and antibody Deltas. The ROC curves represent the true positive rate (sensitivity) and false positive rate (1-specificity) of the linear combinations of the previously defined list of antibody targets for the comparison of protected and susceptible vaccines following CHMI (corresponding to SEQ ID NOs:11-14 & 19-20). ROC curves were modeled on data from all subjects.

Antibody levels measured after the third vaccination ("Peak") were able to classify subjects with an AUC of 1.0, while Peak antibody Deltas had an AUC of 0.91. Antibody levels measured before CHMI ("Pre-CHMI") classified subjects with an AUC of 1.0, while Pre-CHMI Deltas had an AUC of 0.89 (FIG. 8). The performance characteristics (sensitivity, specificity, false positives and false negatives) for the 6 Pf antigen combination are shown in Table 10 for 6-antigen combinations and in Tables 11-12 for various combinations of the 6 Pf antigens.

TABLE 10

Performance characteristics of Peak antibody levels, Peak antibody Deltas (difference between pre-immunization and post-immunization immunoreactivities), Pre-CHMI antibody levels and Pre-CHMI antibody Deltas against combinations of 6 Pf antigens in discriminating protection and susceptibility to CHMI.

| Antigens | Predictive Value * | Sensitivity | Specificity | False Positives | False Negatives |
|---|---|---|---|---|---|
| Peak Antibody Levels | 9.47 | 100% | 100% | 0 | 0 |
| Peak Antibody Deltas | −2.04 | 89% | 80% | 1 | 1 |
| Pre-CHMI Antibody Levels | 163 | 100% | 100% | 0 | 0 |
| Pre-CHMI Antibody Deltas | 0.76 | 89% | 100% | 0 | 1 |

* Predictive Value: The predictive value displayed is the optimal logistic regression prediction ("predictive value") for maximizing sensitivity and specificity performance characteristics in determining protection against *P. falciparum* malaria.

TABLE 11

Performance characteristics of 6 Pf antigens using Peak antibody levels, Peak antibody Deltas (difference between pre-immunization and post-immunization immunoreactivities), Pre-CHMI antibody levels and Pre-CHMI antibody Deltas against combinations of 6 Pf antigens in discriminating protection and susceptibility to CHMI.

| Antigens | Peak Levels | | Peak Deltas | | Pre-CHMI Levels | | Pre-CHMI Deltas | |
|---|---|---|---|---|---|---|---|---|
| | Sensitivity | Specificity | Sensitivity | Specificity | Sensitivity | Specificity | Sensitivity | Specificity |
| CSP | 0.67 | 0.40 | 0.89 | 0.40 | 0.56 | 0.60 | 0.89 | 0.60 |
| MSP5 | 0.56 | 0.60 | 0.67 | 0.80 | 0.44 | 0.60 | 0.67 | 0.60 |
| PF3D7_1030200 | 0.78 | 0.60 | 0.78 | 0.60 | 0.56 | 0.60 | 0.44 | 0.60 |
| GSK3 | 0.78 | 0.60 | 0.78 | 0.60 | 0.67 | 0.60 | 0.44 | 0.60 |
| DOC2 | 0.89 | 0.60 | 0.89 | 0.60 | 0.89 | 0.60 | 0.89 | 0.60 |
| LRR9 | 0.78 | 0.80 | 0.78 | 0.60 | 0.89 | 0.60 | 0.78 | 0.80 |
| CSP, MSP5 | 0.44 | 0.60 | 0.78 | 0.80 | 0.89 | 0.60 | 0.78 | 0.60 |
| CSP, PF3D7_1030200 | 0.56 | 0.60 | 0.44 | 0.60 | 0.67 | 0.60 | 0.78 | 0.60 |
| CSP, GSK3 | 0.67 | 0.80 | 0.78 | 0.60 | 0.78 | 0.60 | 0.89 | 0.60 |
| CSP, DOC2 | 0.78 | 0.80 | 0.67 | 0.60 | 0.89 | 0.60 | 0.78 | 0.60 |
| CSP, LRR9 | 0.78 | 0.80 | 0.78 | 0.80 | 0.67 | 0.80 | 0.78 | 0.80 |
| MSP5, PF3D7_1030200 | 0.89 | 0.60 | 0.78 | 0.80 | 0.67 | 0.60 | 0.56 | 0.60 |
| MSP5, GSK3 | 0.89 | 0.60 | 0.78 | 0.80 | 0.89 | 0.60 | 0.44 | 0.60 |
| MSP5, DOC2 | 0.67 | 0.80 | 0.67 | 0.80 | 0.78 | 0.60 | 0.78 | 0.60 |
| MSP5, LRR9 | 0.78 | 0.80 | 0.78 | 0.80 | 0.89 | 0.60 | 0.78 | 0.80 |
| PF3D7_1030200, GSK3 | 0.78 | 0.60 | 0.78 | 0.60 | 0.44 | 0.60 | 0.44 | 0.60 |
| PF3D7_1030200, DOC2 | 0.89 | 0.80 | 0.67 | 0.80 | 0.67 | 0.80 | 0.78 | 0.60 |
| PF3D7_1030200, LRR9 | 0.78 | 0.80 | 0.89 | 0.80 | 0.67 | 0.80 | 0.78 | 0.80 |
| GSK3, DOC2 | 0.89 | 0.80 | 0.67 | 0.80 | 1.00 | 0.60 | 0.78 | 0.60 |
| GSK3, LRR9 | 0.78 | 0.60 | 0.67 | 0.80 | 0.78 | 0.80 | 0.78 | 0.80 |
| DOC2, LRR9 | 0.89 | 0.80 | 0.78 | 0.80 | 0.67 | 0.80 | 0.78 | 0.80 |
| CSP, MSP5, PF3D7_1030200 | 0.44 | 0.60 | 0.78 | 0.80 | 0.89 | 0.60 | 0.89 | 0.60 |
| CSP, MSP5, GSK3 | 0.78 | 0.60 | 0.78 | 0.80 | 0.78 | 0.80 | 0.78 | 0.60 |
| CSP, MSP5, DOC2 | 0.78 | 0.80 | 0.67 | 0.80 | 0.78 | 0.80 | 0.78 | 0.80 |
| CSP, MSP5, LRR9 | 0.78 | 0.80 | 0.67 | 0.80 | 0.78 | 0.80 | 0.89 | 1.00 |
| CSP, PF3D7_1030200, GSK3 | 0.67 | 0.80 | 0.67 | 0.60 | 0.67 | 0.60 | 0.44 | 0.60 |
| CSP, PF3D7_1030200, DOC2 | 0.89 | 0.80 | 0.78 | 0.80 | 1.00 | 0.60 | 0.67 | 0.80 |
| CSP, PF3D7_1030200, LRR9 | 0.89 | 1.00 | 0.89 | 0.80 | 0.89 | 1.00 | 0.78 | 0.80 |
| CSP, GSK3, DOC2 | 0.89 | 0.80 | 0.78 | 0.80 | 0.78 | 0.60 | 0.78 | 0.60 |
| CSP, GSK3, LRR9 | 0.78 | 0.80 | 0.67 | 0.80 | 0.67 | 0.80 | 0.78 | 0.80 |
| CSP, DOC2, LRR9 | 0.89 | 0.80 | 0.78 | 0.80 | 0.89 | 0.80 | 0.78 | 0.80 |
| MSP5, PF3D7_1030200, GSK3 | 1.00 | 0.60 | 0.78 | 0.80 | 0.89 | 0.60 | 0.56 | 0.60 |
| MSP5, PF3D7_1030200, DOC2 | 0.89 | 0.80 | 0.78 | 0.80 | 0.78 | 0.80 | 0.78 | 0.60 |
| MSP5, PF3D7_1030200, LRR9 | 0.67 | 0.80 | 0.89 | 0.80 | 0.89 | 0.80 | 0.78 | 0.80 |
| MSP5, GSK3, DOC2 | 0.89 | 0.80 | 0.78 | 0.80 | 0.78 | 0.80 | 0.78 | 0.60 |
| MSP5, GSK3, LRR9 | 0.78 | 0.80 | 0.78 | 0.80 | 0.78 | 0.80 | 0.89 | 0.80 |
| MSP5, DOC2, LRR9 | 0.89 | 0.80 | 0.78 | 0.80 | 0.89 | 1.00 | 0.89 | 0.80 |
| PF3D7_1030200, GSK3, DOC2 | 0.89 | 0.80 | 0.67 | 0.80 | 0.89 | 0.60 | 0.78 | 0.60 |
| PF3D7_1030200, GSK3, LRR9 | 0.78 | 0.80 | 0.89 | 0.80 | 0.89 | 0.80 | 0.78 | 0.80 |
| PF3D7_1030200, DOC2, LRR9 | 0.78 | 0.80 | 0.89 | 0.80 | 0.89 | 0.80 | 0.89 | 0.80 |
| GSK3, DOC2, LRR9 | 0.89 | 0.80 | 0.78 | 0.80 | 0.78 | 0.80 | 0.78 | 0.80 |
| CSP, MSP5, PF3D7_1030200, GSK3 | 0.67 | 0.60 | 0.78 | 0.80 | 0.67 | 0.80 | 0.44 | 0.60 |
| CSP, MSP5, PF3D7_1030200, DOC2 | 0.89 | 0.80 | 0.78 | 0.80 | 0.78 | 0.80 | 0.78 | 0.80 |
| CSP, MSP5, PF3D7_1030200, LRR9 | 0.89 | 1.00 | 0.78 | 0.80 | 1.00 | 1.00 | 0.89 | 1.00 |
| CSP, MSP5, GSK3, DOC2 | 0.89 | 0.80 | 0.78 | 0.80 | 1.00 | 0.60 | 0.78 | 0.80 |
| CSP, MSP5, GSK3, LRR9 | 0.78 | 0.80 | 0.89 | 0.80 | 0.89 | 1.00 | 0.89 | 1.00 |
| CSP, MSP5, DOC2, LRR9 | 0.78 | 0.80 | 0.67 | 0.80 | 0.89 | 1.00 | 0.89 | 1.00 |
| CSP, PF3D7_1030200, GSK3, DOC2 | 0.89 | 0.80 | 0.78 | 0.80 | 0.67 | 0.60 | 0.78 | 0.60 |
| CSP, PF3D7_1030200, GSK3, LRR9 | 1.00 | 1.00 | 0.89 | 0.80 | 1.00 | 1.00 | 0.78 | 0.80 |
| CSP, PF3D7_1030200, DOC2, LRR9 | 0.89 | 1.00 | 0.89 | 1.00 | 0.89 | 1.00 | 0.89 | 0.80 |
| CSP, GSK3, DOC2, LRR9 | 1.00 | 0.80 | 0.89 | 0.80 | 0.89 | 0.80 | 0.78 | 0.80 |
| MSP5, PF3D7_1030200, GSK3, DOC2 | 0.89 | 0.80 | 0.78 | 0.80 | 0.78 | 0.80 | 0.78 | 0.60 |

TABLE 11-continued

Performance characteristics of 6 Pf antigens using Peak antibody levels, Peak antibody Deltas (difference between pre-immunization and post-immunization immunoreactivities), Pre-CHMI antibody levels and Pre-CHMI antibody Deltas against combinations of 6 Pf antigens in discriminating protection and susceptibility to CHMI.

| Antigens | Peak Levels | | Peak Deltas | | Pre-CHMI Levels | | Pre-CHMI Deltas | |
|---|---|---|---|---|---|---|---|---|
| | Sensitivity | Specificity | Sensitivity | Specificity | Sensitivity | Specificity | Sensitivity | Specificity |
| MSP5, PF3D7_1030200, GSK3, LRR9 | 0.78 | 0.80 | 0.89 | 0.80 | 0.89 | 0.80 | 0.89 | 0.80 |
| MSP5, PF3D7_1030200, DOC2, LRR9 | 0.78 | 0.80 | 0.89 | 0.80 | 1.00 | 1.00 | 0.89 | 0.80 |
| MSP5, GSK3, DOC2, LRR9 | 0.78 | 0.80 | 0.89 | 0.80 | 1.00 | 1.00 | 0.89 | 0.80 |
| PF3D7_1030200, GSK3, DOC2, LRR9 | 0.78 | 0.80 | 0.89 | 0.80 | 0.89 | 1.00 | 0.89 | 0.80 |
| CSP, MSP5, PF3D7_1030200, GSK3, DOC2 | 0.89 | 0.80 | 0.78 | 0.80 | 1.00 | 0.60 | 0.67 | 0.80 |
| CSP, MSP5, PF3D7_1030200, GSK3, LRR9 | 1.00 | 1.00 | 0.89 | 0.80 | 1.00 | 1.00 | 0.89 | 1.00 |
| CSP, MSP5, PF3D7_1030200, DOC2, LRR9 | 1.00 | 1.00 | 0.78 | 0.80 | 1.00 | 1.00 | 0.89 | 1.00 |
| CSP, MSP5, GSK3, DOC2, LRR9 | 0.89 | 0.80 | 0.89 | 0.80 | 1.00 | 1.00 | 0.89 | 1.00 |
| CSP, PF3D7_1030200, GSK3, DOC2, LRR9 | 1.00 | 1.00 | 0.89 | 1.00 | 1.00 | 1.00 | 0.89 | 0.80 |
| MSP5, PF3D7_1030200, GSK3, DOC2, LRR9 | 1.00 | 1.00 | 0.89 | 0.80 | 1.00 | 1.00 | 0.89 | 0.80 |
| CSP, MSP5, PF3D7_1030200, GSK3, DOC2, LRR9 | 1.00 | 1.00 | 0.89 | 0.80 | 1.00 | 1.00 | 0.89 | 1.00 |

TABLE 12

Performance characteristics of 6 Pf antigens using Peak antibody Deltas (difference between pre-immunization and post-immunization immunoreactivities) and Pre-CHMI antibody Deltas (difference between pre-immunization and pre-CHMI immunoreactivities) against combinations of 6 Pf antigens in discriminating protection and susceptibility to CHMI.

| Antigens | Peak Deltas | | Pre-CHMI Deltas | |
|---|---|---|---|---|
| | Sensitivity | Specificity | Sensitivity | Specificity |
| CSP | 0.89 | 0.40 | 0.89 | 0.60 |
| MSP5 | 0.67 | 0.80 | 0.67 | 0.60 |
| PF3D7_1030200 | 0.78 | 0.60 | 0.44 | 0.60 |
| GSK3 | 0.78 | 0.60 | 0.44 | 0.60 |
| DOC2 | 0.89 | 0.60 | 0.89 | 0.60 |
| LRR9 | 0.78 | 0.80 | 0.78 | 0.80 |
| CSP, MSP5 | 0.78 | 0.80 | 0.78 | 0.60 |
| CSP, PF3D7_1030200 | 0.44 | 0.60 | 0.78 | 0.60 |
| CSP, GSK3 | 0.78 | 0.60 | 0.89 | 0.60 |
| CSP, DOC2 | 0.67 | 0.60 | 0.78 | 0.60 |
| CSP, LRR9 | 0.78 | 0.80 | 0.78 | 0.80 |
| MSP5, PF3D7_1030200 | 0.78 | 0.80 | 0.56 | 0.60 |
| MSP5, GSK3 | 0.78 | 0.80 | 0.44 | 0.60 |
| MSP5, DOC2 | 0.67 | 0.80 | 0.78 | 0.60 |
| MSP5, LRR9 | 0.78 | 0.80 | 0.78 | 0.80 |
| PF3D7_1030200, GSK3 | 0.78 | 0.60 | 0.44 | 0.60 |
| PF3D7_1030200, DOC2 | 0.67 | 0.80 | 0.78 | 0.60 |
| PF3D7_1030200, LRR9 | 0.89 | 0.80 | 0.78 | 0.80 |
| GSK3, DOC2 | 0.67 | 0.80 | 0.78 | 0.60 |
| GSK3, LRR9 | 0.67 | 0.80 | 0.78 | 0.80 |
| DOC2, LRR9 | 0.78 | 0.80 | 0.78 | 0.80 |
| CSP, MSP5, PF3D7_1030200 | 0.78 | 0.80 | 0.89 | 0.60 |
| CSP, MSP5, GSK3 | 0.78 | 0.80 | 0.78 | 0.60 |
| CSP, MSP5, DOC2 | 0.67 | 0.80 | 0.78 | 0.80 |
| CSP, MSP5, LRR9 | 0.67 | 0.80 | 0.89 | 1.00 |
| CSP, PF3D7_1030200, GSK3 | 0.67 | 0.60 | 0.44 | 0.60 |
| CSP, PF3D7_1030200, DOC2 | 0.78 | 0.80 | 0.67 | 0.80 |
| CSP, PF3D7_1030200, LRR9 | 0.89 | 0.80 | 0.78 | 0.80 |
| CSP, GSK3, DOC2 | 0.78 | 0.80 | 0.78 | 0.60 |
| CSP, GSK3, LRR9 | 0.67 | 0.80 | 0.78 | 0.80 |
| CSP, DOC2, LRR9 | 0.78 | 0.80 | 0.78 | 0.80 |
| MSP5, PF3D7_1030200, GSK3 | 0.78 | 0.80 | 0.56 | 0.60 |
| MSP5, PF3D7_1030200, DOC2 | 0.78 | 0.80 | 0.78 | 0.60 |
| MSP5, PF3D7_1030200, LRR9 | 0.89 | 0.80 | 0.78 | 0.80 |
| MSP5, GSK3, DOC2 | 0.78 | 0.80 | 0.78 | 0.60 |
| MSP5, GSK3, LRR9 | 0.78 | 0.80 | 0.89 | 0.80 |
| MSP5, DOC2, LRR9 | 0.78 | 0.80 | 0.89 | 0.80 |
| PF3D7_1030200, GSK3, DOC2 | 0.67 | 0.80 | 0.78 | 0.60 |
| PF3D7_1030200, GSK3, LRR9 | 0.89 | 0.80 | 0.78 | 0.80 |
| PF3D7_1030200, DOC2, LRR9 | 0.89 | 0.80 | 0.89 | 0.80 |
| GSK3, DOC2, LRR9 | 0.78 | 0.80 | 0.78 | 0.80 |
| CSP, MSP5, PF3D7_1030200, GSK3 | 0.78 | 0.80 | 0.44 | 0.60 |
| CSP, MSP5, PF3D7_1030200, DOC2 | 0.78 | 0.80 | 0.78 | 0.80 |
| CSP, MSP5, PF3D7_1030200, LRR9 | 0.78 | 0.80 | 0.89 | 1.00 |

TABLE 12-continued

Performance characteristics of 6 Pf antigens using Peak antibody Deltas (difference between pre-immunization and post-immunization immunoreactivities) and Pre-CHMI antibody Deltas (difference between pre-immunization and pre-CHMI immunoreactivities) against combinations of 6 Pf antigens in discriminating protection and susceptibility to CHMI.

| Antigens | Peak Deltas | | Pre-CHMI Deltas | |
|---|---|---|---|---|
| | Sensitivity | Specificity | Sensitivity | Specificity |
| CSP, MSP5, GSK3, DOC2 | 0.78 | 0.80 | 0.78 | 0.80 |
| CSP, MSP5, GSK3, LRR9 | 0.89 | 0.80 | 0.89 | 1.00 |
| CSP, MSP5, DOC2, LRR9 | 0.67 | 0.80 | 0.89 | 1.00 |
| CSP, PF3D7_1030200, GSK3, DOC2 | 0.78 | 0.80 | 0.89 | 0.60 |
| CSP, PF3D7_1030200, GSK3, LRR9 | 0.89 | 0.80 | 0.78 | 0.80 |
| CSP, PF3D7_1030200, DOC2, LRR9 | 0.89 | 1.00 | 0.89 | 0.80 |
| CSP, GSK3, DOC2, LRR9 | 0.89 | 0.80 | 0.78 | 0.80 |
| MSP5, PF3D7_1030200, GSK3, DOC2 | 0.78 | 0.80 | 0.78 | 0.60 |
| MSP5, PF3D7_1030200, GSK3, LRR9 | 0.89 | 0.80 | 0.89 | 0.80 |
| MSP5, PF3D7_1030200, DOC2, LRR9 | 0.89 | 0.80 | 0.89 | 0.80 |
| MSP5, GSK3, DOC2, LRR9 | 0.89 | 0.80 | 0.89 | 0.80 |
| PF3D7_1030200, GSK3, DOC2, LRR9 | 0.89 | 0.80 | 0.89 | 0.80 |
| CSP, MSP5, PF3D7_1030200, GSK3, DOC2 | 0.78 | 0.80 | 0.67 | 0.80 |
| CSP, MSP5, PF3D7_1030200, GSK3, LRR9 | 0.89 | 0.80 | 0.89 | 1.00 |
| CSP, MSP5, PF3D7_1030200, DOC2, LRR9 | 0.78 | 0.80 | 0.89 | 1.00 |
| CSP, MSP5, GSK3, DOC2, LRR9 | 0.89 | 0.80 | 0.89 | 1.00 |
| CSP, PF3D7_1030200, GSK3, DOC2, LRR9 | 0.89 | 1.00 | 0.89 | 0.80 |
| MSP5, PF3D7_1030200, GSK3, DOC2, LRR9 | 0.89 | 0.80 | 0.89 | 0.80 |
| CSP, MSP5, PF3D7_1030200, GSK3, DOC2, LRR9 | 0.89 | 0.80 | 0.89 | 1.00 |

In the foregoing, the present invention has been described with reference to suitable embodiments, but these embodiments are only for purposes of understanding the invention and various alterations or modifications are possible so long as the present invention does not deviate from the claims that follow.

What is claimed is:

1. A method to elicit an immune response in a human subject against *Plasmodium*-induced malaria comprising:
administering a composition comprising (a) an immunogen component comprising at least one *Plasmodium*-specific polypeptide comprising an amino acid sequence that is at least 85% identical to SEQ ID NO:11; and (b) a carrier, to the subject.

2. The method of claim 1, wherein the amino acid sequence is at least 90% identical to SEQ ID NO:11.

3. The method of claim 1, wherein the amino acid sequence is at least 95% identical to SEQ ID NO:11.

4. The method of claim 1, wherein the amino acid sequence is at least 99% identical to SEQ ID NO:11.

5. The method of claim 1, wherein the amino acid sequence is 100% identical to SEQ ID NO:11.

6. The method of claim 1, wherein the immunogen component additionally comprises a *Plasmodium*-specific polypeptide comprising an amino acid sequence that is at least 85% identical to SEQ ID NO:19 or an antigenic fragment thereof.

7. The method of claim 6, wherein the amino acid sequence is 100% identical to SEQ ID NO:19 or an antigenic fragment thereof.

8. The method of claim 1, wherein the immunogen component additionally comprises a *Plasmodium*-specific polypeptide comprising an amino acid sequence that is at least 85% identical to SEQ ID NO:20 or an antigenic fragment thereof.

9. The method of claim 8, wherein the amino acid sequence is 100% identical to SEQ ID NO:20 or an antigenic fragment thereof.

10. The method of claim 1, wherein the immunogen component additionally comprises a *Plasmodium*-specific polypeptide comprising an amino acid sequence that is at least 85% identical to a sequence chosen from SEQ ID NO:12, SEQ ID NO:13, SEQ ID NO:14, or any combination thereof.

11. The method of claim 1, wherein the immunogen component additionally comprises a *Plasmodium*-specific polypeptide comprising an amino acid sequence 100% identical to SEQ ID NO:12.

12. The method of claim 1, wherein the immunogen component additionally comprises a *Plasmodium*-specific polypeptide comprising an amino acid sequence 100% identical to SEQ ID NO:13.

13. The method of claim 1, wherein the immunogen component additionally comprises a *Plasmodium*-specific polypeptide comprising an amino acid sequence 100% identical to SEQ ID NO:14.

14. The method of claim 1, wherein an etiology of the malaria comprises *P. falciparum, P. vivax, P. ovale, P. malariae*, or *P. knowlesi*.

15. The method of claim 14, wherein the etiology of the malaria is *P. falciparum*.

16. The method of claim 1, wherein the composition further comprises an excipient, preservative, adjuvant or other immune enhancer, additive, protectant, or any combination thereof.

17. The method of claim 1, wherein, prior to administration, the subject had not previously been exposed to a *malaria*-causing pathogen.

18. The method of claim 17, wherein the subject lacks an antibody that specifically immunoreacts with the immunogen component of the composition.

19. The method of claim 1, further comprising sequential or mixed immunization with attenuated *Plasmodium* species sporozoites.

20. The method of claim 19, wherein the attenuated *Plasmodium* species sporozoites are purified, aseptic, live attenuated sporozoites.

\* \* \* \* \*